US008859495B2

(12) United States Patent
Bamdad

(10) Patent No.: US 8,859,495 B2
(45) Date of Patent: Oct. 14, 2014

(54) METHODS FOR STIMULATING OR ENHANCING PROLIFERATION OF NON-TUMOROUS CELLS EXPRESSING MUC1 RECEPTORS

(75) Inventor: Cynthia C. Bamdad, Boston, MA (US)

(73) Assignee: Minerva Biotechnologies Corporation, Waltham, MA (US)

( * ) Notice: Subject to any disclaimer, the term of this patent is extended or adjusted under 35 U.S.C. 154(b) by 476 days.

(21) Appl. No.: 11/278,122

(22) Filed: Mar. 30, 2006

(65) Prior Publication Data

US 2006/0222637 A1    Oct. 5, 2006

Related U.S. Application Data

(60) Provisional application No. 60/667,216, filed on Mar. 30, 2005.

(51) Int. Cl.
*A61K 38/18* (2006.01)
*C07K 14/475* (2006.01)
*A61K 38/00* (2006.01)
*C07K 14/47* (2006.01)
*A61K 38/48* (2006.01)
*A61K 38/19* (2006.01)
*C07K 16/28* (2006.01)
*A61K 38/45* (2006.01)
*A61K 38/17* (2006.01)

(52) U.S. Cl.
CPC ............ *A61K 38/45* (2013.01); *A61K 38/4886* (2013.01); *C07K 2317/35* (2013.01); *A61K 38/193* (2013.01); *C07K 16/2863* (2013.01); *A61K 38/488* (2013.01); *A61K 38/1709* (2013.01)
USPC .......................................... 514/7.6; 514/7.5

(58) Field of Classification Search
None
See application file for complete search history.

(56) References Cited

U.S. PATENT DOCUMENTS

| | | | |
|---|---|---|---|
| 3,854,480 A | 12/1974 | Zaffaroni | |
| 4,452,775 A | 6/1984 | Kent | |
| 4,675,189 A | 6/1987 | Kent et al. | |
| 4,816,567 A | 3/1989 | Cabilly et al. | |
| 5,075,109 A | 12/1991 | Tice et al. | |
| 5,133,974 A | 7/1992 | Paradissis et al. | |
| 5,225,539 A | 7/1993 | Winter | |
| 5,407,686 A | 4/1995 | Patel et al. | |
| 5,585,089 A | 12/1996 | Queen et al. | |
| 5,693,762 A | 12/1997 | Queen et al. | |
| 5,736,152 A | 4/1998 | Dunn | |
| 5,834,217 A | 11/1998 | Levine et al. | |
| 5,859,205 A | 1/1999 | Adair et al. | |
| 2003/0036199 A1 | 2/2003 | Bamdad et al. | |
| 2004/0009147 A1* | 1/2004 | Ebner et al. | 424/85.1 |
| 2010/0093092 A1* | 4/2010 | Bamdad et al. | 435/377 |

FOREIGN PATENT DOCUMENTS

| | | | |
|---|---|---|---|
| EP | 0 239 400 A2 | 9/1987 | |
| WO | WO 88/09344 A1 | 12/1988 | |
| WO | WO 89/09622 A1 | 10/1989 | |
| WO | WO 90/07861 A1 | 7/1990 | |
| WO | WO 91/10741 A1 | 7/1991 | |
| WO | WO 94/02602 A1 | 2/1994 | |
| WO | WO 95/24929 A2 | 9/1995 | |
| WO | WO 96/33735 A1 | 10/1996 | |
| WO | WO 96/34096 A1 | 10/1996 | |
| WO | WO 02/056022 A2 | 7/2002 | |
| WO | WO 03/074074 A1 | 9/2003 | |
| WO | 03/106495 * | 12/2003 | ............ C07K 16/00 |
| WO | WO 2004/002259 A2 | 3/2004 | |
| WO | WO 2004/022590 A2 | 3/2004 | |
| WO | WO 2005/019269 A2 | 3/2005 | |
| WO | WO 2007/053135 A1 | 5/2007 | |

OTHER PUBLICATIONS

Alberts et al. 1994. Molecular Biology of the Cell pp. 129-130.*
Dubreuil-Lemaire 2000. Eur J Haematol 65:337-343.*
Thathiah et al., "Tumor Necrosis Factor α Stimulates MUC1 Synthesis and Ectodomain Release in a Human Uterine Epithelial Cell Line," Endocrinology, 145(9): 4192-4203 (2004).
Thathiah et al., "Tumor Necrosis Factor-α Converting Enzyme/Adam 17 Mediates MUC1 Shedding," The Jounral of Biological Chemistry., 278(5): 3386-3394 (2003).
Gad et al., "MUC1-Derived Glycopeptide Libraries With Improved MHC Anchors are Strong Antigens and Prime Mouse T Cells for Profliferative Responses to Lysates of Human Breast Cancer Tissue," Eur. Journal of Immunology, 33: 1624-1632 (2003).
Barratt-Boyes et al., "Immunization of Chimpanzees With Tumor Antigen MUC1 Mucin Tandem Repeat Peptide Elicits Both Helper and Cytotoxic T-Cell Responses," Clinical Cancer Research, 5: 1918-1924 (1999).
Wright et al., "Cytotoxic T Lymphocytes From Humans With Adenocarcinomas Stimulated by Native MUC1 Mucin and a Mucin Peptide Mutated at a Glycosylation Site," Journal of Immunotherapy 23 ;2-10, 2000.
Hanisch, "Design of a MUC1-Based Cancered Vaccine," The Molecular Biology of Colorectal Cancer, 33: 705-708 (2005).
Al-Hajj et al., "Prospective identification of tumorigenic breast cancer cells," PNAS (2003), 100(7): 3988-3988.
Allsopp et al., "Comparison of numerous delivery systems for the induction of cytoxic T lymphocytes by immuniziation," Eur J Immunol. (1996), 26(8): 1951-9, Abstract Only.
Bonnet and Dick, "Human acute myeloid leukemia is organized as a hierarchy that originates from a primitive hematopoietic cell." Nat Med. (1997), 3(7): 730-7, Abstract Only.
Briasoulis et al., "G-CSF Induces Elevation of Circulating CA 15-3 in Breast Carcinoma Patients Treated in an Adjuvant Setting," Am. Cancer Society (2001), 91(5): 909-917.
Burchell et al., "Development and characterization of breast cancer reactive monoclonal antibodies directed to the core protein of the human milk mucin," Cancer Research (1987), 47(20): 5476-5482, Abstract Only.

(Continued)

*Primary Examiner* — Robert Landsman
(74) *Attorney, Agent, or Firm* — Joseph H Kim; JHK Law

(57) ABSTRACT

The present application discloses a method for stimulating or enhancing proliferation of a population of cells by activating MUC1 receptor on the cells.

40 Claims, 14 Drawing Sheets

(56) References Cited

OTHER PUBLICATIONS

Byrd and Bresalier, "Mucins and mucin binding proteins in colorectal cancer," Cancer and Metastasis Reviews (2004), 23: 77-99.

Al-Hajj and Clarke, "Self-renewal and solid tumor stem cells," Oncogene (2004), 23: 7274-7282.

Chengalvala et al., "Replication and immunogenicity of Ad7, Ad4-, and Ad5-hepatitis B virus surface antigen recombinants, with or without a portion of E3 region, in chimpanzees," Vaccine, (1997), 15(3): 335-339.

Cloosen et al., "Mucin-1 is expressed on dendritic cells, both in vitro and in vivo," International Immunology (2004), 16(11): 1561-1571, Abstract Only.

Dahiyat and Mayo, De novo Protein Design: Fully Automated Sequence Selection, Science (1997), 278: 82-87.

Davis et al., "Vaccination of Macaques against Pathogenic Simian Immunodeficiency Virus with Venezuelan Equine Encephalitis Virus Replicon Particles," Journal of Virology (2000), 74(1): 371-378.

Eloit et al., "High Level of Transgene Expression in Cell Cultures and in the Mouse by Replication-Incompetent Adenoviruses Harboring Modified VAI Genes," Journal of Virology (1997), 71(7): 5375-5381.

Gendler et al., "Molecular Cloning and Expression of Human Tumor-associated Polymorphic Epithelial Mucin," Journal of Biological Chemistry (1990), 265(25): 15286-15293.

Goldspiel et al., "Human gene therapy," Clin Pharm. (1993), 12(7): 488-505, Abstract Only.

Irwin et al., "Direct Injection of a Recombinant Retroviral Vector Induces Human Immunodeficiency Virus-Specific Immune Responses in Mice and Nonhuman Primates," Journal of Virology (1994), 68(8): 5036-5044.

Jarrard et al., "MUC1 is a novel marker for the type II pneumocyte lineage Strait during lung carcinogenesis," Cancer Research (1998), 58(23): 5582-5589, Abstract Only.

Koller and Smithies, "Inactivating the Beta sub 2-microglobulin locus in mouse embryonic stem cells by homologous recombination," Proc. Natl. Acad. Sci. USA (1989), 86: 8932-8935.

Kufe et al., "Differential reactivity of a novel monoclonal antibody (DF3) with human malignant versus benign breast tumors," Hybridoma (1984), 3(3): 223-32, Abstract Only.

Lapidot et al., "A cell initiating human acute myeloid leukemia after transplantation into SCID mice," Nature (1994), 367: 645-648.

Leong et al., "Epithelial membrane antigen (EMA) or MUC1 expression in monocytes and monoblasts," Pathology (2003), 35(5): 422-427.

Ligtenberg et al., "Episialin, a Carcinoma-associated Mucin, Is Generated by a Polymorphic Gene Encoding Splice Variants with Alternative Amino Termini," Journal of Biological Chemistry (1990), 265(10): 5573-5578.

Matsui et al., "Characterization of clonogenic multiple myeloma cells," Blood (2004), 103(6): 2232-2236.

Meseguer et al., "Human Endometrial Mucin MUC1 Is Up-Regulated by Progesterone and Down-Regulated in Vitro by the Human Blastocyst," Biology of Reproduction (2001), 64: 590-601.

Morgan and Anderson, "Human Gene Therapy," Annual Reviews Biochemistry (1993), 62: 191-217.

Moss, B., "Genetically engineered poxviruses for recombinant gene expression, vaccination, and safety," Proc. Natl. Acad. Sci. USA (1996), 93:11341-11348.

Moss, B., "Replicating and host-restricted non-replicating vaccinia virus vectors for vaccine development," Dev Biol Stand. (1994), 82: 55-63, Abstract Only.

Mulligan, R., "The Basic Science of Gene Therapy," Science (1993), 260: 926-932.

Paoletti, E., "Applications of pox virus vectors to vaccination: An update," Proc. Natl. Acad. Sci. USA (1996), 93: 11349-11353.

Pugachev et al., "Double-Subgenomic Sindbis Virus Recombinants Expressing Immunogenic Proteins of Japanese Encephalitis Virus Induce Significant Protection in Mice against Lethal JEV Infection," Virology (1995), 212: 587-594.

Rughetti et al., "Regulated expression of MUC1 epithelial antigen in erythropoiesis," British Journal of Haemathology (2003), 120: 344-352.

Sawhney et al., "Bioerodible Hydrogels Based on Photopolymerized Poly (ethylene glycol)-co-poly (alpha-hydroxy acid) Diacrylate Macromers," Macromolecules (1993), 26: 581-587, Abstract Only.

Singh 'et al., "Identification of a Cancer Stem Cell in Human Brain Tumors," Cancer Research (2003), 63: 5821-5828.

Spicer et al., "Molecular Cloning and Analysis of the Mouse Homologue of the Tumor-associated Mucin, MUC1, Reveals Conservation of Potential O-Glycosylation Sites, Transmembrane, and Cytoplasmic Domains and a Loss of Minisatellite-like Polymorphism," Journal of Biological Chemistry (1991), 266(23): 15099-15109.

Stingl et al., "Epithelial Progenitors in the Normal Human Mammary Gland," Journal of Mammary Gland Biology and Neoplasia (2005), 10(1): 49-59.

Tolstoshev, P., "Gene Therapy, Concepts, Current Trials and Future Directions," Annual Reviews Pharmocology Toxicology (1993), 32: 573-596.

Townsend et al., "Characterization of CD8+ Cytotoxic T-Lymphocyte Responses after Genetic Immunization with Retrovirus Vectors Expressing Different Forms of the Hepatitis B Virus Core and e Antigens," Journal of Virology (1997), 71(5): 3365-3374.

Vacanti et al., "Identification and Initial Characterization of Spore-Like Cells in Adult Mammals," Journal of Cellular Biochemistry (2001), 80: 455-460.

Wu, G. and Wu, C., "Receptor-mediated in Vitro Gene Transformation by a Soluble DNA Carrier System," Journal of Biological Chemistry (1987), 262(10): 4429-4432.

Wu, G. and Wu, C., "Delivery systems for gene therapy," Biotherapy (1991), 3 (1): 1573-8280, Abstract Only.

Xiang et al., "A Replication-Defective Human Adenovirus Recombinant Serves as a Highly Efficacious Vaccine Carrier," Virology (1996), 219: 220-227.

Zhong et al., "Evaluation of MUC1 and EGP40 in bone marrow and peripheral blood as a marker for occult breast cancer," Arch Gynecol Obstet (2001), 264: 177-181.

Zhou et al., "Generation of cytotoxic and humoral immune responses by nonreplicative recombinant Semliki Forest virus," Proc. Natl. Acad. Sci. USA (1995), 92: 3009-3013.

Zijlstra et al., "Germ-line transmission of a disrupted Beta sub-2 microglobulin gene produced by homologous recombination in embryonic stem cells," Nature (1989), 342: 435-438.

Zotter et al., "Monoclonal antibodies to epithelial sialomucins recognize epitopes at different cellular sites in adenolymphomas of the parotid gland," Int J Cancer Suppl. (1988), 3: 38-44, Abstract Only.

Hanisch, F. G. "Design of as MUC1-based cancer vaccine," Mol. Biol. Colorectal Cancer: Cancer; 33:705-708, 2005.

Thathiah et al., "Tumor Necrosis factor-alpha Converting Enzyme/ADAM 17 Mediates MUC1 Shedding," J. Biol. Chem, 278:3386-3394, 2003.

Wright et al., "Cytotoxic T Lymphocytes from Humans with Adenocarcinomas Stimulated by Native MUC1 Mucin and a Mucin Peptide Mutated at a Glycosylation Site," J. Immunother; 23:2-16, 2000.

Gad et al., "MUC1-derived glycopeptide iibraries with improved MHC anchors are strong antigens and prime mouse T cells for proliferative response to lysates of human breast cancer tissue," Eur. J. Immunol., 33:1624-1632, 2003.

Barrat-Boyes et al., "Immunization of Chimpanzees with Tumor Antigen MUC1 Mucin Tandem Repeat Peptide Elicits" Clin. Can. Res., 5:1918-1924, 1999.

Thathiah et al., "Tumor Necrosis Factor alpha Stimulates MUC1 Synthesis . . . ," Endocrinol., 145:4192-4203, 2004.

Mahanta, Sanjeev et al., "A minimal fragment of MUC1 mediates growth of cancer cells," PLOS ONE, 3(4):1-12, 2008.

Hikita, Sherry T. et al., "MUC*1 mediates the growth of human pluripotent stem cells," PLOS ONE, 3(10);1-13, 2008.

Al-Hajj et al., "Prospective identification of Tumorigenic Breast Cancer Cells," PNAS, 100(7):3983-3988, 2003.

Al-Hajj et al., "Self Renewal and Solid Tumor Stem Cells," Oncogene, 23:7274-7282, 2004.

(56) References Cited

OTHER PUBLICATIONS

Bonnet et al., "Human Acute Myeloid Leukemia is Organized as a Hierarchy that Originates from a Primitive Hematopoietic Cell," Nature Medicine; 3(7):730-737, 1997.
Briasoulis et al., "G-CSF Induces Elevation of Circulating CA 15-3 in Breast Carcinoma Patients Treated in an Adjuvant Setting," American Cancer Society, 91(5):909-917, 2001.
Burchell et al., "Development and Characterization of Breast Cancer Reactive Monoclonal Antibodies Directed to the Core Protein of the Human Milk Mucin," Cancer Res., 47:5476-5482, 1987.
Byrd et al., "Mucins and Mucin Binding Proteins in Colorectal Cancer," Cancer and Metastasis Reviews, 23:77-99, 2004.
Clarke, R. B., "Isolation and Characterization of Human Mammary Stem Cells," Cell Prolif., 38:375-386, 2005.
Cloosen et al., "Mucin-1 is Expressed on Dendritic Cells, both In Vitro and In Vivo," International Immunology, 16(11):1561-1571, 2004.
Gad et al., MUC 1-Derived Glycopeptide Libraries with Improved MHC Anchors are Strong Antigens and Prime Mouse T Cells for Proliferative Responses to Lysates of Human Breast Cancer Tissue, Eur. J. Immunol., 33: 1624-1632, 2003.
Gendler et al., "Molecular Cloning and Expression of Human Tumor-Associated Polymorphic Epithelial Mucin," The Journal of Biological Chemistry, 265(25):15286-15293, 1990.
Gervasi et al., "nm23 Influences Proliferation and Differentiation of PC12 Cells in Response to Nerve Growth Factor1," Cell Growth and Differentiation, 7:1689-1695, 1996.
Hanisch, F.-G., "Design of a MUC1-Based Cancer Vaccine," Biochemical Society, 33(4):705-708, 2005.
Hikita et al., "MUC1* Mediates the Growth of Human Pluripotent Stem Cells," PLoS One, 3(10):1-13, 2008.
Jarrard et al., "MUC1 is a Novel Marker for the Type II Pneumocyte Lineage during Lung Carcinogenesis," Cancer Res., 58:5582-5589, 1998.
Kim et al., "Point Mutations Affecting the Oligomeric Structure of Nm23-H1 Abrogates its Inhibitory Activity on Colonization and Invasion of Prostate Cancer Cells," Biochemical and Biophysical Research Communications, 307:281-289, 2003.
Kufe et al., "Differential Reactivity of a Novel Monoclonal Antibody (DF3) with Human Malignant Versus Benign Breast Tumors," Hybridoma, 3(3):223-232, 1984.
Lapidot et al., "A Cell Initiating Human Acute Myeloid Leukaemia after Transplantation into SCID Mice", Letters to Nature. 367:645-648, 1994.
Lascu et al., "Quaternary Structure of Nucleside Diphosphate Kinases," Journal of Bioenergetics and Biomembranes, 32(3): 227-236, 2000.
Ligtenberg et al., "Episialin, a Carcinoma-associated Mucin, is Generated by a Polymorphic Gene Encoding Splice Variants with Alternative Amino Termini*", The Journal of Biological Chernistry, 265(10):5573-5578, 1990.
Lombardi et al., "nm23: Unraveling its Biological Function in Cell Differentiation," Journal of Cellular Physiology, 182:144-149, 2000.
Luong et al., "Expression of Nm23-H1 in AML correlates with White Cell Count at Diagnosis and In Vitro Acts as a Survival Factor for Primary AMLs cells; Evidence of a Novel Autocrine Survival Factor in AML," XP-001193730, 102(11 ):611a, 2003.
MacDonald et al., "Site-Directed Mutagenesis of nm23-H1," The Journal of Biological Chemistry, 271(41):25107-25116, 1996.
Mahanta et al., "A Minimal Fragment of MUC1 Mediates Growth of Cancer Cells," PLoS One, 3(4):1-12, 2008.
Matsui et al., "Characterization of Clonogenic Multiple Myeloma Cells", Blood, 103(6):2332-2336, 2004.
Meseguer et al., "Human Endometrial Mucin MUC1 is Up-Regulated by Progesterone and Down-Regulated In Vitro by the Human Blastocyst," Biology of Reproduction, 64:590-601, 2001.
Negroni et al., "Neuroblastoma Specific Effects of DR-nm23 and its Mutant Forms on Differentiation and Apoptosis," Cell Death and Differentiation, 7:843-850, 2000.
Okabe-Kado et al., "A New Function of Nm23/NDP Kinase as a Differentiation Inhibitory Factor, Which Does Not Require it's Kinase Activity," FEBS Letters, 363:311-315, 1995.
Okabe-Kado et al., "Characterization of a Differentiation-Inhibitory Activity from Nondifferentiating Mouse Myeloid Leukemia Cells," Cancer Research, 45:4848-4852, 1985.
Okabe-Kado at al., "Identity of a Differentiation inhibiting Factor for Mouse Myeloid Leukemia Cells with NM23/Nucleoside Diphosphate Kinase," Biochemical and Biophysical Research Communications, 182(3):987-994, 1992.
Okabe-Kado et al., "Inhibitory Action of nm23 Proteins on Induction of Erythroid Differentiation of Human Leukemia Cells," Biochimica et Biophysica Acta., 1267:101-106, 1995.
Okabe-Kado et al., "Physiological and Pathological Relevance of Extracellular NM23/NDP Kinases," Journal of Bioenergetics and Biomembranes, 35(1).89-93, 2003.
Rughetti et al., "Regulated Expression of MUC1 Epithelial Antigen in Erythropoiesis," British Journal of Haematology, 120:344-352, 2003.
Singh et al., "Identification of a Cancer Stem Cell in Human Brain Tumors," Cancer Res., 63:5821-5828, 2003.
Spicer et al., "Molecular Cloning and Analysis of the Mouse Homologue of the Tumor-associated Mucin, MUC1, Reveals Conservation of Potential O-Glycosylation Sites, Transmembrane, and Cytoplasmic Domains and a Loss of Minisatellite-Like Polymorphism," The Journal of Biological Chemistry, 266(23):15099-15109, 1991.
Stingl at al., "Epithelial Progenitors in the Normal Human Mammary Gland," Journal of Mammary Gland Biology and Neoplasia, 10(1):49-59, 2005.
Vacanti et al., "Identification and Initial Characterization of Spore-Like Cells in Adult Mammals," Journal of Cellular Biochemistry, 80:455-460, 2001.
Venturelli et al., "Overexpression of DR-nm23, a Protein Encoded by a Member of the nm23 Gene Family, Inhibits Granulocyte Differentiation and Induces Apoptosis in 32Dc13 Myeloid Cells," Pro. Natl. Acad. Sci. USA, 92:7435-7439, 1995.
Willems et al., Extracellular Nucleoside Diphosphate Kinase NM23/NDPK Modulates Normal Hematopoietic Differentiation, Experimental Hematology, 30:640-648, 2002.
Zhong et al., "Evaluation of MUC1 and EGP4O in Bone Marrow and Peripheral Blood as a Marker for Occult Breast Cancer," Arch Gynecol Obstet, 264:177-181, 2001.

* cited by examiner

SEQUENCE LISTING

<160> NUMBER OF SEQ ID NOS: 25

<210> SEQ ID NO 1
<211> LENGTH: 1255
<212> TYPE: PRT
<213> ORGANISM: Homo sapiens

<400> SEQUENCE: 1

Met Thr Pro Gly Thr Gln Ser Pro Phe Phe Leu Leu Leu Leu Leu Thr
 1               5                  10                  15

```
Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Val Ser Met Thr Ser Ser Val Leu Ser Ser His
    50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
        115                 120                 125

Gly Ser Thr Ala Pro Pro Ala His Gly Val Thr Ser Ala Pro Asp Thr
    130                 135                 140

Arg Pro Ala Pro Gly Ser Thr Ala Pro Pro Ala His Gly Val Thr Ser
145                 150                 155                 160

Ala Pro Asp Thr Arg Pro Ala Pro Gly Ser Thr Ala Pro Pro Ala His
                165                 170                 175

Gly Val Thr Ser Ala Pro Asp Thr Arg Pro Ala Pro Gly Ser Thr Ala
            180                 185                 190

Pro Pro Ala His Gly Val Thr Ser Ala Pro Asp Thr Arg Pro Ala Pro
        195                 200                 205

Gly Ser Thr Ala Pro Pro Ala His Gly Val Thr Ser Ala Pro Asp Thr
    210                 215                 220

Arg Pro Ala Pro Gly Ser Thr Ala Pro Pro Ala His Gly Val Thr Ser
225                 230                 235                 240

Ala Pro Asp Thr Arg Pro Ala Pro Gly Ser Thr Ala Pro Pro Ala His
                245                 250                 255

Gly Val Thr Ser Ala Pro Asp Thr Arg Pro Ala Pro Gly Ser Thr Ala
            260                 265                 270

Pro Pro Ala His Gly Val Thr Ser Ala Pro Asp Thr Arg Pro Ala Pro
        275                 280                 285

Gly Ser Thr Ala Pro Pro Ala His Gly Val Thr Ser Ala Pro Asp Thr
    290                 295                 300

Arg Pro Ala Pro Gly Ser Thr Ala Pro Pro Ala His Gly Val Thr Ser
305                 310                 315                 320

Ala Pro Asp Thr Arg Pro Ala Pro Gly Ser Thr Ala Pro Pro Ala His
                325                 330                 335

Gly Val Thr Ser Ala Pro Asp Thr Arg Pro Ala Pro Gly Ser Thr Ala
            340                 345                 350

Pro Pro Ala His Gly Val Thr Ser Ala Pro Asp Thr Arg Pro Ala Pro
        355                 360                 365

Gly Ser Thr Ala Pro Pro Ala His Gly Val Thr Ser Ala Pro Asp Thr
    370                 375                 380

Arg Pro Ala Pro Gly Ser Thr Ala Pro Pro Ala His Gly Val Thr Ser
385                 390                 395                 400

Ala Pro Asp Thr Arg Pro Ala Pro Gly Ser Thr Ala Pro Pro Ala His
                405                 410                 415

Gly Val Thr Ser Ala Pro Asp Thr Arg Pro Ala Pro Gly Ser Thr Ala
            420                 425                 430

Pro Pro Ala His Gly Val Thr Ser Ala Pro Asp Thr Arg Pro Ala Pro
```

```
                435                 440                 445
Gly Ser Thr Ala Pro Pro Ala His Gly Val Thr Ser Ala Pro Asp Thr
            450                 455                 460
Arg Pro Ala Pro Gly Ser Thr Ala Pro Pro Ala His Gly Val Thr Ser
465                 470                 475                 480
Ala Pro Asp Thr Arg Pro Ala Pro Gly Ser Thr Ala Pro Pro Ala His
                485                 490                 495
Gly Val Thr Ser Ala Pro Asp Thr Arg Pro Ala Pro Gly Ser Thr Ala
            500                 505                 510
Pro Pro Ala His Gly Val Thr Ser Ala Pro Asp Thr Arg Pro Ala Pro
            515                 520                 525
Gly Ser Thr Ala Pro Pro Ala His Gly Val Thr Ser Ala Pro Asp Thr
            530                 535                 540
Arg Pro Ala Pro Gly Ser Thr Ala Pro Pro Ala His Gly Val Thr Ser
545                 550                 555                 560
Ala Pro Asp Thr Arg Pro Ala Pro Gly Ser Thr Ala Pro Pro Ala His
                565                 570                 575
Gly Val Thr Ser Ala Pro Asp Thr Arg Pro Ala Pro Gly Ser Thr Ala
            580                 585                 590
Pro Pro Ala His Gly Val Thr Ser Ala Pro Asp Thr Arg Pro Ala Pro
            595                 600                 605
Gly Ser Thr Ala Pro Pro Ala His Gly Val Thr Ser Ala Pro Asp Thr
            610                 615                 620
Arg Pro Ala Pro Gly Ser Thr Ala Pro Pro Ala His Gly Val Thr Ser
625                 630                 635                 640
Ala Pro Asp Thr Arg Pro Ala Pro Gly Ser Thr Ala Pro Pro Ala His
                645                 650                 655
Gly Val Thr Ser Ala Pro Asp Thr Arg Pro Ala Pro Gly Ser Thr Ala
            660                 665                 670
Pro Pro Ala His Gly Val Thr Ser Ala Pro Asp Thr Arg Pro Ala Pro
            675                 680                 685
Gly Ser Thr Ala Pro Pro Ala His Gly Val Thr Ser Ala Pro Asp Thr
            690                 695                 700
Arg Pro Ala Pro Gly Ser Thr Ala Pro Pro Ala His Gly Val Thr Ser
705                 710                 715                 720
Ala Pro Asp Thr Arg Pro Ala Pro Gly Ser Thr Ala Pro Pro Ala His
                725                 730                 735
Gly Val Thr Ser Ala Pro Asp Thr Arg Pro Ala Pro Gly Ser Thr Ala
            740                 745                 750
Pro Pro Ala His Gly Val Thr Ser Ala Pro Asp Thr Arg Pro Ala Pro
            755                 760                 765
Gly Ser Thr Ala Pro Pro Ala His Gly Val Thr Ser Ala Pro Asp Thr
            770                 775                 780
Arg Pro Ala Pro Gly Ser Thr Ala Pro Pro Ala His Gly Val Thr Ser
785                 790                 795                 800
Ala Pro Asp Thr Arg Pro Ala Pro Gly Ser Thr Ala Pro Pro Ala His
                805                 810                 815
Gly Val Thr Ser Ala Pro Asp Thr Arg Pro Ala Pro Gly Ser Thr Ala
            820                 825                 830
Pro Pro Ala His Gly Val Thr Ser Ala Pro Asp Thr Arg Pro Ala Pro
            835                 840                 845
Gly Ser Thr Ala Pro Pro Ala His Gly Val Thr Ser Ala Pro Asp Thr
            850                 855                 860
```

```
Arg Pro Ala Pro Gly Ser Thr Ala Pro Ala His Gly Val Thr Ser
865                 870                 875                 880

Ala Pro Asp Thr Arg Pro Ala Pro Gly Ser Thr Ala Pro Ala His
                885                 890                 895

Gly Val Thr Ser Ala Pro Asp Thr Arg Pro Ala Pro Gly Ser Thr Ala
            900                 905                 910

Pro Pro Ala His Gly Val Thr Ser Ala Pro Asp Thr Arg Pro Ala Pro
        915                 920                 925

Gly Ser Thr Ala Pro Ala His Gly Val Thr Ser Ala Pro Asp Asn
930                 935                 940

Arg Pro Ala Leu Gly Ser Thr Ala Pro Val His Asn Val Thr Ser
945                 950                 955                 960

Ala Ser Gly Ser Ala Ser Gly Ser Ala Ser Thr Leu Val His Asn Gly
            965                 970                 975

Thr Ser Ala Arg Ala Thr Thr Thr Pro Ala Ser Lys Ser Thr Pro Phe
            980                 985                 990

Ser Ile Pro Ser His His Ser Asp Thr Pro Thr Thr Leu Ala Ser His
        995                 1000                1005

Ser Thr Lys Thr Asp Ala Ser Thr His Ser Ser Val Pro
    1010                1015            1020

Pro Leu Thr Ser Ser Asn His Ser Thr Ser Pro Gln Leu Ser Thr
            1025                1030                1035

Gly Val Ser Phe Phe Phe Leu Ser Phe His Ile Ser Asn Leu Gln
    1040                1045                1050

Phe Asn Ser Ser Leu Glu Asp Pro Ser Thr Asp Tyr Tyr Gln Glu
    1055                1060                1065

Leu Gln Arg Asp Ile Ser Glu Met Phe Leu Gln Ile Tyr Lys Gln
    1070                1075                1080

Gly Gly Phe Leu Gly Leu Ser Asn Ile Lys Phe Arg Pro Gly Ser
    1085                1090                1095

Val Val Val Gln Leu Thr Leu Ala Phe Arg Glu Gly Thr Ile Asn
    1100                1105                1110

Val His Asp Val Glu Thr Gln Phe Asn Gln Tyr Lys Thr Glu Ala
    1115                1120                1125

Ala Ser Arg Tyr Asn Leu Thr Ile Ser Asp Val Ser Val Ser Asp
    1130                1135                1140

Val Pro Phe Pro Phe Ser Ala Gln Ser Gly Ala Gly Val Pro Gly
    1145                1150                1155

Trp Gly Ile Ala Leu Leu Val Leu Val Cys Val Leu Val Ala Leu
    1160                1165                1170

Ala Ile Val Tyr Leu Ile Ala Leu Ala Val Cys Gln Cys Arg Arg
    1175                1180                1185

Lys Asn Tyr Gly Gln Leu Asp Ile Phe Pro Ala Arg Asp Thr Tyr
    1190                1195                1200

His Pro Met Ser Glu Tyr Pro Thr Tyr His Thr His Gly Arg Tyr
    1205                1210                1215

Val Pro Pro Ser Ser Thr Asp Arg Ser Pro Tyr Glu Lys Val Ser
    1220                1225                1230

Ala Gly Asn Gly Gly Ser Ser Leu Ser Tyr Thr Asn Pro Ala Val
    1235                1240                1245

Ala Ala Ala Ser Ala Asn Leu
    1250                1255
```

<210> SEQ ID NO 2
<211> LENGTH: 19
<212> TYPE: PRT
<213> ORGANISM: Homo sapiens

<400> SEQUENCE: 2

Met Thr Pro Gly Thr Gln Ser Pro Phe Phe Leu Leu Leu Leu Thr
1               5                   10                  15

Val Leu Thr

<210> SEQ ID NO 3
<211> LENGTH: 23
<212> TYPE: PRT
<213> ORGANISM: Homo sapiens

<400> SEQUENCE: 3

Met Thr Pro Gly Thr Gln Ser Pro Phe Phe Leu Leu Leu Leu Thr
1               5                   10                  15

Val Leu Thr Val Val Thr Ala
            20

<210> SEQ ID NO 4
<211> LENGTH: 23
<212> TYPE: PRT
<213> ORGANISM: Homo sapiens

<400> SEQUENCE: 4

Met Thr Pro Gly Thr Gln Ser Pro Phe Phe Leu Leu Leu Leu Thr
1               5                   10                  15

Val Leu Thr Val Val Thr Gly
            20

<210> SEQ ID NO 5
<211> LENGTH: 146
<212> TYPE: PRT
<213> ORGANISM: Homo sapiens

<400> SEQUENCE: 5

Gly Thr Ile Asn Val His Asp Val Glu Thr Gln Phe Asn Gln Tyr Lys
1               5                   10                  15

Thr Glu Ala Ala Ser Arg Tyr Asn Leu Thr Ile Ser Asp Val Ser Val
            20                  25                  30

Ser Asp Val Pro Phe Pro Phe Ser Ala Gln Ser Gly Ala Gly Val Pro
        35                  40                  45

Gly Trp Gly Ile Ala Leu Leu Val Leu Val Cys Val Leu Val Ala Leu
    50                  55                  60

Ala Ile Val Tyr Leu Ile Ala Leu Ala Val Cys Gln Cys Arg Arg Lys
65                  70                  75                  80

Asn Tyr Gly Gln Leu Asp Ile Phe Pro Ala Arg Asp Thr Tyr His Pro
                85                  90                  95

Met Ser Glu Tyr Pro Thr Tyr His Thr His Gly Arg Tyr Val Pro Pro
            100                 105                 110

Ser Ser Thr Asp Arg Ser Pro Tyr Glu Lys Val Ser Ala Gly Asn Gly
        115                 120                 125

Gly Ser Ser Leu Ser Tyr Thr Asn Pro Ala Val Ala Ala Ser Ala
    130                 135                 140

Asn Leu
145

<210> SEQ ID NO 6
<211> LENGTH: 171
<212> TYPE: PRT
<213> ORGANISM: Homo sapiens

<400> SEQUENCE: 6

Gly Phe Leu Gly Leu Ser Asn Ile Lys Phe Arg Pro Gly Ser Val Val
1               5                   10                  15

Val Gln Leu Thr Leu Ala Phe Arg Glu Gly Thr Ile Asn Val His Asp
            20                  25                  30

Val Glu Thr Gln Phe Asn Gln Tyr Lys Thr Glu Ala Ala Ser Arg Tyr
        35                  40                  45

Asn Leu Thr Ile Ser Asp Val Ser Val Ser Asp Val Pro Phe Pro Phe
    50                  55                  60

Ser Ala Gln Ser Gly Ala Gly Val Pro Gly Trp Gly Ile Ala Leu Leu
65                  70                  75                  80

Val Leu Val Cys Val Leu Val Ala Leu Ala Ile Val Tyr Leu Ile Ala
                85                  90                  95

Leu Ala Val Cys Gln Cys Arg Arg Lys Asn Tyr Gly Gln Leu Asp Ile
            100                 105                 110

Phe Pro Ala Arg Asp Thr Tyr His Pro Met Ser Glu Tyr Pro Thr Tyr
        115                 120                 125

His Thr His Gly Arg Tyr Val Pro Pro Ser Ser Thr Asp Arg Ser Pro
    130                 135                 140

Tyr Glu Lys Val Ser Ala Gly Asn Gly Gly Ser Ser Leu Ser Tyr Thr
145                 150                 155                 160

Asn Pro Ala Val Ala Ala Ala Ser Ala Asn Leu
                165                 170

<210> SEQ ID NO 7
<211> LENGTH: 275
<212> TYPE: PRT
<213> ORGANISM: Homo sapiens

<400> SEQUENCE: 7

Ala Thr Thr Thr Pro Ala Ser Lys Ser Thr Pro Phe Ser Ile Pro Ser
1               5                   10                  15

His His Ser Asp Thr Pro Thr Thr Leu Ala Ser His Ser Thr Lys Thr
            20                  25                  30

Asp Ala Ser Ser Thr His His Ser Thr Val Pro Pro Leu Thr Ser Ser
        35                  40                  45

Asn His Ser Thr Ser Pro Gln Leu Ser Thr Gly Val Ser Phe Phe Phe
    50                  55                  60

Leu Ser Phe His Ile Ser Asn Leu Gln Phe Asn Ser Ser Leu Glu Asp
65                  70                  75                  80

Pro Ser Thr Asp Tyr Tyr Gln Glu Leu Gln Arg Asp Ile Ser Glu Met
                85                  90                  95

Phe Leu Gln Ile Tyr Lys Gln Gly Gly Phe Leu Gly Leu Ser Asn Ile
            100                 105                 110

Lys Phe Arg Pro Gly Ser Val Val Val Gln Leu Thr Leu Ala Phe Arg
        115                 120                 125

Glu Gly Thr Ile Asn Val His Asp Val Glu Thr Gln Phe Asn Gln Tyr
    130                 135                 140

Lys Thr Glu Ala Ala Ser Arg Tyr Asn Leu Thr Ile Ser Asp Val Ser
145                 150                 155                 160

```
Val Ser Asp Val Pro Phe Pro Phe Ser Ala Gln Ser Gly Ala Gly Val
            165                 170                 175

Pro Gly Trp Gly Ile Ala Leu Leu Val Leu Val Cys Val Leu Val Ala
        180                 185                 190

Leu Ala Ile Val Tyr Leu Ile Ala Leu Ala Val Cys Gln Cys Arg Arg
            195                 200                 205

Lys Asn Tyr Gly Gln Leu Asp Ile Phe Pro Ala Arg Asp Thr Tyr His
    210                 215                 220

Pro Met Ser Glu Tyr Pro Thr Tyr His Thr His Gly Arg Tyr Val Pro
225                 230                 235                 240

Pro Ser Thr Asp Arg Ser Pro Tyr Glu Lys Val Ser Ala Gly Asn
            245                 250                 255

Gly Gly Ser Ser Leu Ser Tyr Thr Asn Pro Ala Val Ala Ala Ala Ser
            260                 265                 270

Ala Asn Leu
        275

<210> SEQ ID NO 8
<211> LENGTH: 233
<212> TYPE: PRT
<213> ORGANISM: Homo sapiens

<400> SEQUENCE: 8

Gly Ser Gly His Ala Ser Ser Thr Pro Gly Gly Glu Lys Glu Thr Ser
1               5                   10                  15

Ala Thr Gln Arg Ser Ser Val Pro Ser Ser Thr Glu Lys Asn Ala Phe
            20                  25                  30

Asn Ser Ser Leu Glu Asp Pro Ser Thr Asp Tyr Tyr Gln Glu Leu Gln
        35                  40                  45

Arg Asp Ile Ser Glu Met Phe Leu Gln Ile Tyr Lys Gln Gly Gly Phe
    50                  55                  60

Leu Gly Leu Ser Asn Ile Lys Phe Arg Pro Gly Ser Val Val Val Gln
65                  70                  75                  80

Leu Thr Leu Ala Phe Arg Glu Gly Thr Ile Asn Val His Asp Met Glu
                85                  90                  95

Thr Gln Phe Asn Gln Tyr Lys Thr Glu Ala Ala Ser Arg Tyr Asn Leu
            100                 105                 110

Thr Ile Ser Asp Val Ser Val Ser Asp Val Pro Phe Pro Phe Ser Ala
        115                 120                 125

Gln Ser Gly Ala Gly Val Pro Gly Trp Gly Ile Ala Leu Leu Val Leu
    130                 135                 140

Val Cys Val Leu Val Ala Leu Ala Ile Val Tyr Leu Ile Ala Leu Ala
145                 150                 155                 160

Val Cys Gln Cys Arg Arg Lys Asn Tyr Gly Gln Leu Asp Ile Phe Pro
                165                 170                 175

Ala Arg Asp Thr Tyr His Pro Met Ser Glu Tyr Pro Thr Tyr His Thr
            180                 185                 190

His Gly Arg Tyr Val Pro Pro Ser Thr Asp Arg Ser Pro Tyr Glu
        195                 200                 205

Lys Val Ser Ala Gly Asn Gly Ser Ser Leu Ser Tyr Thr Asn Pro
    210                 215                 220

Ala Val Ala Ala Thr Ser Ala Asn Leu
225                 230

<210> SEQ ID NO 9
```

<211> LENGTH: 863
<212> TYPE: PRT
<213> ORGANISM: Homo sapiens

<400> SEQUENCE: 9

```
Leu Asp Pro Arg Val Arg Thr Ser Ala Pro Asp Thr Arg Pro Ala Pro
1               5                   10                  15

Gly Ser Thr Ala Pro Gln Ala His Gly Val Thr Ser Ala Pro Asp Thr
            20                  25                  30

Arg Pro Ala Pro Gly Ser Thr Ala Pro Pro Ala His Gly Val Thr Ser
        35                  40                  45

Ala Pro Asp Thr Arg Pro Ala Pro Gly Ser Thr Ala Pro Pro Ala His
    50                  55                  60

Gly Val Thr Ser Ala Pro Asp Thr Arg Pro Ala Pro Gly Ser Thr Ala
65                  70                  75                  80

Pro Pro Ala His Gly Val Thr Ser Ala Pro Asp Thr Arg Pro Ala Pro
                85                  90                  95

Gly Ser Thr Ala Pro Pro Ala His Gly Val Thr Ser Ala Pro Asp Thr
            100                 105                 110

Arg Pro Ala Pro Gly Ser Thr Ala Pro Pro Ala His Gly Val Thr Ser
        115                 120                 125

Ala Pro Asp Thr Arg Pro Ala Pro Gly Ser Thr Ala Pro Pro Ala His
    130                 135                 140

Gly Val Thr Ser Ala Pro Asp Thr Arg Pro Ala Pro Gly Ser Thr Ala
145                 150                 155                 160

Pro Pro Ala His Gly Val Thr Ser Ala Pro Asp Thr Arg Pro Ala Pro
                165                 170                 175

Gly Ser Thr Ala Pro Pro Ala His Gly Val Thr Ser Ala Pro Asp Thr
            180                 185                 190

Arg Pro Ala Pro Gly Ser Thr Ala Pro Pro Ala His Gly Val Thr Ser
        195                 200                 205

Ala Pro Asp Thr Arg Pro Ala Pro Gly Ser Thr Ala Pro Pro Ala His
    210                 215                 220

Gly Val Thr Ser Ala Pro Asp Thr Arg Pro Ala Pro Gly Ser Thr Ala
225                 230                 235                 240

Pro Pro Ala His Gly Val Thr Ser Ala Pro Asp Thr Arg Pro Ala Pro
                245                 250                 255

Gly Ser Thr Ala Pro Pro Ala His Gly Val Thr Ser Ala Pro Asp Thr
            260                 265                 270

Arg Pro Ala Pro Gly Ser Thr Ala Pro Pro Ala His Gly Val Thr Ser
        275                 280                 285

Ala Pro Asp Thr Arg Pro Ala Pro Gly Ser Thr Ala Pro Pro Ala His
    290                 295                 300

Gly Val Thr Ser Ala Pro Asp Thr Arg Pro Ala Pro Gly Ser Thr Ala
305                 310                 315                 320

Pro Pro Ala His Gly Val Thr Ser Ala Pro Asp Thr Arg Pro Ala Pro
                325                 330                 335

Gly Ser Thr Ala Pro Pro Ala His Gly Val Thr Ser Ala Pro Asp Thr
            340                 345                 350

Arg Pro Ala Pro Gly Ser Thr Ala Pro Pro Ala His Gly Val Thr Ser
        355                 360                 365

Ala Pro Asp Thr Arg Pro Ala Pro Gly Ser Thr Ala Pro Pro Ala His
    370                 375                 380

Gly Val Thr Ser Ala Pro Asp Thr Arg Pro Ala Pro Gly Ser Thr Ala
```

```
            385                 390                 395                 400
Pro Pro Ala His Gly Val Thr Ser Ala Pro Asp Thr Arg Pro Ala Pro
                    405                 410                 415
Gly Ser Thr Ala Pro Pro Ala His Gly Val Thr Ser Ala Pro Asp Thr
                    420                 425                 430
Arg Pro Ala Pro Gly Ser Thr Ala Pro Pro Ala His Gly Val Thr Ser
                    435                 440                 445
Ala Pro Asp Thr Arg Pro Ala Pro Gly Ser Thr Ala Pro Pro Ala His
        450                 455                 460
Gly Val Thr Ser Ala Pro Asp Thr Arg Pro Ala Pro Gly Ser Thr Ala
465                 470                 475                 480
Pro Pro Ala His Gly Val Thr Ser Ala Pro Asp Thr Arg Pro Ala Pro
                    485                 490                 495
Gly Ser Thr Ala Pro Pro Ala His Gly Val Thr Ser Ala Pro Asp Thr
                    500                 505                 510
Arg Pro Ala Pro Gly Ser Thr Ala Pro Pro Ala His Gly Val Thr Ser
                    515                 520                 525
Ala Pro Asp Thr Arg Pro Ala Pro Gly Ser Thr Ala Pro Pro Ala His
        530                 535                 540
Gly Val Thr Ser Ala Pro Asp Asn Arg Pro Ala Leu Gly Ser Thr Ala
545                 550                 555                 560
Pro Pro Val His Asn Val Thr Ser Ala Ser Gly Ser Ala Ser Gly Ser
                    565                 570                 575
Ala Ser Thr Leu Val His Asn Gly Thr Ser Ala Arg Ala Thr Thr Thr
                    580                 585                 590
Pro Ala Ser Lys Ser Thr Pro Phe Ser Ile Pro Ser His His Ser Asp
                    595                 600                 605
Thr Pro Thr Thr Leu Ala Ser His Ser Thr Lys Thr Asp Ala Ser Ser
        610                 615                 620
Thr His His Ser Ser Val Pro Pro Leu Thr Ser Ser Asn His Ser Thr
625                 630                 635                 640
Ser Pro Gln Leu Ser Thr Gly Val Ser Phe Phe Leu Ser Phe His
                    645                 650                 655
Ile Ser Asn Leu Gln Phe Asn Ser Ser Leu Glu Asp Pro Ser Thr Asp
                    660                 665                 670
Tyr Tyr Gln Glu Leu Gln Arg Asp Ile Ser Glu Met Phe Leu Gln Ile
                    675                 680                 685
Tyr Lys Gln Gly Gly Phe Leu Gly Leu Ser Asn Ile Lys Phe Arg Pro
                    690                 695                 700
Gly Ser Val Val Val Gln Leu Thr Leu Ala Phe Arg Glu Gly Thr Ile
705                 710                 715                 720
Asn Val His Asp Val Glu Thr Gln Phe Asn Gln Tyr Lys Thr Glu Ala
                    725                 730                 735
Ala Ser Arg Tyr Asn Leu Thr Ile Ser Asp Val Ser Val Ser Asp Val
                    740                 745                 750
Pro Phe Pro Phe Ser Ala Gln Ser Gly Ala Gly Val Pro Gly Trp Gly
                    755                 760                 765
Ile Ala Leu Leu Val Leu Val Cys Val Leu Val Ala Leu Ala Ile Val
                    770                 775                 780
Tyr Leu Ile Ala Leu Ala Val Cys Gln Cys Arg Arg Lys Asn Tyr Gly
785                 790                 795                 800
Gln Leu Asp Ile Phe Pro Ala Arg Asp Thr Tyr His Pro Met Ser Glu
                    805                 810                 815
```

```
Tyr Pro Thr Tyr His Thr His Gly Arg Tyr Val Pro Ser Ser Thr
            820                 825                 830

Asp Arg Ser Pro Tyr Glu Lys Val Ser Ala Gly Asn Gly Ser Ser
        835                 840                 845

Leu Ser Tyr Thr Asn Pro Ala Val Ala Ala Ser Ala Asn Leu
    850                 855                 860

<210> SEQ ID NO 10
<211> LENGTH: 45
<212> TYPE: PRT
<213> ORGANISM: Homo sapiens

<400> SEQUENCE: 10

Gly Thr Ile Asn Val His Asp Val Glu Thr Gln Phe Asn Gln Tyr Lys
1               5                   10                  15

Thr Glu Ala Ala Ser Arg Tyr Asn Leu Thr Ile Ser Asp Val Ser Val
            20                  25                  30

Ser Asp Val Pro Phe Pro Phe Ser Ala Gln Ser Gly Ala
        35                  40                  45

<210> SEQ ID NO 11
<211> LENGTH: 44
<212> TYPE: PRT
<213> ORGANISM: Homo sapiens

<400> SEQUENCE: 11

Thr Ile Asn Val His Asp Val Glu Thr Gln Phe Asn Gln Tyr Lys Thr
1               5                   10                  15

Glu Ala Ala Ser Arg Tyr Asn Leu Thr Ile Ser Asp Val Ser Val Ser
            20                  25                  30

Asp Val Pro Phe Pro Phe Ser Ala Gln Ser Gly Ala
        35                  40

<210> SEQ ID NO 12
<211> LENGTH: 45
<212> TYPE: PRT
<213> ORGANISM: Homo sapiens

<400> SEQUENCE: 12

Gly Thr Ile Asn Val His Asp Val Glu Thr Gln Phe Asn Gln Tyr Lys
1               5                   10                  15

Thr Glu Ala Ala Ser Pro Tyr Asn Leu Thr Ile Ser Asp Val Ser Val
            20                  25                  30

Ser Asp Val Pro Phe Pro Phe Ser Ala Gln Ser Gly Ala
        35                  40                  45

<210> SEQ ID NO 13
<211> LENGTH: 44
<212> TYPE: PRT
<213> ORGANISM: Homo sapiens

<400> SEQUENCE: 13

Thr Ile Asn Val His Asp Val Glu Thr Gln Phe Asn Gln Tyr Lys Thr
1               5                   10                  15

Glu Ala Ala Ser Pro Tyr Asn Leu Thr Ile Ser Asp Val Ser Val Ser
            20                  25                  30

Asp Val Pro Phe Pro Phe Ser Ala Gln Ser Gly Ala
        35                  40
```

```
<210> SEQ ID NO 14
<211> LENGTH: 33
<212> TYPE: PRT
<213> ORGANISM: Homo sapiens

<400> SEQUENCE: 14

Gly Thr Ile Asn Val His Asp Val Glu Thr Gln Phe Asn Gln Tyr Lys
1               5                   10                  15

Thr Glu Ala Ala Ser Pro Tyr Asn Leu Thr Ile Ser Asp Val Ser Val
            20                  25                  30

Ser

<210> SEQ ID NO 15
<211> LENGTH: 48
<212> TYPE: PRT
<213> ORGANISM: Homo sapiens

<400> SEQUENCE: 15

Val Gln Leu Thr Leu Ala Phe Arg Glu Gly Thr Ile Asn Val His Asp
1               5                   10                  15

Val Glu Thr Gln Phe Asn Gln Tyr Lys Thr Glu Ala Ala Ser Pro Tyr
            20                  25                  30

Asn Leu Thr Ile Ser Asp Val Ser Val Ser Asp Val Pro Phe Pro Phe
        35                  40                  45

<210> SEQ ID NO 16
<211> LENGTH: 57
<212> TYPE: PRT
<213> ORGANISM: Homo sapiens

<400> SEQUENCE: 16

Ser Val Val Val Gln Leu Thr Leu Ala Phe Arg Glu Gly Thr Ile Asn
1               5                   10                  15

Val His Asp Val Glu Thr Gln Phe Asn Gln Tyr Lys Thr Glu Ala Ala
            20                  25                  30

Ser Pro Tyr Asn Leu Thr Ile Ser Asp Val Ser Val Ser Asp Val Pro
        35                  40                  45

Phe Pro Phe Ser Ala Gln Ser Gly Ala
    50                  55

<210> SEQ ID NO 17
<211> LENGTH: 25
<212> TYPE: PRT
<213> ORGANISM: Homo sapiens

<400> SEQUENCE: 17

Gly Phe Leu Gly Leu Ser Asn Ile Lys Phe Arg Pro Gly Ser Val Val
1               5                   10                  15

Val Gln Leu Thr Leu Ala Phe Arg Glu
            20                  25

<210> SEQ ID NO 18
<211> LENGTH: 13
<212> TYPE: PRT
<213> ORGANISM: Homo sapiens

<400> SEQUENCE: 18

Ser Val Val Val Gln Leu Thr Leu Ala Phe Arg Glu Gly
1               5                   10

<210> SEQ ID NO 19
```

```
<211> LENGTH: 40
<212> TYPE: PRT
<213> ORGANISM: Homo sapiens

<400> SEQUENCE: 19

Pro Asp Thr Arg Pro Ala Pro Gly Ser Thr Ala Pro Pro Ala His Gly
1               5                   10                  15

Val Thr Ser Ala Pro Asp Thr Arg Pro Ala Pro Gly Ser Thr Ala Pro
            20                  25                  30

Pro Ala His Gly Val Thr Ser Ala
        35                  40

<210> SEQ ID NO 20
<211> LENGTH: 4003
<212> TYPE: DNA
<213> ORGANISM: Homo sapiens

<400> SEQUENCE: 20
acaggttctg gtcatgcaag ctctacccca ggtggagaaa aggagacttc ggctacccag      60
agaagttcag tgcccagctc tactgagaag aatgctgtga gtatgaccag cagcgtactc     120
tccagccaca gccccggttc aggctcctcc accactcagg acaggatgt cactctggcc      180 ccggccacgg aaccagcttc aggttcagct gccacctggg gacaggatgt cacctcggtc     240
ccagtcacca ggccagccct gggctccacc acccgccag cccacgatgt cacctcagcc      300
ccggacaaca agccagcccc gggctccacc gccccccag cccacggtgt cacctcggcc      360
ccggacacca ggccggcccc gggctccacc gccccccag cccacggtgt cacctcggcc      420
ccggacacca ggccggcccc gggctccacc gccccccag cccacggtgt cacctcggcc      480
ccggacacca ggccggcccc gggctccacc gccccccag cccacggtgt cacctcggcc      540
ccggacacca ggccggcccc gggctccacc gccccccag cccacggtgt cacctcggcc      600
ccggacacca ggccggcccc gggctccacc gccccccag cccacggtgt cacctcggcc      660
ccggacacca ggccggcccc gggctccacc gccccccag cccacggtgt cacctcggcc      720
ccggacacca ggccggcccc gggctccacc gccccccag cccacggtgt cacctcggcc      780
ccggacacca ggccggcccc gggctccacc gccccccag cccacggtgt cacctcggcc      840
ccggacacca ggccggcccc gggctccacc gccccccag cccacggtgt cacctcggcc      900
ccggacacca ggccggcccc gggctccacc gccccccag cccacggtgt cacctcggcc      960
ccggacacca ggccggcccc gggctccacc gccccccag cccacggtgt cacctcggcc     1020
ccggacacca ggccggcccc gggctccacc gccccccag cccacggtgt cacctcggcc     1080
ccggacacca ggccggcccc gggctccacc gccccccag cccacggtgt cacctcggcc     1140
ccggacacca ggccggcccc gggctccacc gccccccag cccacggtgt cacctcggcc     1200
ccggacacca ggccggcccc gggctccacc gccccccag cccacggtgt cacctcggcc     1260
ccggacacca ggccggcccc gggctccacc gccccccag cccacggtgt cacctcggcc     1320
ccggacacca ggccggcccc gggctccacc gccccccag cccacggtgt cacctcggcc     1380
ccggacacca ggccggcccc gggctccacc gccccccag cccacggtgt cacctcggcc     1440
ccggacacca ggccggcccc gggctccacc gccccccag cccacggtgt cacctcggcc     1500
ccggacacca ggccggcccc gggctccacc gccccccag cccacggtgt cacctcggcc     1560
ccggacacca ggccggcccc gggctccacc gccccccag cccacggtgt cacctcggcc     1620
ccggacacca ggccggcccc gggctccacc gccccccag cccacggtgt cacctcggcc     1680
```

```
ccggacacca ggccggcccc gggctccacc gcccccccag cccacggtgt cacctcggcc    1740
ccggacacca ggccggcccc gggctccacc gcccccccag cccacggtgt cacctcggcc    1800
ccggacacca ggccggcccc gggctccacc gcccccccag cccacggtgt cacctcggcc    1860
ccggacacca ggccggcccc gggctccacc gcccccccag cccacggtgt cacctcggcc    1920
ccggacacca ggccggcccc gggctccacc gcccccccag cccacggtgt cacctcggcc    1980
ccggacacca ggccggcccc gggctccacc gcccccccag cccacggtgt cacctcggcc    2040
ccggacacca ggccggcccc gggctccacc gcccccccag cccacggtgt cacctcggcc    2100
ccggacacca ggccggcccc gggctccacc gcccccccag cccacggtgt cacctcggcc    2160
ccggacacca ggccggcccc gggctccacc gcccccccag cccacggtgt cacctcggcc    2220
ccggacacca ggccggcccc gggctccacc gcccccccag cccacggtgt cacctcggcc    2280
ccggacacca ggccggcccc gggctccacc gcccccccag cccacggtgt cacctcggcc    2340
ccggacacca ggccggcccc gggctccacc gcccccccag cccacggtgt cacctcggcc    2400
ccggacacca ggccggcccc gggctccacc gcccccccag cccacggtgt cacctcggcc    2460
ccggacacca ggccggcccc gggctccacc gcccccccag cccacggtgt cacctcggcc    2520
ccggacacca ggccggcccc gggctccacc gcccccccag cccacggtgt cacctcggcc    2580
ccggacacca ggccggcccc gggctccacc gcccccccag cccacggtgt cacctcggcc    2640
ccggacacca ggccggcccc gggctccacc gcccccccag cccacggtgt cacctcggcc    2700
ccggacacca ggccggcccc gggctccacc gcccccccag cccacggtgt cacctcggcc    2760
ccggacaaca ggcccgcctt gggctccacc gcccctccag tccacaatgt cacctcggcc    2820
tcaggctctg catcaggctc agcttctact ctggtgcaca acggcacctc tgccagggct    2880
accacaaccc cagccagcaa gagcactcca ttctcaattc ccagccacca ctctgatact    2940
cctaccaccc ttgccagcca tagcaccaag actgatgcca gtagcactca ccatagctcg    3000
gtacctcctc tcacctcctc caatcacagc acttctcccc agttgtctac tggggtctct    3060
ttctttttcc tgtcttttca catttcaaac ctccagttta attcctctct ggaagatccc    3120
agcaccgact actaccaaga gctgcagaga gacatttctg aaatgttttt gcagatttat    3180
aaacaagggg gttttctggg cctctccaat attaagttca ggccaggatc tgtggtggta    3240
caattgactc tggccttccg agaaggtacc atcaatgtcc acgacgtgga gacacagttc    3300
aatcagtata aaacggaagc agcctctcga tataacctga cgatctcaga cgtcagcgtg    3360
agtgatgtgc catttccttt ctctgcccag tctggggctg gggtgccagg ctggggcatc    3420
gcgctgctgg tgctggtctg tgttctggtt gcgctggcca ttgtctatct cattgccttg    3480
gctgtctgtc agtgccgccg aaagaactac gggcagctgg acatctttcc agccggggat    3540
acctaccatc ctatgagcga gtaccccacc taccacaccc atgggcgcta tgtgcccct    3600
agcagtaccg atcgtagccc ctatgagaag gtttctgcag gtaacggtgg cagcagcctc    3660
tcttacacaa acccagcagt ggcagccgct tctgccaact gtagggcac gtcgccgctg    3720
agctgagtgg ccagccagtg ccattccact ccactcaggt tcttcaggcc agagccctg    3780
caccctgttt gggctggtga gctgggagtt caggtgggct gctcacagcc tccttcagag    3840
gccccaccaa tttctcggac acttctcagt gtgtggaagc tcatgtgggc ccctgaggct    3900
catgcctggg aagtgttgtg ggggctccca ggaggactgg cccagagagc cctgagatag    3960
cggggatcct gaactggact gaataaaacg tggtctccca ctg                      4003
```

<210> SEQ ID NO 21
<211> LENGTH: 751
<212> TYPE: DNA
<213> ORGANISM: Homo sapiens

<400> SEQUENCE: 21

```
acgggcacgg ccggtaccat caatgtccac gacgtggaga cacagttcaa tcagtataaa    60
acggaagcag cctctcgata taacctgacg atctcagacg tcagcgtgag tgatgtgcca   120
tttcctttct ctgcccagtc tggggctggg gtgccaggct ggggcatcgc gctgctggtg   180
ctggtctgtg ttctggttgc gctggccatt gtctatctca ttgccttggc tgtctgtcag   240
tgccgccgaa agaactacgg gcagctggac atctttccag cccgggatac ctaccatcct   300
atgagcgagt accccaccta ccacacccat gggcgctatg tgcccctag cagtaccgat   360
cgtagcccct atgagaaggt ttctgcaggt aacggtggca gcagcctctc ttacacaaac   420
ccagcagtgg cagccgcttc tgccaacttg tagggcacgt cgccgctgag ctgagtggcc   480
agccagtgcc attccactcc actcaggttc ttcaggccag agcccctgca ccctgtttgg   540
gctggtgagc tgggagttca ggtgggctgc tcacagcctc cttcagaggc cccaccaatt   600
tctcggacac ttctcagtgt gtggaagctc atgtgggccc ctgaggctca tgcctgggaa   660
gtgttgtggg ggctcccagg aggactggcc cagagagccc tgagatagcg gggatcctga   720
actggactga ataaaacgtg gtctcccact g                                  751
```

<210> SEQ ID NO 22
<211> LENGTH: 820
<212> TYPE: PRT
<213> ORGANISM: Homo sapiens

<400> SEQUENCE: 22

```
Ala Cys Gly Gly Cys Cys Gly Gly Thr Thr Thr Cys Thr Gly Gly
 1               5                  10                  15

Gly Cys Cys Thr Cys Thr Cys Cys Ala Ala Thr Ala Thr Ala Ala
                20                  25                  30

Gly Thr Thr Cys Ala Gly Gly Cys Cys Ala Gly Gly Ala Thr Cys Thr
            35                  40                  45

Gly Thr Gly Gly Thr Gly Gly Thr Ala Cys Ala Ala Thr Thr Gly Ala
        50                  55                  60

Cys Thr Cys Thr Gly Gly Cys Cys Thr Thr Cys Cys Gly Ala Gly Ala
65                  70                  75                  80

Ala Gly Gly Thr Ala Cys Cys Ala Thr Cys Ala Ala Thr Gly Thr Cys
                85                  90                  95

Cys Ala Cys Gly Ala Cys Gly Thr Gly Gly Ala Gly Ala Cys Ala Cys
               100                 105                 110

Ala Gly Thr Thr Cys Ala Ala Thr Cys Ala Gly Thr Ala Thr Ala Ala
           115                 120                 125

Ala Ala Cys Gly Gly Ala Ala Gly Cys Ala Gly Cys Cys Thr Cys Thr
       130                 135                 140

Cys Gly Ala Thr Ala Thr Ala Ala Cys Cys Thr Gly Ala Cys Gly Ala
145                 150                 155                 160

Thr Cys Thr Cys Ala Gly Ala Cys Gly Thr Cys Ala Gly Cys Gly Thr
               165                 170                 175

Gly Ala Gly Thr Gly Ala Thr Gly Thr Gly Cys Cys Ala Thr Thr Thr
           180                 185                 190

Cys Cys Thr Thr Thr Cys Thr Cys Thr Gly Cys Cys Cys Ala Gly Thr
       195                 200                 205
```

```
Cys Thr Gly Gly Gly Gly Cys Thr Gly Gly Gly Gly Thr Gly Cys Cys
    210                 215                 220

Ala Gly Gly Cys Thr Gly Gly Gly Gly Cys Ala Thr Cys Gly Cys Gly
225                 230                 235                 240

Cys Thr Gly Cys Thr Gly Gly Thr Gly Cys Thr Gly Gly Thr Cys Thr
                245                 250                 255

Gly Thr Gly Thr Thr Cys Thr Gly Gly Thr Thr Gly Cys Gly Cys Thr
            260                 265                 270

Gly Gly Cys Cys Ala Thr Thr Gly Thr Cys Thr Ala Thr Cys Thr Cys
        275                 280                 285

Ala Thr Thr Gly Cys Cys Thr Thr Gly Gly Cys Thr Gly Thr Cys Thr
    290                 295                 300

Gly Thr Cys Ala Gly Thr Gly Cys Cys Gly Cys Cys Gly Ala Ala Ala
305                 310                 315                 320

Gly Ala Ala Cys Thr Ala Cys Gly Gly Gly Cys Ala Gly Cys Thr Gly
                325                 330                 335

Gly Ala Cys Ala Thr Cys Thr Thr Thr Cys Cys Ala Gly Cys Cys Cys
            340                 345                 350

Gly Gly Gly Ala Thr Ala Cys Cys Thr Ala Cys Cys Ala Thr Cys Cys
        355                 360                 365

Thr Ala Thr Gly Ala Gly Cys Gly Ala Gly Thr Ala Cys Cys Cys Cys
    370                 375                 380

Ala Cys Cys Thr Ala Cys Cys Ala Cys Ala Cys Cys Cys Ala Thr Gly
385                 390                 395                 400

Gly Gly Cys Gly Cys Thr Ala Thr Gly Thr Gly Cys Cys Cys Cys Cys
                405                 410                 415

Thr Ala Gly Cys Ala Gly Thr Ala Cys Cys Gly Ala Thr Cys Gly Thr
            420                 425                 430

Ala Gly Cys Cys Cys Cys Thr Ala Thr Gly Ala Gly Ala Ala Gly Gly
        435                 440                 445

Thr Thr Thr Cys Thr Gly Cys Ala Gly Gly Thr Ala Ala Cys Gly Gly
    450                 455                 460

Thr Gly Gly Cys Ala Gly Cys Ala Gly Cys Cys Thr Cys Thr Cys Thr
465                 470                 475                 480

Thr Ala Cys Ala Cys Ala Ala Ala Cys Cys Cys Ala Gly Cys Ala Gly
                485                 490                 495

Thr Gly Gly Cys Ala Gly Cys Cys Gly Cys Thr Thr Cys Thr Gly Cys
            500                 505                 510

Cys Ala Ala Cys Thr Thr Gly Thr Ala Gly Gly Gly Cys Ala Cys Gly
        515                 520                 525

Thr Cys Gly Cys Cys Gly Cys Thr Gly Ala Gly Cys Thr Gly Ala Gly
    530                 535                 540

Thr Gly Gly Cys Cys Ala Gly Cys Cys Ala Gly Thr Gly Cys Cys Ala
545                 550                 555                 560

Thr Thr Cys Cys Ala Cys Thr Cys Cys Ala Cys Thr Cys Ala Gly Gly
                565                 570                 575

Thr Thr Cys Thr Thr Cys Ala Gly Gly Cys Cys Ala Gly Ala Gly Cys
            580                 585                 590

Cys Cys Cys Thr Gly Cys Ala Cys Cys Cys Thr Gly Thr Thr Thr Gly
        595                 600                 605

Gly Gly Cys Thr Gly Gly Thr Gly Ala Gly Cys Thr Gly Gly Gly Ala
    610                 615                 620
```

```
Gly Thr Thr Cys Ala Gly Gly Thr Gly Gly Cys Thr Gly Cys Thr
625                 630                 635                 640
Cys Ala Cys Ala Gly Cys Cys Thr Cys Cys Thr Thr Cys Ala Gly Ala
                645                 650                 655
Gly Gly Cys Cys Cys Ala Cys Cys Ala Ala Thr Thr Thr Cys Thr
            660                 665                 670
Cys Gly Gly Ala Cys Ala Cys Thr Thr Cys Thr Cys Ala Gly Thr Gly
            675                 680                 685
Thr Gly Thr Gly Gly Ala Ala Gly Cys Thr Cys Ala Thr Gly Thr Gly
690                 695                 700
Gly Gly Cys Cys Cys Thr Gly Ala Gly Gly Cys Thr Cys Ala Thr
705                 710                 715                 720
Gly Cys Cys Thr Gly Gly Ala Ala Gly Thr Gly Thr Thr Gly Thr
            725                 730                 735
Gly Gly Gly Gly Gly Cys Thr Cys Cys Cys Ala Gly Gly Ala Gly Gly
            740                 745                 750
Ala Cys Thr Gly Gly Cys Cys Cys Ala Gly Ala Gly Gly Cys Cys
            755                 760                 765
Cys Thr Gly Ala Gly Ala Thr Ala Gly Cys Gly Gly Gly Gly Ala Thr
770                 775                 780
Cys Cys Thr Gly Ala Ala Cys Thr Gly Gly Ala Cys Thr Gly Ala Ala
785                 790                 795                 800
Thr Ala Ala Ala Cys Gly Thr Gly Gly Thr Cys Thr Cys Cys Cys
                805                 810                 815
Ala Cys Thr Gly
            820

<210> SEQ ID NO 23
<211> LENGTH: 1132
<212> TYPE: DNA
<213> ORGANISM: Homo sapiens

<400> SEQUENCE: 23
acggccgcta ccacaacccc agccagcaag agcactccat tctcaattcc cagccaccac      60
tctgatactc ctaccaccct tgccagccat agcaccaaga ctgatgccag tagcactcac     120
catagctcgg tacctcctct cacctcctcc aatcacagca cttctcccca gttgtctact     180
ggggtctctt tcttttttcct gtcttttcac atttcaaacc tccagtttaa ttcctctctg    240
gaagatccca gcaccgacta ctaccaagag ctgcagagag acatttctga aatgttttg     300 cagatttata acaaggggg ttttctgggc ctctccaata ttaagttcag gccaggatct     360
gtggtggtac aattgactct ggccttccga gaaggtacca tcaatgtcca cgacgtggag     420
acacagttca atcagtataa aacggaagca gcctctcgat ataacctgac gatctcagac    480
gtcagcgtga gtgatgtgcc atttcctttc tctgcccagt ctgggctgg ggtgccaggc     540 tggggcatcg cgctgctggt gctggtctgt gttctggttg cgctggccat tgtctatctc    600
attgccttgg ctgtctgtca gtgccgccga aagaactacg gcagctgga catctttcca    660 gcccgggata cctaccatcc tatgagcgag tacccccacct accacaccca tgggcgctat    720
gtgcccccta gcagtaccga tcgtagcccc atgagaaagg tttctgcagg taacggtggc    780
agcagcctct cttacacaaa cccagcagtg gcagccgctt ctgccaactt gtagggcacg    840
tcgccgctga gctgagtggc cagcagtgc cattccactc cactcaggtt cttcaggcca    900
gagcccctgc accctgtttg ggctggtgag ctggagttc aggtgggctg ctcacagcct    960
```

```
ccttcagagg ccccaccaat ttctcggaca cttctcagtg tgtggaagct catgtgggcc      1020
cctgaggctc atgcctggga agtgttgtgg gggctcccag gaggactggc ccagagagcc      1080
ctgagatagc ggggatcctg aactggactg aataaaacgt ggtctcccac tg              1132

<210> SEQ ID NO 24
<211> LENGTH: 717
<212> TYPE: DNA
<213> ORGANISM: Homo sapiens

<400> SEQUENCE: 24
acaggttctg gtcatgcaag ctctacccca ggtggagaaa aggagacttc ggctacccag        60
agaagttcag tgcccagctc tactgagaag aatgctttta attcctctct ggaagatccc       120
agcaccgact actaccaaga gctgcagaga gacatttctg aaatgttttt gcagatttat       180
aaacaagggg gttttctggg cctctccaat attaagttca ggccaggatc tgtggtggta       240
caattgactc tggccttccg agaaggtacc atcaatgtcc acgacgtgga gacacagttc       300
aatcagtata aaacggaagc agcctctcga tataacctga cgatctcaga cgtcagcgtg       360
agtgatgtgc catttccttt ctctgcccag tctggggctg gggtgccagg ctggggcatc       420
gcgctgctgg tgctggtctg tgttctggtt gcgctggcca ttgtctatct cattgccttg       480
gctgtctgtc agtgccgccg aaagaactac gggcagctgg acatctttcc agcccgggat       540
acctaccatc ctatgagcga gtaccccacc taccacaccc atgggcgcta tgtgcccct        600 agcagtaccg atcgtagccc ctatgagaag gtttctgcag gtaatggtgg cagcagcctc       660
tcttacacaa acccagcagt ggcagccact tctgccaact tgtaggggca cgtcgcc         717

<210> SEQ ID NO 25
<211> LENGTH: 2487
<212> TYPE: DNA
<213> ORGANISM: Homo sapiens

<400> SEQUENCE: 25
ctcgacccac gcgtccgctc gacccacgcg tccgcacctc ggccccggac accaggccgg        60
ccccgggctc caccgccccc ccagcccacg gtgtcacctc ggccccggac accaggccgg       120
ccccgggctc caccgccccc ccagcccacg gtgtcacctc ggccccggac accaggccgg       180
ccccgggctc caccgccccc ccagcccacg gtgtcacctc ggccccggac accaggccgg       240
ccccgggctc caccgccccc ccagcccacg gtgtcacctc ggccccggac accaggccgg       300
ccccgggctc caccgccccc ccagcccacg gtgtcacctc ggccccggac accaggccgg       360
ccccgggctc caccgccccc ccagcccacg gtgtcacctc ggccccggac accaggccgg       420
ccccgggctc caccgccccc ccagcccacg gtgtcacctc ggccccggac accaggccgg       480
ccccgggctc caccgccccc ccagcccacg gtgtcacctc ggccccggac accaggccgg       540
ccccgggctc caccgccccc ccagcccacg gtgtcacctc ggccccggac accaggccgg       600
ccccgggctc caccgccccc ccagcccacg gtgtcacctc ggccccggac accaggccgg       660
ccccgggctc caccgccccc ccagcccacg gtgtcacctc ggccccggac accaggccgg       720
ccccgggctc caccgccccc ccagcccacg gtgtcacctc ggccccggac accaggccgg       780
ccccgggctc caccgccccc ccagcccacg gtgtcacctc ggccccggac accaggccgg       840
ccccgggctc caccgccccc ccagcccacg gtgtcacctc ggccccggac accaggccgg       900
ccccgggctc caccgccccc ccagcccacg gtgtcacctc ggccccggac accaggccgg       960
ccccgggctc caccgccccc ccagcccacg gtgtcacctc ggccccggac accaggccgg      1020
```

```
cccegggctc caccgccccc ccagcccacg gtgtcacctc ggccccggac accaggccgg    1080 cccegggctc caccgccccc ccagcccacg gtgtcacctc ggccccggac accaggccgg    1140 cccegggctc caccgccccc ccagcccacg gtgtcacctc ggccccggac accaggccgg    1200 cccegggctc caccgccccc ccagcccatg gtgtcacctc ggccccggac aacaggcccg    1260
ccttgggctc caccgccccct ccagtccaca atgtcacctc ggcctcaggc tctgcatcag   1320
gctcagcttc tactctggtg cacaacggca cctctgccag ggctaccaca accccagcca   1380
gcaagagcac tccattctca attcccagcc accactctga tactcctacc acccttgcca   1440
gccatagcac caagactgat gccagtagca ctcaccatag ctcggtacct cctctcacct   1500
cctccaatca cagcacttct ccccagttgt ctactggggt ctctttcttt ttcctgtctt   1560
ttcacatttc aaacctccag tttaattcct ctctggaaga tcccagcacc gactactacc   1620
aagagctgca gagagacatt tctgaaatgt ttttgcagat ttataaacaa ggggttttc    1680 tgggcctctc caatattaag ttcaggccag gatctgtggt ggtacaattg actctggcct   1740
tccgagaagg taccatcaat gtccacgacg tggagacaca gttcaatcag tataaaacgg   1800
aagcagcctc tcgatataac ctgacgatct cagacgtcag cgtgagtgat gtgccatttc   1860
ctttctctgc ccagtctggg gctggggtgc caggctgggg catcgcgctg ctggtgctgg   1920
tctgtgttct ggttgcgctg gccattgtct atctcattgc cttggctgtc tgtcagtgcc   1980
gccgaaagaa ctacgggcag ctggacatct ttccagcccg ggatacctac catcctatga   2040
gcgagtaccc cacctaccac acccatgggc gctatgtgcc ccctagcagt accgatcgta   2100 gccccctatga gaaggtttct gcaggtaacg gtggcagcag cctctcttac acaaacccag   2160
cagtggcagc cgcttctgcc aacttgtagg gcacgtcgcc gctgagctga gtggccagcc   2220
agtgccattc cactccactc aggttcttca ggccagagcc cctgcaccct gtttgggctg   2280
gtgagctggg agttcaggtg ggctgctcac agcctccttc agaggcccca ccaatttctc   2340
ggacacttct cagtgtgtgg aagctcatgt gggccctga ggctcatgcc tgggaagtgt    2400
tgtgggggct cccaggagga ctggcccaga gagccctgag atagcgggga tcctgaactg   2460
gactgaataa aacgtggtct cccactg                                       2487
```

METHODS FOR STIMULATING OR ENHANCING PROLIFERATION OF NON-TUMOROUS CELLS EXPRESSING MUC1 RECEPTORS

CROSS-REFERENCE TO RELATED APPLICATIONS

The present application claims the benefit of priority to U.S. Provisional Application No. 60/667,216, filed Mar. 30, 2005. The present application also claims the benefit of priority to PCT Application No. PCT/US2005/032821, filed Sep. 14, 2005, the contents of which are incorporated by reference herein in their entirety.

BACKGROUND OF THE INVENTION

1. Field of the Invention

The invention relates to a method for expanding a population of MUC1 expressing cells.

2. General Background and State of the Art

The following documents are incorporated herein by reference: PCT Application No. PCT/US2004/027954 (WO 2005/019269), filed Aug. 26, 2004; PCT Publication No. WO 02/056022, published Jul. 18, 2002; U.S. patent application Ser. No. 09/996,069, filed Nov. 27, 2001, published as Publication No. 2003/0036199 on Feb. 20, 2003, which describe the role of MUC1 receptor in tumorigenesis.

Recent research supports the existence of cancer stem cells (CSCs) (Prospective identification of tumorigenic stem cells. Al-Hajj M, Wicha M S, Benito-Hemandez A, Morrison S J and Clarke M F. (2003). Proc. Natl. Acad. Sci. USA, 100, 3983-3988; Characterization of clonogenic multiple myeloma cells. Matsui W, Huff C A, Wang Q, Malehorn M T, Barber J, Tanhehco Y, Smith B D, Civin C I and Jones R J. (2004) Blood, 103, 2332-2336; Identification of a cancer stem cell in human brain tumor. Singh S K, Clarke I D, Terasaki M, Bonn V E, Hawkins C, Squire J and Dirks P B. (2003) Cancer Res., 63, 5281-5828). Normal stem cells are characterized by their ability to self-renew indefinitely and to differentiate to become adult cells of distinct tissue types. Progenitor cells have the ability to further differentiate into distinct cell types but have lost the ability to differentiate into any type of cell. It has been shown that not all cancer cells have the ability to self-renew, to induce disease in a new host, or to form new tumors (A cell initiating human acute myeloid leukaemia after transplantation into SCID mice. Lapidot T, Srirad C, Vormoor J, Murdoch B, Hoang T, Caceres-Cortes J, Minden M, Paterson B, Caligiuri M and Dick J. (1994). Nature, 17, 645-648; Identification of a cancer stem cell in human brain tumor. Singh S K, Clarke I D, Terasaki M, Bonn V E, Hawkins C, Squire J and Dirks P B. (2003) Cancer Res., 63, 5281-5828; Human acute myeloid leukemia is organized as a hierarchy that originates from a primitive hematopoietic cell. Bonnet D., and Dick J E. (1997) Nat. Med. 3, 730-737). Rather, only a small fraction of cancer cells have this ability to self-renew and form new tumors, i.e. metastasize. A leading theory is that cancer is caused by normal stem cells whose tightly regulated system of checks and balances has broken down (Self-renewal and solid tumor stem cells. Al-Hajj M and Clarke M F. (2004) Oncogene, 23, 7274-7282). Solid tumors occur in organs that have stem cell populations. Epithelial cancers, which include breast, prostate, colon, and lung cancers are the most common cancers in adults. Over 75% of these cancers are characterized by the aberrant expression of the MUC1 receptor (Development and characterization of breast cancer reactive monoclonal antibodies directed to the core protein of the human milk mucin. Burchell J, Gendler S, Taylor-Papadimitriou J, Girling A, Lewis A, Millis R, and Lamport D. (1987) Cancer Res., 47, 5476-5482; Monoclonal antibodies to epithelial sialomucins recognize epitopes at different cellular sites in adenolymphomas of the parotid gland. Zotter S, Hageman P C, Lossnitzer A, Mooi W and Hilgers J. (1988) Cancer Rev. 11-12, 55-101; Mucins and mucin binding proteins in colorectal cancer. Byrd J C and Bresalier R S. (2004) Cancer Metastasis Review January-June; 23(1-2):77-99.), wherein aberrant expression means that the receptor is no longer localized to the apical border of luminal cells but rather is uniformly distributed over the entire cell surface (Differential reactivity of a novel monoclonal antibody (DF3) with human malignant versus benign breast tumors. (1984) Kufe D, Inghirami G, Abe, M, Hayes D, Justi-wheeler H and Schlom J. Hybridoma, 3, 223-232). The greatest percentage of MUC1-positive cancers is in breast cancers where greater than 96% show aberrant MUC1 expression. Interestingly, in the adult female, breast tissue must undergo cyclic bursts of growth and apoptosis with each menstrual period and pregnancy. Thus it follows that breast tissue must maintain functional stem cell or at least progenitor cell populations throughout adult female life.

The identification of the growth factors and their receptors that drive the growth of cancer stem cells could provide the key to understanding how to grow and manipulate stem cells and progenitor cells for research, therapeutic and other uses.

MUC1 (mucin 1) is a transmembrane mucin glycoprotein that is expressed on a number of epithelial cell types (Molecular cloning and expression of the human tumor associated polymorphic epithelial mucin, PEM. Gendler Sj, Lancaster C A, Taylor-Papadimitriou J, Dhuig, T, Peat, N, Burchell, J, Pemberton, L, Lalani, E-N and Wilson D. (1990) J. Biol. Chem. 265, 15286-15293; Episialin, a carcinoma associated mucin, is generated by a polymorphic gene encoding splice variants with alternative amino termini. Ligtenberg M J L, Vos H L, Genissen, A M C and Hilkens J. (1990) J. Biol. Chem. 265, 15573-15578), on haematopoietic cells (Evaluation of MUC1 and EGP40 in Bone marrow and Peripheral Blood as a Marker for Occult breast cancer. (2001). Zhong X Y, Kaul S, Bastert G, Arch Gynecol Obstet 264:177-181), and on progenitor cells as well (Epithelial Progenitors in the Normal Human mammary Gland. Stingl J, Raouf A, Emerman J, and Eaves C. (2005). Journal of Mammary Gland Biology and Neoplasia, Vol. 10, No. 1, 49-59). The cell surface receptor MUC1 is present at the apical border of healthy epithelium, but is aberrantly expressed (spread over the entire cell surface) in a wide range of human solid tumors. It has been known for some time that the MUC1 receptor can be cleaved or "shed" from the cell surface. The MUC1 ectodomain is actually comprised of three distinct regions: 1) the tandem repeats; 2) an interchain binding region that self-aggregates; and 3) the portion of the receptor that remains attached to the cell surface following proteolysis, called PSMGFR herein. The portion of the MUC1 receptor that remains attached to the cell surface after cleavage, consisting primarily of PSMGFR, is the major growth factor receptor that mediates the growth of MUC1-positive cancer cells in vitro. Transfection of a mutant MUC1 receptor comprised of the intact transmembrane and cytoplasmic domains, but having an ectodomain that terminates at the end of the PSMGFR sequence, which has been shown to be a natural cleavage site that occurs on cancer cells, is sufficient to confer the ability of these cells to grow anchorage-independently—the test for transformation to a neoplastic state. This cleaved form of MUC1 is the predominant form of the MUC1 receptor on human cancerous tissue specimens.

In further detail, MUC1 comprises several regions termed herein as follows, recited in an order starting from the region closest to the cell surface and progressing away from the cell. The basic structure of the MUC1 receptor is illustrated in FIG. 1. The receptor, as illustrated comprises: 1) cytoplasmic tail; 2) transmembrane section; 3) MGFR; 4) IBR, 5) Unique Region, 6) repeats, and N-terminus region comprising a signal peptide. For a detailed description of MUC1 and its function in normal and tumor cells, see PCT/US2005/032821, which is incorporated by reference herein, in its entirety for its description of the function and activity of cleaved MUC1 on the cell surface.

SUMMARY OF THE INVENTION

In one aspect, the present invention is directed to a method for stimulating or enhancing proliferation of a population of cells by activating MUC1 receptor on the cells. The activating may be carried out by contacting the cells with (i) an agent that multimerizes the MGFR portion of MUC1; (ii) an agent that increases the cleavage of MUC1 to the growth factor receptor form; or (iii) a ligand that activates the MGFR portion of the MUC1 receptor. The cells may be non-tumorous cells, preferably immature cells, such as stem cells, progenitor cells, endometrial cells, neutrophil pre-cursors and neutrophils. Further, in this method, the MUC1 receptor may be a cell surface attached cleavage product. The MUC1 cleavage product may be MGFR. Further, the MGFR may include PSMGFR. In this method, the MUC1 receptor may be activated by a multimerizing agent of the MUC1 receptor. Further, the multimerizing agent may be a bivalent agent. The bivalent agent may recognize a portion of the MGFR. Further, the bivalent agent may be a synthetic compound. The bivalent agent may be a dimeric ligand of MUC1. And still further, the bivalent agent may be an antibody. In the method above, the agent that increases the cleavage may be an enzyme. The enzyme may be TACE/ADAM17 or MMP14 also known as MT1-MMP.

In another aspect, the invention is directed to a method for treating a patient displaying symptoms of a low white blood count comprising administering to the patient an agent for activating MUC1 receptor in cells. The method may include administering to a subject who indicated need for such treatment, wherein activating is carried out by contacting the cells with (i) an agent that multimerizes the MGFR portion of MUC1; (ii) an agent that increases the cleavage of MUC1 to the growth factor receptor form; or (iii) a ligand that activates the MGFR portion of the MUC1 receptor.

In still another aspect, the invention is directed to a method for treating a patient, who displays symptoms indicating that a medicinal benefit would be achieved by causing immature cells to proliferate, with an agent that activates MUC1 receptor in cells. In this method, MUC1 may be activated by dimerizing the MGFR portion of the MUC1 receptor. MUC1 may also be activated by stimulating the cleavage of MUC1 such that the portion that remains attached to the cell surface consists essentially of the PSMGFR, preferably nat-PSMGFR. In this method also, MUC1 may be activated by stimulating the production of MUC1 or post-translationally modified MUC1. Further in this method, the MUC1 may be activated by stimulating the production of MUC1 or post-translationally modified MUC1 by adding Granulocyte-Colony Stimulating Factor (G-CSF).

In yet another aspect, the invention is directed to a method for treating a patient, who displays symptoms that could be relieved by causing immature cells to proliferate by administering a DNA encoding (i) MUC1, (ii) a fragment of MUC1 that is displayed on the cell surface, or (iii) the MGFR portion of MUC1, to the patient at the site for which the cells are desired be proliferated.

In another aspect, the invention is directed to a method for stimulating proliferation of immature cells in vitro by introducing DNA encoding MUC1, a fragment of MUC1 that is displayed on the cell surface, or the MGFR portion of MUC1. In this method, the patient may be in treatment with chemotherapy agents for the treatment of MUC1-negative cancers.

The invention is also directed to a composition comprising: (i) an agent that multimerizes the MGFR portion of MUC1; (ii) an agent that increases the cleavage of MUC1 to the growth factor receptor form; or (iii) a ligand that activates the MGFR portion of the MUC1 receptor; and a pharmaceutically-acceptable carrier.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given herein below, and the accompanying drawings which are given by way of illustration only, and thus are not limitative of the present invention, and wherein.

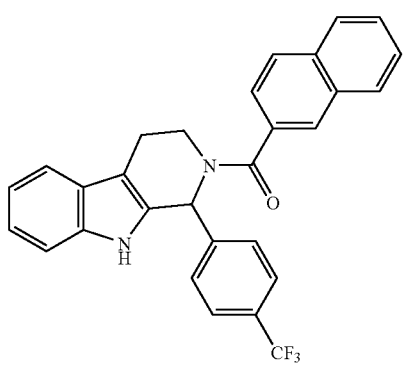 [SMILES: O=C(c1ccc2ccccc2c1)N1CCc2c([nH]c3ccccc23)C1c1ccc(C(F)(F)F)cc1]

Compound MN 21 is

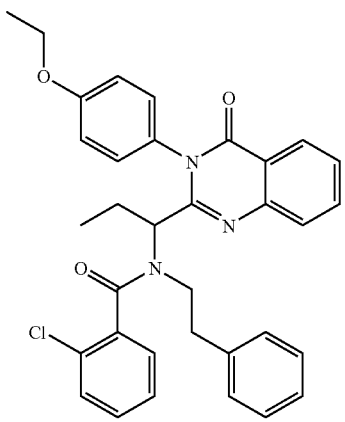 [SMILES: CCOc1ccc(-n2c(C(CC)N(CCc3ccccc3)C(=O)c3ccccc3Cl)nc3ccccc3c2=O)cc1]

and Compound MN 13 is

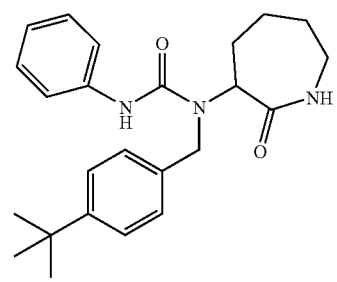 [SMILES: CC(C)(C)c1ccc(CN(C(=O)Nc2ccccc2)C2CCCCNC2=O)cc1]

Figure 1:
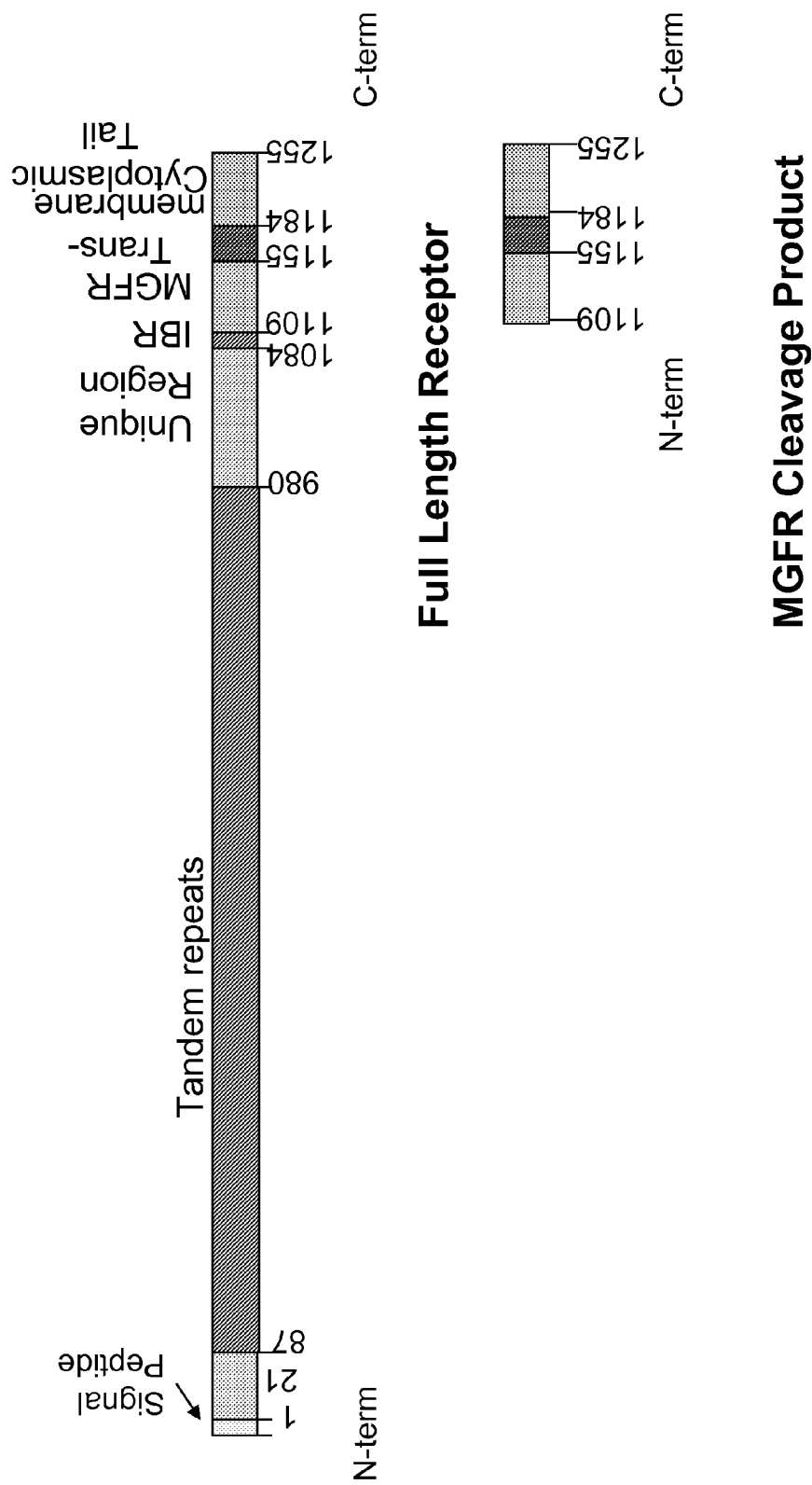
FIG. 1 is a schematic of the full length MUC1 receptor and the growth factor receptor cleavage product, MGFR.

FIGS. 7A-7B. Figures A and B show four (4) photographs of human breast cancer specimens under magnification. (A) and (C) are adjacent slices from the same section of a MUC1-positive cancer and (B) and (D) are adjacent slices from the same section of a MUC1-negative cancer. Sections (A) and (B) (top) have been treated with anti-PSMGFR that binds to the portion of the MUC1 receptor that remains attached to the cell surface after receptor cleavage. Sections (C) and (D) (bottom) have been treated with VU4H5 antibody that binds to the tandem repeat portion of the MUC1 receptor, which is frequently shed from the surface of cancer cells. Note the greater intensity of the anti-PSMGFR staining compared to VU4H5 staining. This result indicates that the predominant form of the MUC1 receptor on the surface of cancer cells is devoid of the tandem repeat portion and is comprised essentially of the PSMGFR sequence.

FIGS. 8A-8C. Figures A, B and C show three (3) photographs of adjacent slices of a breast cancer biopsy specimen stained with either A) H&E; B) anti-PSMGFR, or C) VU4H5. Comparison of B) and C) show that VU4H5 stains the cytoplasm diffusely while anti-PSMGFR clearly stains the cell surface membrane. This indicates that, on cancer cells, the MUC1 receptor has been cleaved to release the tandem repeat portion but leaves the portion containing the PSMGFR sequence attached to the cell surface.

FIGS. 9A-9D. Figures A, B, C and D show four (4) photographs of human lung cancer tissue specimens under magnification. (A) and (C) are adjacent slices from a first section of a MUC1-positive lung cancer and (B) and (D) are adjacent slices from a MUC1-negative cancer. Sections (A) and (B) (top) have been treated with anti-PSMGFR, which binds to the portion of the MUC1 receptor that remains attached to the cell surface after receptor cleavage. Sections (C) and (D) (bottom) have been treated with VU4H5 antibody that binds to the tandem repeat portion of the MUC1 receptor, which is frequently shed from the surface of cancer cells. Note the greater intensity of the anti-PSMGFR staining compared to VU4H5 staining and that anti-PSMGFR staining is restricted to the cell surface. These results again indicate that the predominant form of the MUC1 receptor on the surface of MUC1-positive lung cancer cells is mostly devoid of the tandem repeat portion and is comprised essentially of the PSMGFR sequence.

FIGS. 10A-10C. Figures A, B, and C show the same set of MUC1-positive lung cancer tissue specimens as in FIGS. 9A-9D at a greater magnification. At enhanced magnification, it is readily observed that the anti-PSMGFR staining is restricted to the cell surface whereas VU4H5 is diffuse and cytoplasmic, confirming that the MUC1 receptor on the surface of MUC1-positive lung cancer cells is cleaved to release the tandem repeat domain and leave the MGFR portion attached to the cell surface.

FIGS. 11A-11B. Figures A and B show two (2) photographs of colon cancer tissue specimens that have been stained with either (A) anti-PSMGFR or (B) VU4H5. The arrows point to portions of the section that are very cancerous as indicated by the fact that they have lost all cellular architecture. Section (A), shows dark regions of staining with anti-PSMGFR but the same region of the adjacent section (B), which has been stained with VU4H5, which recognizes the tandem repeat portion of the MUC1 receptor, shows no staining at all. These results indicate that, in MUC1-positive colon cancer, the MUC1 receptor has been cleaved to release the tandem repeat portion but leaves the portion of the receptor that contains the PSMGFR sequence intact and attached to the cell surface.

FIGS. 12A-12B. Figures A and B show two (2) photographs of MUC1-negative tissue specimens stained with either anti-PSMGFR (A) or VU4H5 (B). Note that in (A)

arrows point to several mast cells, the surface of which have been thoroughly stained with anti-PSMGFR but not with VU4H5. These results indicate that a cleaved form of the MUC1 receptor that contains the PSMGFR sequence, but not the tandem repeat domain, is present on the surface of mast cells.

Figure 12:
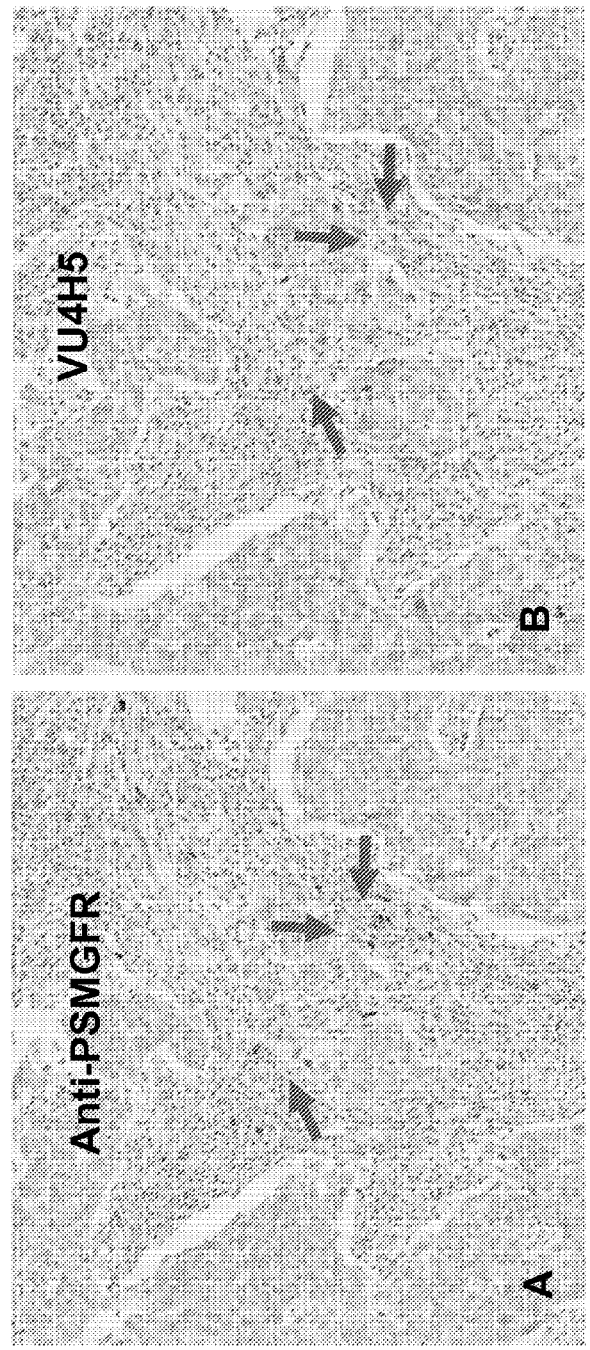
Figure 13:
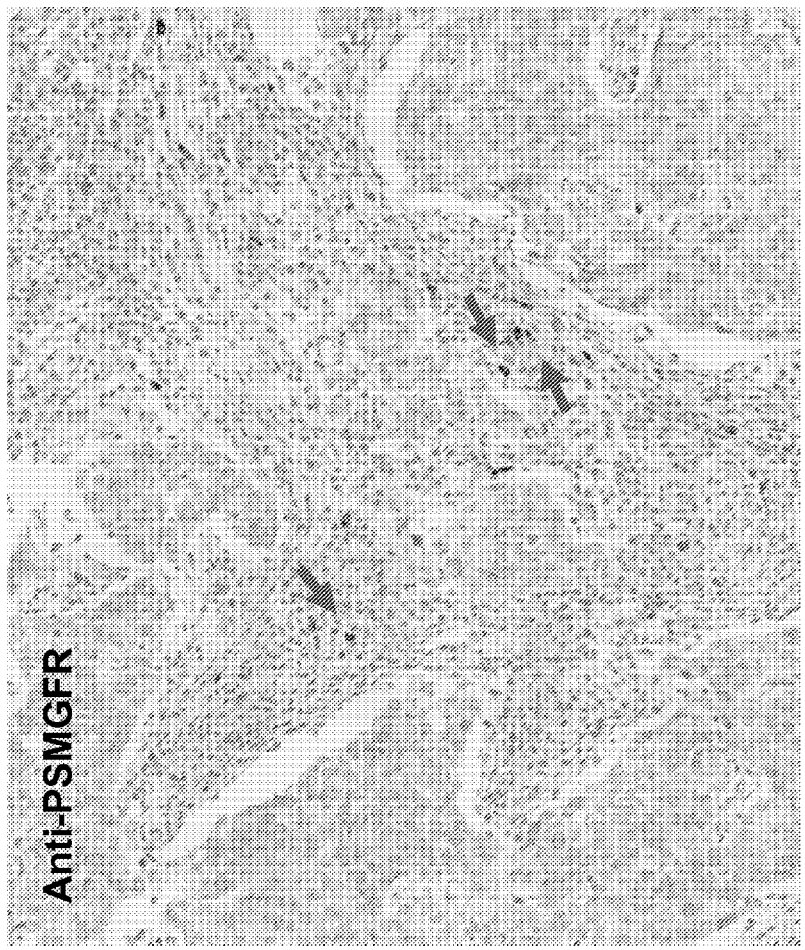

FIG. 13 is a greater magnification of FIG. 12 (A) and shows mast cells coated with anti-PSMGFR. Arrows point to mast cells coated with MUC1 cleavage product, PSMGFR.

FIGS. 14A-14B. Figures A and B show photographs of adjacent slices of healthy fallopian tube tissue specimens stained with either anti-PSMGFR (A) or VU4H5 (B) antibody.

DETAILED DESCRIPTION OF THE PREFERRED EMBODIMENTS

In the present application, "a" and "an" are used to refer to both single and a plurality of objects.

The term "MUC1 Growth Factor Receptor" (MGFR) is a functional definition meaning that portion of the MUC1 receptor that interacts with an activating ligand, such as a growth factor or a modifying enzyme such as a cleavage enzyme, to promote cell proliferation. The MGFR region of MUC1 is that extracellular portion that is closest to the cell surface and is defined by most or all of the PSMGFR, as defined below. The MGFR is inclusive of both unmodified peptides and peptides that have undergone enzyme modifications, such as, for example, phosphorylation, glycosylation, etc. Results of the invention are consistent with a mechanism in which this portion is made accessible to the ligand upon MUC1 cleavage at a site associated with tumorigenesis that causes release of the some or all of the IBR from the cell.

As used herein, "anti-PSMGFR" refers to any antibody that recognizes a region of the MGFR and optionally any portion of PSMGFR. Antibody to nat-PSMGFR is exemplified and preferred in the application, but is not meant to be limited to an antibody made against this specific sequence, as other fragments of MGFR and PSMGFR are also contemplated.

The term "Interchain Binding Region" (IBR) is a functional definition meaning that portion of the MUC1 receptor that binds strongly to identical regions of other MUC1 molecules giving MUC1 the ability to aggregate (i.e. self-aggregate) with other MUC1 receptors via the IBRs of the respective receptors. This self-aggregation may contribute to MUC1 receptor clustering, observed in healthy cells. In a preferred embodiment, the IBR may be approximately defined as a stretch of at least 12 to 18 amino acid sequence within the region of the full-length human MUC1 receptor defined as comprising amino acids 507 to 549 of the extracellular sequence of the MUC1 receptor (SEQ ID NO: 1), with amino acids 525 through 540 and 525 through 549 especially preferred (numbers refer to Andrew Spicer et al., J. Biol. Chem Vol 266 No. 23, 1991 pgs. 15099-15109; these amino acid numbers correspond to numbers 1067, 1109, 1085, 1100, 1085, 1109 of Genbank accession number P15941; PID G547937, SEQ ID NO: 1) or fragments, functional variants or conservative substitutions thereof, as defined in more detail below.

The term "cleaved IBR" means the IBR (or a portion thereof) that has been released from the receptor molecule segment which remains attached to the cell surface. The release may be due to enzymatic or other cleavage of the IBR. As used herein, when the IBR is "at the surface of a cell", it means the IBR is attached to the portion of the cell surface receptor that has not been shed, or cleaved. The cleaved IBR of interest is a "disease-associated cleavage", i.e. that type of cleavage that can result in cancer.

The term "Constant Region" (CR) is any non-repeating sequence of MUC1 that exists in a 1:1 ratio with the IBR and forms part of the portion of MUC1 that is shed upon cleavage in healthy and tumorigenesic cells.

The term "Repeats" is given its normal meaning in the art.

The term "Primary Sequence of the MUC1 Growth Factor Receptor" (PSMGFR) is a peptide sequence that defines most or all of the MGFR in some cases, and functional variants and fragments of the peptide sequence, as defined below. The PSMGFR is defined as SEQ ID NO: 10 listed below in Table 1, and all functional variants and fragments thereof having any integer value of amino acid substitutions up to 20 (i.e. 1, 2, 3, 4, 5, 6, 7, 8, 9, 10, 11, 12, 13, 14, 15, 16, 17, 18, 19, or 20) and/or any integer value of amino acid additions or deletions up to 20 at its N-terminus and/or C-terminus. A "functional variant or fragment" in the above context refers to such variant or fragment having the ability to specifically bind to, or otherwise specifically interact with, ligands that specifically bind to, or otherwise specifically interact with, the peptide of SEQ ID NO: 10. One example of a PSMGFR that is a functional variant of the PSMGFR peptide of SEQ ID NO: 10 (referred to as nat-PSMGFR—for "native") is SEQ NO: 12 (referred to as var-PSMGFR), which differs from nat-PSMGFR by including an -SPY- sequence instead of the native -SRY- (see bold text in sequence listings). Var-PSMGFR may have enhanced conformational stability, when compared to the native form, which may be important for certain applications such as for antibody production. The PSMGFR is inclusive of both unmodified peptides and peptides that have undergone enzyme modifications, such as, for example, phosphorylation, glycosylation, etc.

The term "Extended Sequence of the MUC1 Growth Factor Receptor" (ESMGFR) is a peptide sequence, defined below (See Table 1—SEQ ID NO: 15), that defines all of His-var-PSMGFR plus 9 amino acids of the proximal end of PSIBR.

The term "Tumor-Specific Extended Sequence of the MUC1 Growth Factor Receptor" (TSESMGFR) is a peptide sequence (See, as an example, Table 1—SEQ ID NO: 16) that defines a MUC1 cleavage product found in tumor cells that remains attached to the cell surface and is able to interact with activating ligands in a manner similar to the PSMGFR.

PSIBR is a peptide sequence, defined below (See Table 1—SEQ ID NO: 17), that defines most or all of the IBR.

"Truncated Interchain Binding Region" (TPSIBR) is a peptide sequence defined below (See Table 1—SEQ ID NO: 18), that defines a smaller portion of the IBR that is released from the cell surface after receptor cleavage in some tumor cells.

PSMGFRTC is a truncated MUC1 receptor isoform comprising PSMGFR and truncated at or within about up to 30 (i.e. within 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30) amino acids of its N-terminus and comprising the transmembrane and cytoplasmic sequences of full-length MUC1 receptor. As used herein, the phrase "at its N-terminus" referring to the location of a recited sequence within a larger molecule, such as a polypeptide or receptor, refers to such a sequence being no more than 30 amino acids from the N-terminal amino acid of the molecule. Optionally the PSMGFRTC, as well as the other truncated MUC1 receptor isoforms discussed below, can include a MUC1 N-terminal signaling sequence (Table 1—SEQ ID NOS: 2, 3, or 4), typically between 20 and 30 amino acids in length, or a functional fragment or variant thereof. Such a sequence is typically encoded by the nucleic acid constructs encoding the truncated MUC1 receptor isoform and is translated but is typically cleaved prior to or upon insertion of the receptor in the membrane of the cell. Such a PSMGFRTC, i.e. including the optional signal sequence, would still be a peptide or protein "having a PSMGFR" sequence "at its N-terminus" by the above definition. An example is nat-PSMGFRTC (SEQ ID NO: 5, with or without the signal peptide of SEQ ID NOS: 2, 3, or 4 at the extreme N-terminus) having nat-PSMGFR (SEQ NO: 10) at its N-terminus (i.e. at the extreme N-terminal end or within 30 amino acids thereof).

As used herein, "multimerization" of the receptors includes without limitation dimerization of the receptors. Further, multimerization includes binding of co-receptor or co-receptors with MUC1, or binding of multiple MUC1 receptors with each other, which may be gathered together by a ligand or ligands possessing multiple valences.

A "ligand" to a cell surface receptor, refers to any substance that can interact with the receptor to temporarily or permanently alter its structure and/or function. Examples include, but are not limited to binding partners of the receptor, (e.g. antibodies or antigen-binding fragments thereof), and agents able to alter the chemical structure of the receptor (e.g. modifying enzymes).

An "activating ligand" refers to a ligand able interact with a receptor to transduce a signal to the cell. Activating ligands can include, but are not limited to, species that effect inductive multimerization of cell surface receptors such as a single molecular species with greater than one active site able to bind to a receptor; a dimer, a tetramer, a higher multimer, a bivalent antibody or bivalent antigen-binding fragment thereof, or a complex comprising a plurality of molecular species. Activating ligands can also include species that modify the receptor such that the receptor then transmits a signal. Enzymes can also be activating ligands when they modify a receptor to make it a new recognition site for other activating ligands, e.g. glycosylases are activating ligands when the addition of carbohydrates enhances the affinity of a ligand for the receptor. Cleavage enzymes are activating ligands when the cleavage product is the more active form of the receptor, e.g. by making a recognition site for a ligand more accessible. In the context of MUC1 stem cells or progenitor cells, an activating ligand can be a species that cleaves MUC1, chemically modifies the receptor, or species that interact with the MGFRs on the surface of the MUC1 cells to transduce a signal to the cell that stimulates proliferation, e.g. a species that effects inductive multimerization.

A "growth factor" refers to a species that may or may not fall into a class of previously-identified growth factors, but which acts as a growth factor in that it acts as an activating ligand.

A "MUC1 presenting cell" refers to cells expressing MUC1 and/or MGFRs on the surface.

The term "immature cell" is used herein to refer to cells that are in various stages of differentiation from undifferentiated stem cells to progenitor cells and other cells such as various pre-cursor cells and neutrophils, which are partially differentiated, and excludes cells that are fully differentiated.

The term, "stem cell" refers to a cell with capability of multi-lineage differentiation and self-renewal, as well as the capability to regenerate tissue. Stem cells may originate from but not limited to umbilical cord blood, liver stem cells, pancreatic stem cells, neuronal stem cells, bone marrow stem cells, peripheral blood stem cells, or a mixture thereof. Further, the invention is not limited to transplantation of any particular stem cell obtained from any particular source, but may include stem cells from "multiple stem cell sources" in mixture with one another. Thus, expanded mesenchymal stromal cells may be used in cotransplantation of the stem cells obtained from single or multiple stem cell sources to increase the amount of engraftment.

The term "cancer", as used herein, may include but is not limited to: biliary tract cancer; bladder cancer; brain cancer including glioblastomas and medulloblastomas; breast cancer; cervical cancer; choriocarcinoma; colon cancer; endometrial cancer; esophageal cancer; gastric cancer; hematological neoplasms including acute lymphocytic and myelogenous leukemia; multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Kaposi's sarcoma, basocellular cancer, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma and Wilms tumor. Preferred cancers are; breast, prostate, lung, ovarian, colorectal, and brain cancer.

The term "cancer treatment" as described herein, may include but is not limited to: chemotherapy, radiotherapy, adjuvant therapy, or any combination of the aforementioned methods. Aspects of treatment that may vary include, but are not limited to: dosages, timing of administration, or duration or therapy; and may or may not be combined with other treatments, which may also vary in dosage, timing, or duration. Another treatment for cancer is surgery, which can be utilized either alone or in combination with any of the aforementioned treatment methods. One of ordinary skill in the medical arts may determine an appropriate treatment.

An "agent for prevention of cancer or tumorigenesis" means any agent that counteracts any process associated with cancer or tumorigenesis described herein.

An "agent that enhances cleavage of a cell surface receptor interchain binding region" as used herein is any composition that promotes cleavage at a particular location by modifying MUC1 with sugar groups or phosphates that create a recognition motif for cleavage at that location. Other enzymes can promote cleavage of receptors by activating other cleavage enzymes. One way to select agents that enhance cleavage of a cell surface receptor IBR is to first identify enzymes that affect cleavage as described above, and screen agents, and their analogs, for their ability to alter the activity of those enzymes. Another way is to test agents that are known to affect the activity of similar enzymes (e.g. from the same family) for their ability to alter the site of cleavage of MUC1, and to similarly test analogs of these agents. Alternatively, agents are screened in a cell-free assay containing the enzyme and MUC1 receptors, and the rate or position of cleavage measured by antibody probing, Polymerase Chain Reaction (PCR), or the like. Alternatively, without first identifying enzymes that affect MUC1, agents are screened against cells that present MUC1 for the agents' ability to alter cleavage site or the rate of cleavage of MUC1. For example, agents can be screened in an assay containing whole cells that present MUC1 and aggregation potential of the cell supernatant can be measured, an indication of the amount of IBR that remains attached to the cleaved portion of MUC1, i.e. the degree of cleavage between MGFR and IBR. In another technique, agents can be screened in an assay containing whole cells that present MUC1, the supernatant removed, and the cell remain tested for accessibility of the MGFR portion, e.g. using a labeled antibody to the MGFR. Agents can be identified from commercially available sources such as molecular libraries, or rationally designed based on known agents having the same functional capacity and tested for activity using the screening assays.

An "agent that enhances cleavage of the MUC1 receptor" is any composition that promotes or enhances cleavage of the MUC1 receptor at any location. Such an agent can be used to increase the population of stem cell or progenitor cells, which if cleavage is effected, then the accessibility of the MGFR, a functional receptor associated with cell proliferation, is enhanced or promoted. Such agents can be selected by exposing cells to a candidate agent and determine, in the supernatant, the amount of cleaved MUC1 receptor, relative to a control.

A subject, as used herein, refers to any mammal (preferably, a human), and preferably a mammal that has a disease that may be treated by administering stem cells or progenitor cells to a site within the subject. Examples include a human, non-human primate, cow, horse, pig, sheep, goat, dog, or cat. Generally, the invention is directed toward use with humans.

The samples used herein are any body tissue or body fluid sample obtained from a subject. Preferred are body fluids, for example lymph, saliva, blood, urine, milk and breast secretions, and the like. Blood is most preferred. Samples of tissue and/or cells for use in the various methods described herein can be obtained through standard methods including, but not limited to: tissue biopsy, including punch biopsy and cell scraping, needle biopsy, and collection of blood or other bodily fluids by aspiration or other methods.

Cell Expansion Through MUC1 Receptor Manipulation

The present application discloses that the portion of the MUC1 receptor that remains attached to the cell surface following receptor cleavage, MGFR, consisting primarily of Nat-PSMGFR (Table 1: SEQ ID NO: 10) (FIG. 1), is a primal growth factor receptor that drives the growth of stem cells and or progenitor cells or more broadly cells that may yet undergo another step of differentiation. The receptor may be purposely activated to promote the growth of these stem cells or pre-cursor cells in vitro, ex vivo, and/or in vivo for therapeutic, research and other purposes.

The MUC1 receptor may be purposely activated by: 1) inducing receptor cleavage; 2) treating cells bearing the receptor with an activating ligand which may be an agent that dimerizes the receptor, including an antibody that binds to a portion of the receptor that is accessible; 3) transfecting cells with the MUC1 receptor or the MGFR portion thereof, and/or delivering a gene or other mechanism that allows a cell to express the MUC1 receptor and/or its activating ligands.

Figure 8:
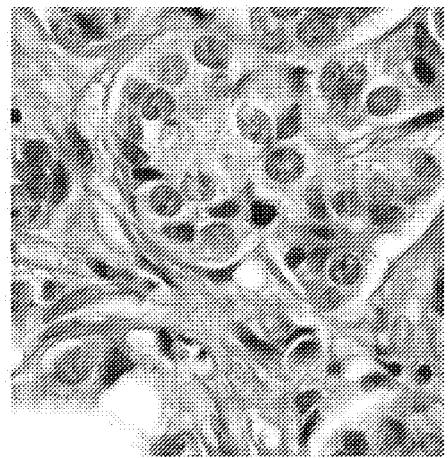
Figure 8:
Figure 8:
Figure 10:
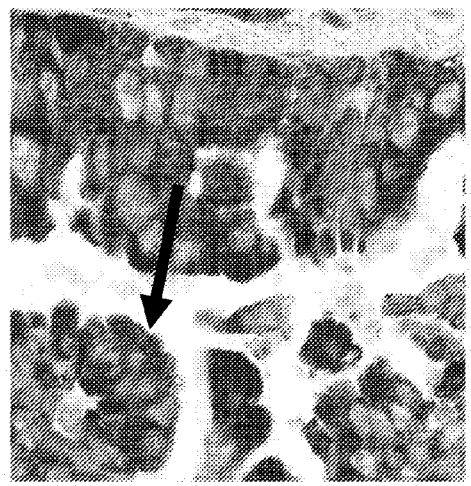
Figure 10:
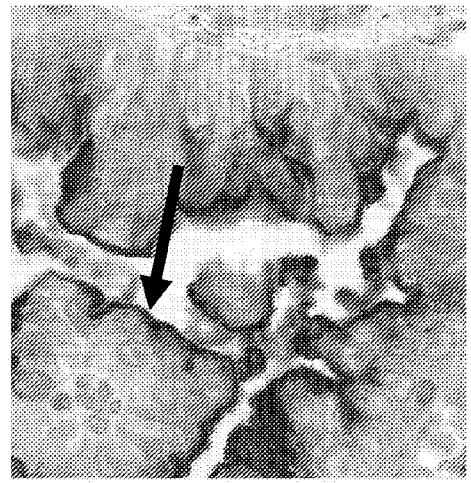
Figure 10:
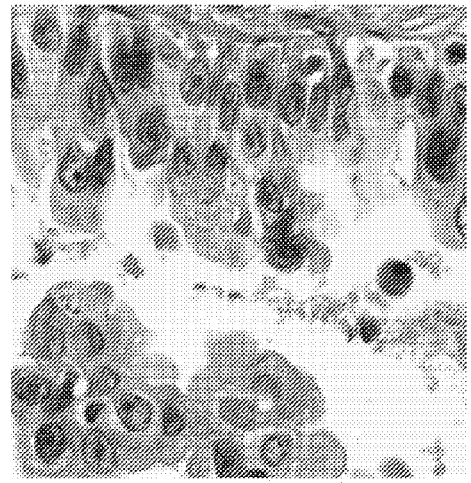
Figure 14:
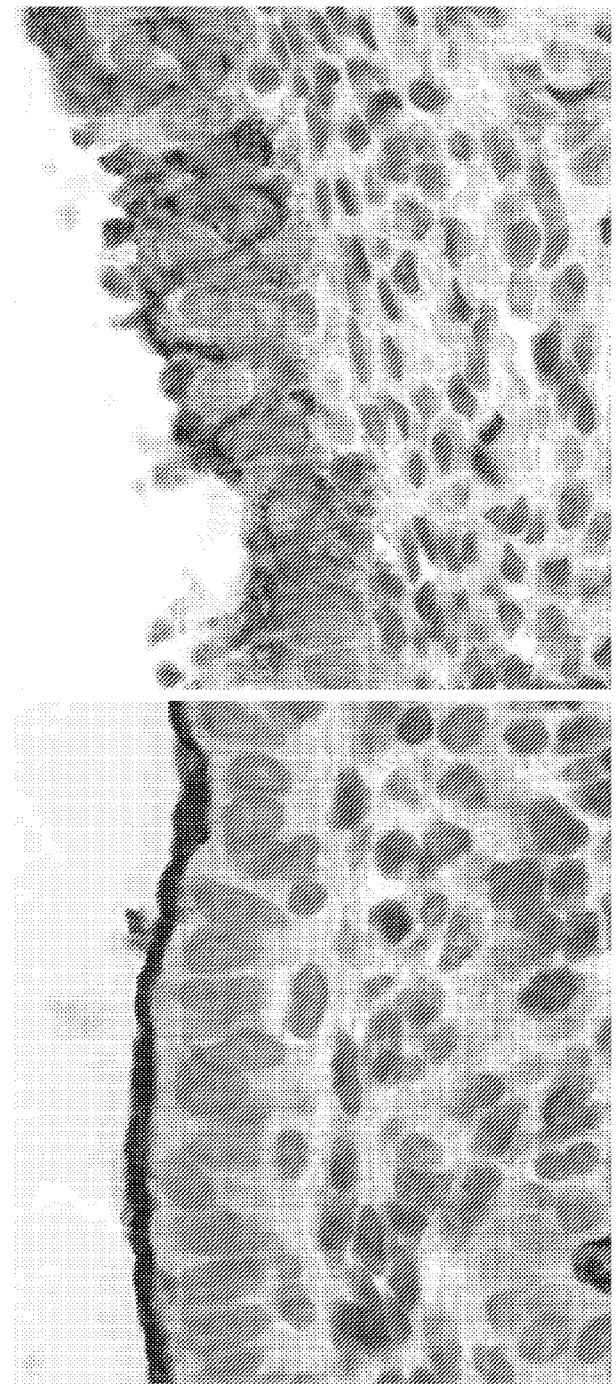

The MUC1 receptor is expressed on normal epithelium, wherein the receptor is typically clustered at the apical border of adult luminal cells. MUC1 is also expressed on intestinal mucosa, pluri-potent bone marrow stem cells, neutrophil precursors and neutrophils. Applicant has observed that mast cells are coated with a truncated MUC1 receptor that consists essentially of the PSMGFR sequence (FIGS. 12 and 13). A recent publication showed that when breast cancer patients were treated with G-CSF (granulocyte colony stimulating factor) their serum levels of shed MUC1 greatly increased (G-CSF induces elevation of circulating CA 15-3 in breast carcinoma patients treated in an adjuvant setting. Briasoulis E, Andreopolou E, Tolis C F, Bairaktari E, Katsaraki A, Dimopoulos M A, Fountzilas G, Seferiadis C ans Pavlidis N. (2001) Cancer, 91, 909-917). Their investigation showed that the increase in levels of shed MUC1 correlated with an increase in the number of neutrophils. These researchers reported that these neutrophils bear an increased number of MUC1 receptors in the cytoplasm, but not on the surface of the neutrophil. Applicant showed that the conclusions reached in this publication, i.e. that the neutrophils did not express MUC1 on their surface, is an erroneous conclusion because the studies cited used an antibody (CA 15.3) that recognizes the tandem repeat portion of the MUC1 receptor, (see FIGS. 8, 10 and 14). FIGS. 8 and 10 show that both breast and lung cancer cells stain positive for the MUC1 receptor in the cytoplasm, but not on the cell surface when probed with VU4H5, which is an antibody that binds to the tandem repeat portion of the receptor. However, when the adjacent section is probed with anti-PSMGFR, which binds to the PSMGFR portion of the receptor, it can be seen that a cleavage product of the receptor completely coats the cell surface. The applicants previously showed that a cleavage product of the MUC1 receptor that is essentially comprised of the PSMGFR sequence, functions as a growth factor receptor. FIG. 14 shows a tissue specimen of a healthy fallopian tube that shows that the luminal cells that line the tube stain positive on the cell surface when probed with anti-PSMGFR (A), but only stain positive in the cytoplasm when probed with VU4H5 (B). The cells that line the fallopian tubes and other ducts display a MUC1 cleavage product that contains the PSMGFR region but not the tandem repeats. These luminal cells are not cancerous but must be frequently replenished. These tissues contain stem cells and progenitor cells to make this rapid turnover of cells possible.

These data are consistent with the idea that G-CSF stimulated the proliferation of neutrophils and that the enhanced proliferation is due to an increased number of MUC1 receptors that are present on the surface of neutrophils in the cleaved form, which has been stripped of the tandem repeat section, and that this proteolyzed form of MUC1 is the growth factor receptor that is driving proliferation. Cells in human cancerous tissue specimens also show heavy cytoplasmic staining for MUC1 and no surface staining, when using antibodies that bind to the tandem repeat portion of the receptor (FIGS. 7C, 8C, and 10C). However, probing of the adjacent tissue slice with an antibody against the PSMGFR region of MUC1 showed that the entire cell surface was uniformly coated with a cleaved MUC1 that did not contain the tandem repeat section but did contain the PSMGFR sequence (FIGS. 7A, 8B, and 10B). In light of these findings, the predominant form of the MUC1 receptor on neutrophils, their pre-cursors and on stem cells, including pluri-potent stem cells, is the cleaved form, comprising or consisting essentially of PSMGFR. This cleaved MUC1 mediates proliferation and expansion of some if not all stem cells, progenitor cells, neutrophils and pre-cursors. Further, dimerization of the MGFR portion of MUC1 triggers this cell proliferation, optionally with an agent for doing so. Therefore, agents that dimerize MUC1 can be used to stimulate the growth of certain cell types, such as in vitro, ex vivo, in vivo, or in situ. Specifically, stem cells, progenitor, precursor cells, neutrophils and the like, can be stimulated to proliferate by adding agents that dimerize or multimerize the MGFR portion of MUC1.

Bivalent antibodies directed against the PSMGFR or nat-PSMGFR sequence of the MUC1 receptor have been shown to stimulate the growth of MUC1 presenting tumor cells (FIGS. 2-6). Similar antibodies can be used to activate the MUC1 receptor and promote the proliferation of a variety of non-cancerous cells including immature cells or stem cells.

Anti-PSMGFR or anti-nat-PSMGFR are examples of such antibodies. However any antibody directed against any region of the MGFR may be used to stimulate the growth of MUC1-positive cells wherein the nat-PSMGFR portion of the receptor is accessible. Natural ligands of the MUC1 receptor or functional mimics thereof may also be used to promote MUC1-mediated cell growth. Ligands of the MUC1 receptor may include but are not limited to NM23, 14-3-3, and/or cathepsin D.

Alternatively, enzymes such as TACE/ADAM17 or MT1-MMP/MMP14 can be administered to cells presenting the full length receptor to enhance cleavage to the growth factor receptor form and thus promote cell growth. Any enzyme that is able to cleave the MUC1 receptor such that the PSMGFR portion of the receptor becomes exposed would constitute an acceptable method for promoting the proliferation of MUC1-presenting cells.

As reported in the literature, G-CSF enhances the production of MUC1 and specifically of the cleaved form of MUC1 that acts as a growth factor receptor. Therefore, strategies to stimulate the growth of stem cells, neutrophils and other cell types that present both the MUC1 receptor and/or the G-CSF receptor may include agents that act on both the G-CSF receptor and the MUC1 receptor, specifically the portion that remains attached to the cell surface after receptor cleavage. That is to say that stem cell proliferation as well as increased neutrophil populations may be achieved by co-stimulation of both receptors, either simultaneously or in staggered treatment protocols.

There are many uses for techniques to stimulate the growth of stem cells, progenitor cells, neutrophils, mast cells and their precursors. A single stem cell can proliferate and differentiate to become an entire organ. Methods to manipulate the growth and/or differentiation of stem cells and progenitors would find uses in tissue regeneration, organ generation, expansion of depleted cell populations to treat conditions such as spinal column injury and Alzheimer's disease. Growth of these cells may be carried out in vitro or ex vivo. For example, a patient's own cells could be expanded then re-introduced to the patient. Alternatively, stimulating agents may be introduced in vivo, either alone or in combination with stem cells or stem cell-like cells, e.g. at a site of tissue or nerve injury. In other embodiments, allogeneic cells may be used in the case of stem cells.

In a preferred embodiment, agents that are directed to the MGFR portion of the MUC1 receptor, such as a dimerizing antibody, can be used to enhance white blood cell count in patients receiving therapies that induce neutropenia. These agents may be directly administered to patients being treated for non-cancerous conditions or MUC1-negative cancers, as well as other immuno-compromised patients. Alternatively, a patient's own neutrophils or precursors thereof may be removed from the patient and expanded, using methods of the invention, then re-introduced into the patient. For example, this would eliminate the need for bone marrow transplants for patients who have undergone extensive radiation or other methods that destroy the bone marrow. Conditions such as leukemias may also be treated with this method to restore the patient's immune system and blood profile. Methods of the invention including antibodies that dimerize the MGFR portion of the MUC1 receptor may be administered to neutrophils or their precursors in vitro or ex vivo, then depleted of the antibody and re-introduced to the patient. Similarly, agents that increase the cleavage of MUC1 to the growth factor receptor form can be used to stimulate the growth of immature cells, such as but not limited to stem cells, progenitor, precursor cells, neutrophils, and neutrophil pre-cursors.

Ligands, such as growth factors, that activate the MGFR portion of the MUC1 receptor may also be used to stimulate the growth of these cell types. These methods may be used to stimulate the proliferation of stem cells, neutrophils, or any other cell that presents the cell surface receptor MUC1, where cell proliferation would be desired.

A form of gene therapy designed to stimulate the growth of immature cells such as stem cells, progenitor cells, neutrophils, or neutrophil pre-cursors, comprises introducing DNA that codes for MUC1 or preferably the truncated MUC1, consisting essentially of the PSMGFR, into immature cells such as stem cells, progenitor cells, neutrophils or like cells wherein proliferation is desirable. DNA that encodes the MUC1 ligand or antibodies that bind to the portion of the receptor that remains attached to the cell surface after cleavage may be introduced to stimulate the growth of the new cells. DNA encoding the G-CSF receptor may be introduced in parallel since G-CSF stimulates the expression or cleavage of the MUC1 receptor.

In another embodiment, the invention involves administering or adding G-CSF in combination with an agent that activates MUC1 and/or an agent that dimerizes the MUC1 receptor and/or assists in cleaving MUC1 to cause the proliferation of stem cells, neutrophils, and other cell types that present both the MUC1 receptor and/or the G-CSF receptor Agents that perform the functions described above can be identified, synthesized, and/or selected by those of ordinary skill in the art based upon the disclosure herein without undue experimentation.

MUC1 Expression in Tumor Cells

Figure 7:
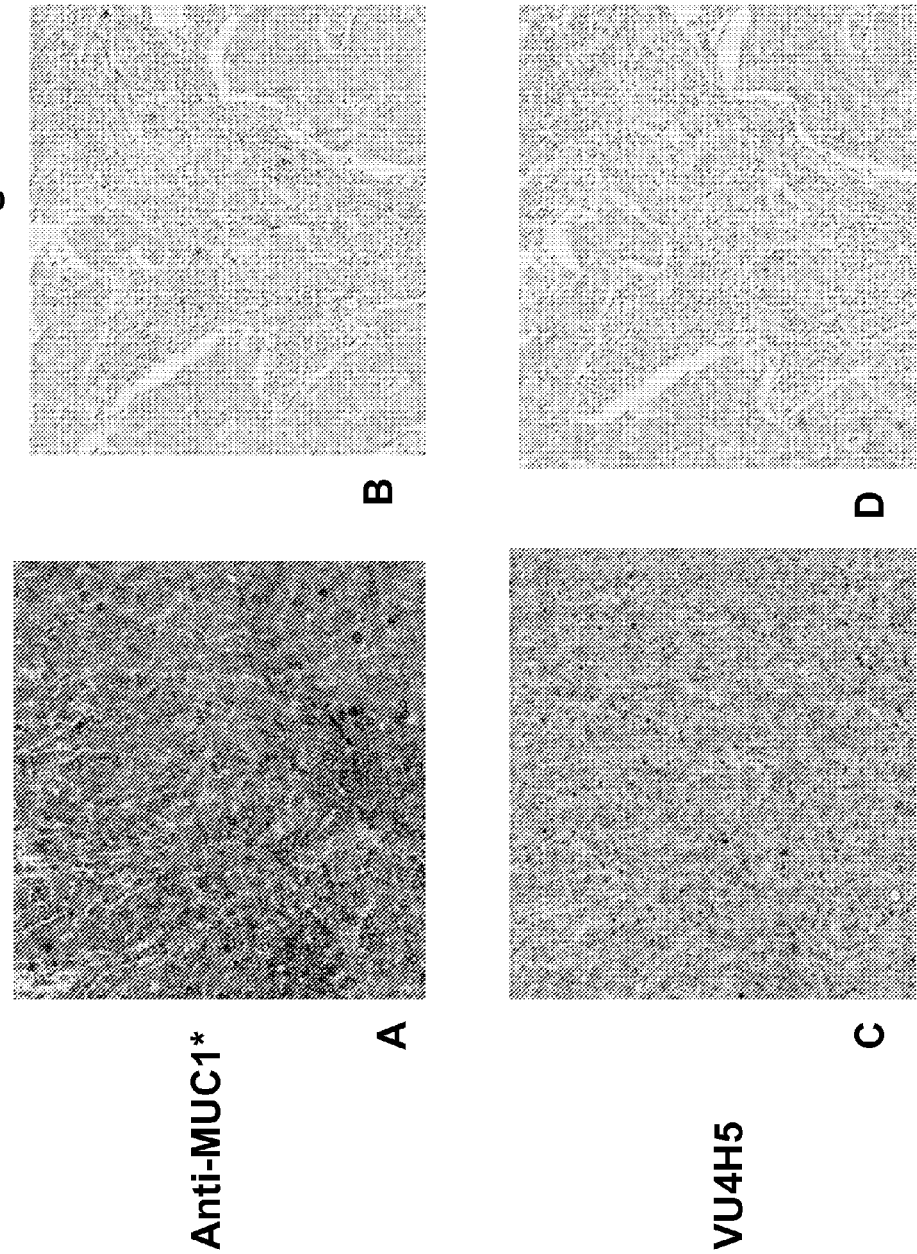
Figure 9:
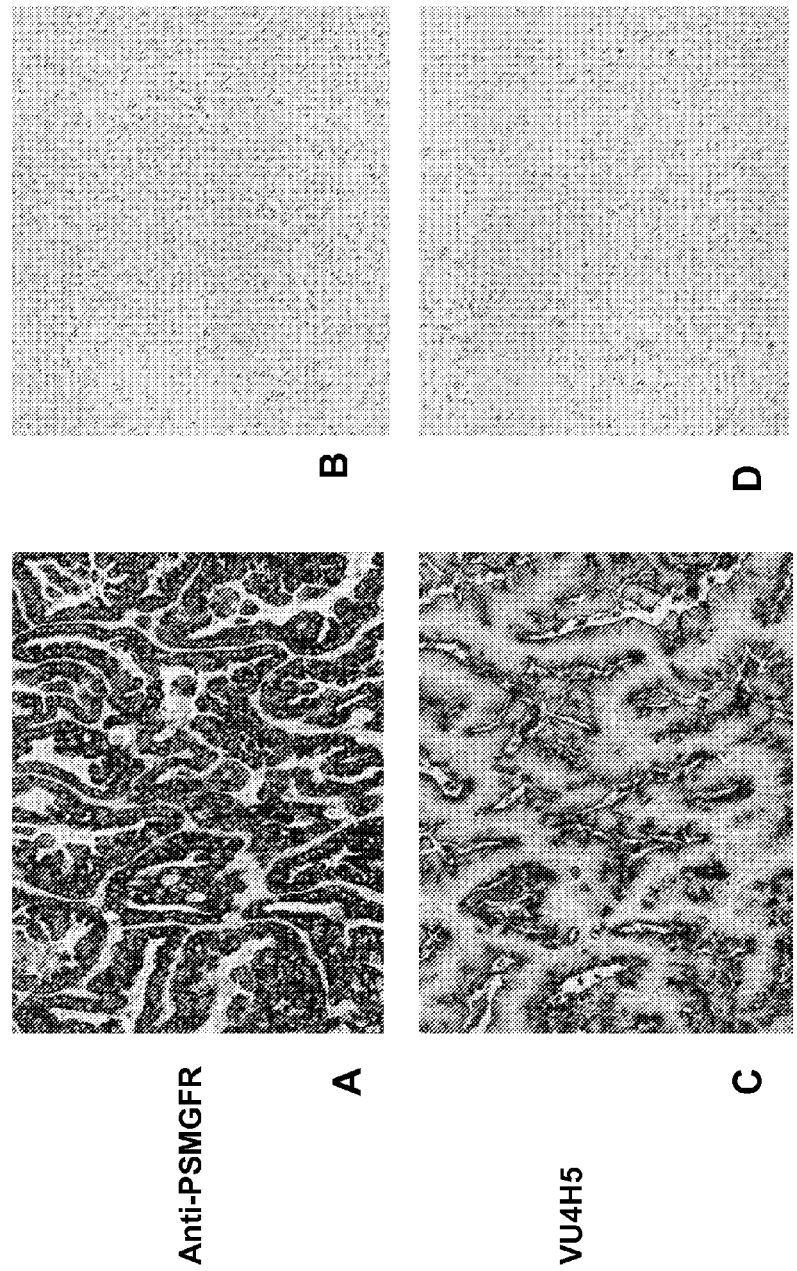
Figure 11:
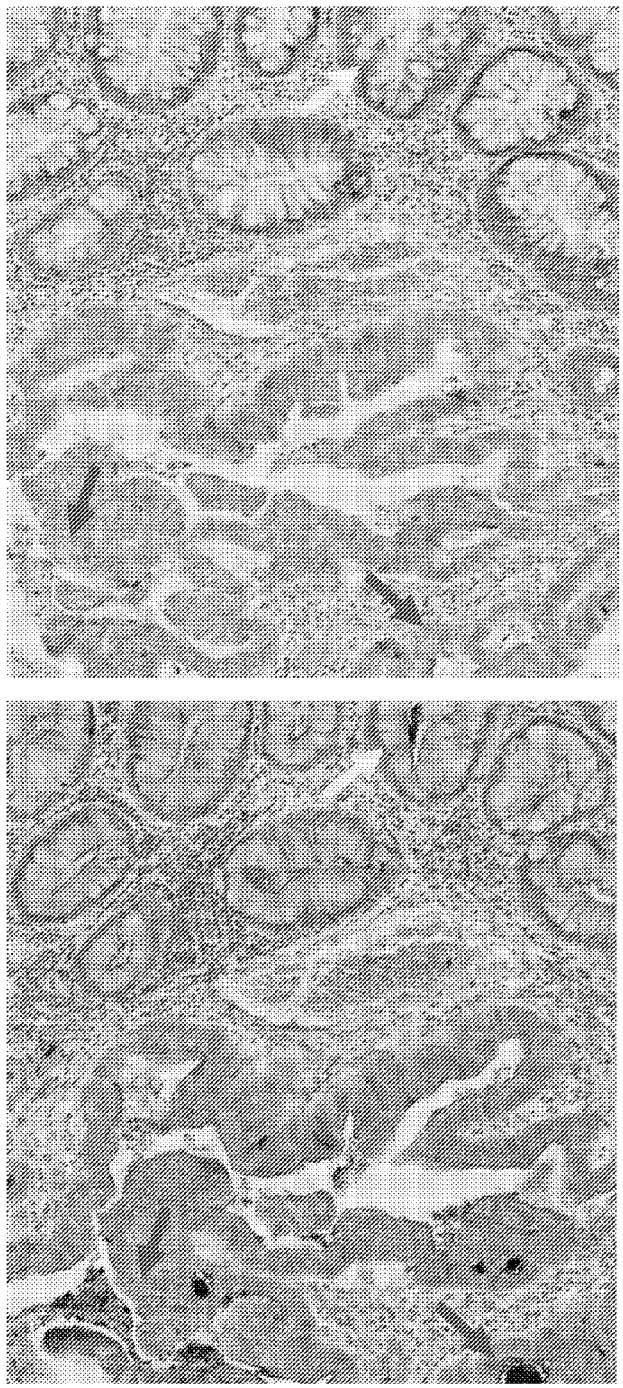

A key mechanism of cell growth in MUC1 positive cancers may depend more on the amount of MUC1 cleavage that occurs rather than the overall amount of MUC1 receptor that is expressed. Low molecular weight species that migrate on an acrylamide gel with an apparent molecular weight of around 20-30 kD (some glycosylated) exist in MUC1-positive tumor cells but do not exist in sufficient numbers to be detectable in non-tumor MUC1 cells. Two cleavage sites of the MUC1 receptor in tumor cells were previously identified. The first cleavage site occurs in the middle of the IBR and the second cleavage site, which our evidence indicates is the more tumorigenic form, occurs at the C-terminal end of the IBR: the first cleavage site being located at the N-terminus of TPSIBR (SEQ ID NO: 17) and the second cleavage site being located at the N-terminus of the nat-PSMGFR having SEQ ID NO: 13. When cleavage occurs at the first site, the portion of the receptor that remains attached to the cell surface is similar to TSESMGFR (See Table 1, SEQ ID NO: 16, but with the native SRY sequence). When cleaved at the second site, the remaining portion is a PSMGFR as shown in Table 1, SEQ ID NO: 11. This low molecular weight species that is tumor specific consists essentially of the native PSMGFR sequence and in some cases the TSESMGFR sequence and is available to cognate ligands, i.e. not self-aggregated, than on the overall amount of MUC1 receptor expressed by the cell. Supporting this conclusion, susceptibility of tumor cells to proliferate was found, within the context of the present invention, to be a function of the amount of the shorter form of the MUC1 receptor. FIG. 7 shows four (4) photographs of human breast cancer specimens under magnification. (A) and (C) are adjacent slices from the same section of a MUC1-positive cancer and (B) and (D) are adjacent slices from the same section of a MUC1-negative cancer. Sections (A) and (B) (top) have been treated with anti-PSMGFR that binds to the portion of the MUC1 receptor that remains attached to the cell surface after receptor cleavage. Sections (C) and (D) (bottom) have been treated with VU4H5 antibody that binds to the tandem repeat portion of the MUC1 receptor, which is frequently shed from the surface of cancer cells. Note the greater intensity of the anti-PSMGFR staining compared to VU4H5 staining. This result indicates that the predominant form of the MUC1 receptor on the surface of cancer cells is devoid of the tandem repeat portion and is comprised essentially of the PSMGFR sequence. FIG. 9 shows four (4) photographs of human lung cancer tissue specimens under magnification. (A) and (C) are adjacent slices from a first section of a MUC1-positive lung cancer and (B) and (D) are adjacent slices from a MUC1-negative cancer. Sections (A) and (B) (top) have been treated with anti-PSMGFR, which binds to the portion of the MUC1 receptor that remains attached to the cell surface after receptor cleavage. Sections (C) and (D) (bottom) have been treated with VU4H5 antibody that binds to the tandem repeat portion of the MUC1 receptor, which is frequently shed from the surface of cancer cells. Note the greater intensity of the anti-PSMGFR staining compared to VU4H5 staining and that anti-PSMGFR staining is restricted to the cell surface. These results again indicate that the predominant form of the MUC1 receptor on the surface of MUC1-positive lung cancer cells is mostly devoid of the tandem repeat portion and is comprised essentially of the PSMGFR sequence. FIG. 11 shows two (2) photographs of colon cancer tissue specimens that have been stained with either (A) anti-PSMGFR or (B) VU4H5. The arrows point to portions of the section that are very cancerous as indicated by the fact that they have lost all cellular architecture. Section (A), shows dark regions of staining with anti-PSMGFR but the same region of the adjacent section (B), which has been stained with VU4H5, which recognizes the tandem repeat portion of the MUC1 receptor, shows no staining at all. These results indicate that, the fastest growing portions of the tumor present a form of MUC1 that is devoid of the tandem repeat portion but leaves the portion of the receptor that contains the nat-PSMGFR sequence intact and attached to the cell surface.

Figure 2:
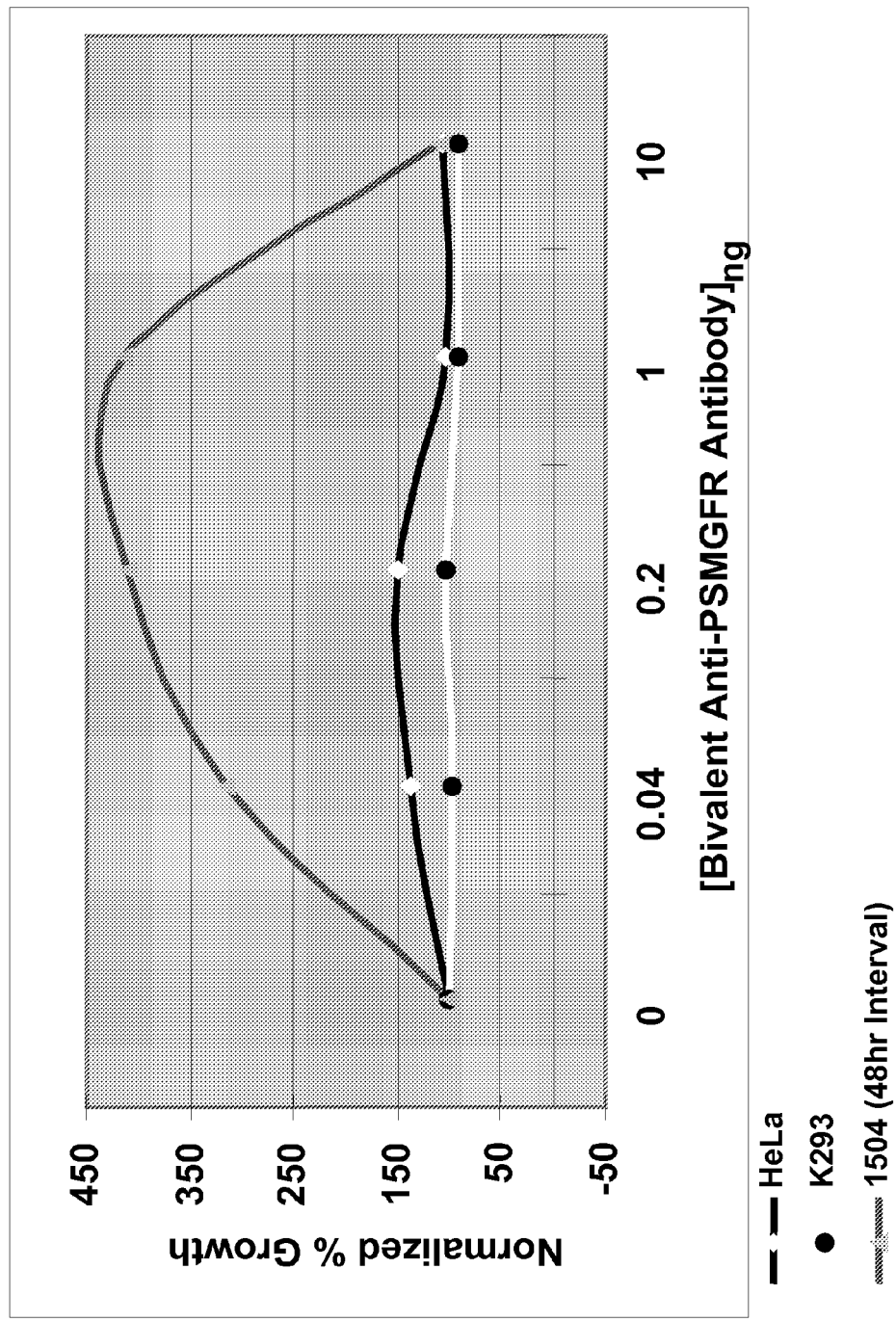
FIG. 2 is a graph of a cell proliferation assay in which three (3) different cells lines (A) breast cancer cell line 1504, (B) HeLa cells which are very slightly MUC1-positive and show a slight response in growth to MUC1 dimerization, and (C) HEK 293 cells which are MUC1-negative, were treated with anti-PSMGFR. Normalized cell growth is plotted as a function of antibody concentration. The growth curve of the MUC1-positive breast cancer cell line 1504 shows the typical biphasic response that is characteristic of a Class I growth factor receptor; cell growth is enhanced as antibody concentration is increased as each antibody dimerizes every two receptors. Cell growth begins to decline as antibody concentration becomes too high and each single antibody binds to a single receptor rather than dimerizing two receptors. Absent dimerization, the growth signal is lost. HEK 293 cells show no response to MUC1 stimulation by anti-PSMGFR since they are devoid of MUC1 receptors. These results indicate that the portion of the MUC1 receptor that contains the PSMGFR sequence functions as a growth factor receptor and stimulates the cell to divide when dimerized. Anti-Muc1* refers to anti-PSMGFR antibody.

In further support of the conclusion that cleavage products of the MUC1 receptor function as growth factor receptors in tumor cells, HEK cells were transfected with MUC1 variants that were either terminated after the PSMGFR (see Table 1, SEQ ID NO: 5) or after the entire interchain binding region (PSIBR) (SEQ ID NO: 6). Cells transfected with the receptor that included the PSIBR grew at a rate 4-6 times slower than cells transfected with the MUC1 variants that were terminated after the PSMGFR (e.g. SEQ ID NO: 5). Applicant has previously shown that a proteolyzed form of MUC1 is a growth factor receptor that drives the proliferation of a wide range of cancer cells. FIG. 2 is a graph of a cell proliferation assay in which three (3) different cells lines (A) breast cancer cell line 1504, (B) HeLa cells which are very slightly MUC1-positive and show a slight response in growth to MUC1 dimerization, and (C) HEK 293 cells which are MUC1-negative, were treated with anti-PSMGFR. Normalized cell growth is plotted as a function of antibody concentration. The growth curve of the MUC1-positive breast cancer cell line 1504 shows the typical biphasic response that is characteristic of a Class I growth factor receptor; cell growth is enhanced as antibody concentration is increased as each antibody dimerizes every two receptors.

Figure 3:
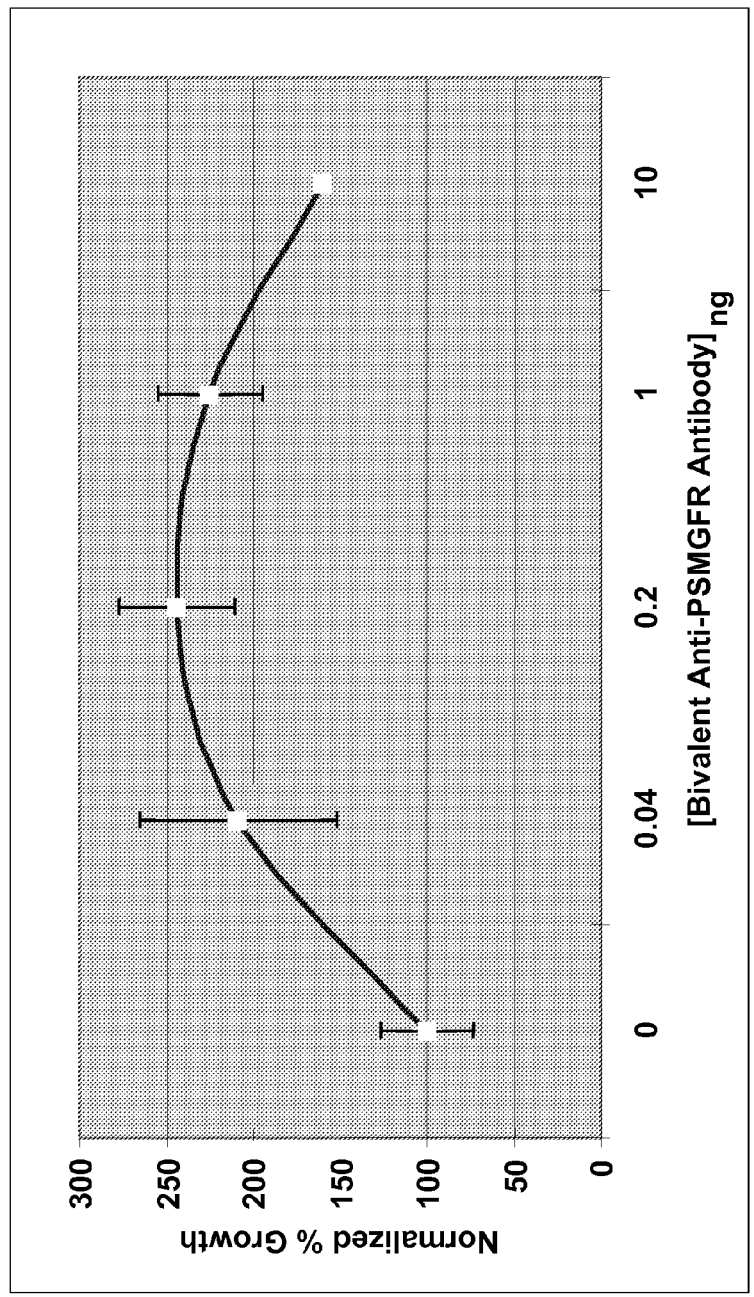
FIG. 3 is a graph of a cell proliferation assay in which human embryonic kidney (HEK) 293 cells (MUC1-negative) that had been stably transfected with a MUC1 receptor that had a truncated ectodomain, terminated at the end of the PSMGFR sequence, were treated with anti-PSMGFR. Normalized cell growth is plotted as a function of antibody concentration and shows that the PSMGFR portion of the MUC1 receptor mediates cell growth via dimerization of this portion of the receptor.
Figure 4:
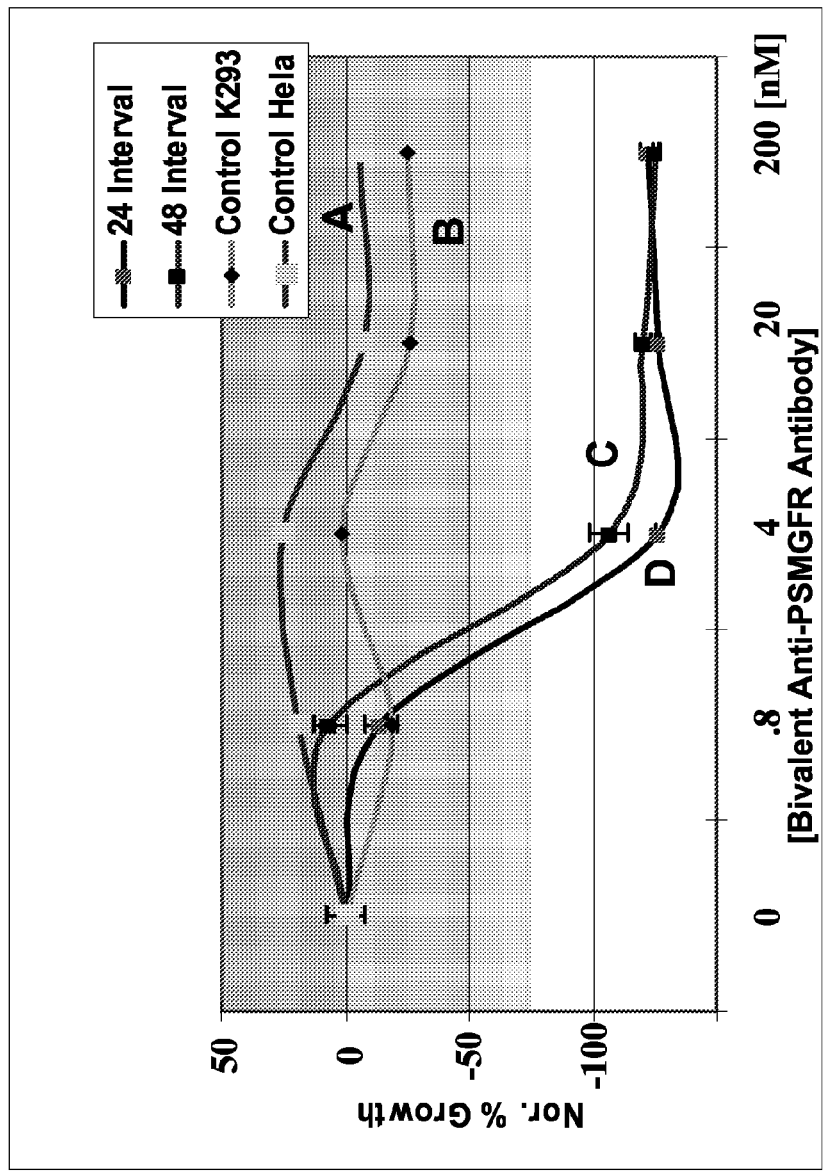
FIG. 4 is a graph of a cell proliferation assay in which three (3) cell lines were treated with the monovalent-anti-PSMGFR which is incapable of dimerizing the receptor. The graph shows that the control cell lines (A) HeLa and (B) HEK 293s are unaffected by the addition of the antibody but in MUC1-positive cell line breast cancer cell line 1504 (C) and (D), cell growth is inhibited.
Figure 5:
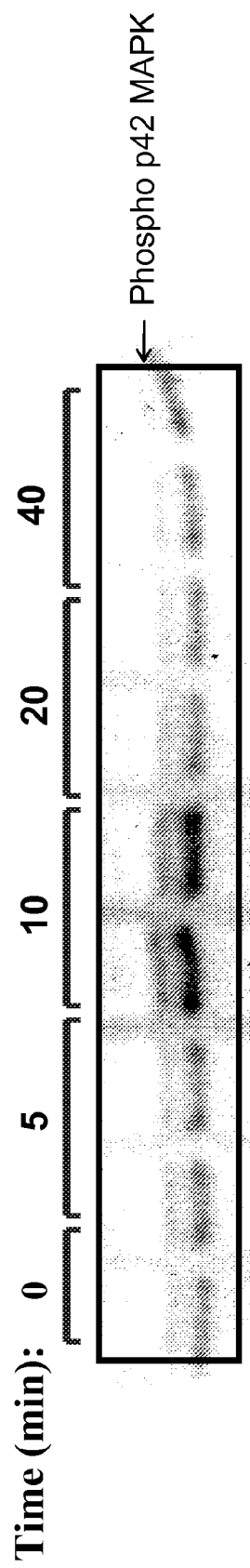
FIG. 5 is a western blot that shows that the ERK2 branch of the MAP kinase proliferation pathway is activated (ERK2 is phosphorylated) upon dimerization of the PSMGFR region of the MUC1 receptor.
Figure 6:
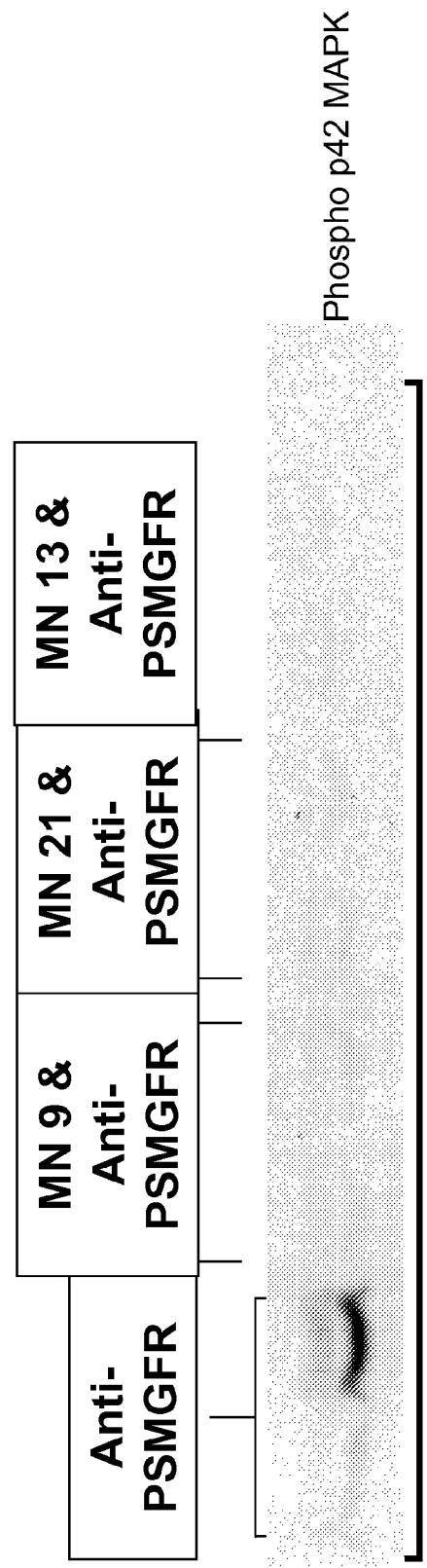
FIG. 6 is a western blot of a competition experiment in which small molecules that bind to the PSMGFR region of MUC1 compete with anti-PSMGFR for binding to the site. In the presence of the competitor small molecule, the antibody does not bind and ERK2 phosphorylation is inhibited. These results indicate that the PSMGFR portion of the MUC1 receptor mediates cell growth and dimerization of the receptor can trigger this growth signal. The chemical formula for the competitor compound MN 9 referred to in this figure is

Cell growth begins to decline as antibody concentration becomes too high and each single antibody binds to a single receptor rather than dimerizing two receptors. Absent dimerization, the growth signal is lost. HEK 293 cells show no response to MUC1 stimulation by anti-PSMGFR since they are devoid of MUC1 receptors. These results indicate that the portion of the MUC1 receptor that contains the PSMGFR sequence functions as a growth factor receptor and stimulates the cell to divide when dimerized. FIG. 3 is a graph of a cell proliferation assay in which human embryonic kidney (HEK) 293 cells (MUC1-negative) that had been stably transfected with a MUC1 receptor that had a truncated ectodomain, terminated at the end of the PSMGFR sequence, were treated with anti-PSMGFR antibody. Normalized cell growth is plotted as a function of antibody concentration and shows that the PSMGFR portion of the MUC1 receptor mediates cell growth via dimerization of this portion of the receptor. FIG. 4 is a graph of a cell proliferation assay in which three (3) cell lines were treated with the monovalent-anti-PSMGFR which is incapable of dimerizing the receptor. The graph shows that the control cell lines (A) HeLa and (B) HEK 293s are unaffected by the addition of the antibody but in MUC1-positive breast cancer cell line 1504 (C) and (D), cell growth is inhibited. FIG. 5 is a western blot that shows that the ERK2 branch of the MAP kinase proliferation pathway is activated (ERK2 is phosphorylated) upon dimerization of the PSMGFR region of the MUC1 receptor. FIG. 6 is a western blot of a competition experiment in which small molecules that bind to the PSMGFR region of MUC1 compete with anti-PSMGFR for binding to the site. In the presence of the competitor small molecule, the antibody does not bind and ERK2 phosphorylation is inhibited. These results indicate that the PSMGFR portion of the MUC1 receptor mediates cell growth and dimerization of the receptor can trigger this growth signal. These results support the conclusion that the portion of the MUC1 receptor that acts as a growth factor receptor is a cleavage product in which much or all of the IBR is released from the cell surface. Further, these results support the conclusion that tumors in which a good percentage of the MUC1 receptors have been cleaved to release the TPSIBR (SEQ ID NO: 18) are especially aggressive cancers and those that are cleaved to release the entire IBR, leaving PSMGFR (SEQ ID NO: 11) attached to the cell surface are even more aggressive. Therefore, antibodies that are raised against the TPSIBR (SEQ ID NO: 18) portion of the MUC1 receptor can be used to assess the aggressiveness of cancers that are MUC1-positive.

Consistent with these findings, the amount of MGFR that is accessible on cells (tissues) can be correlated with tumor aggressiveness and aggressive cell growth. Therefore, antibodies that recognize the MGFR portion of the receptor and have been shown to trigger MUC1-mediated cell growth can be used to promote cell growth in non-cancerous cells that express MUC1 wherein the PSMGFR portion of the receptor is accessible. Examples of such cells include but are not limited to stem cells, neutrophils, mast cells, and other immature cells.

Non-Tumor Cell Proliferation

In yet other embodiments, the invention provides methods for treating a subject for which stem cell or any progenitor cell would have therapeutic value, or other condition requiring treatment with one or more of the antibodies or antigen-binding fragments thereof of the invention. The method involves administering to the subject an antibody or antigen-binding fragment thereof in an amount effective to expand the stem cell or progenitor cell in the subject. In certain embodiments, any of the above-mentioned antibodies or antigen-binding fragments thereof, especially those which specifically bind to MGFR, PSMGFR, nat-PSMGFR and so on can be used. In certain preferred embodiments, the antibody or antigen-binding fragment thereof is administered in an amount effective to enhance the interaction of the MUC1 receptor for example, MGFR, that remains attached to a cell after shedding of an interchain binding region of the MUC1 receptor. In an embodiment of the method, particularly in which the antibody or antigen-binding fragment thereof specifically binds to MGFR, such a treatment method can involve administering to the subject the antibody or antigen-binding fragment thereof in an amount effective to cause inductive dimerization of a growth factor receptor, such as cleaved MUC1.

Immature Cell Expansion

Immature cells include somatic stem cells, embryonic stem cells, cord blood stem cells, and other not fully differentiated cells. Adult stem cells also known as somatic stem cells, are undifferentiated cells found among differentiated cells of a specific tissue and are mostly multipotent cells. They are already being used in treatments for over one hundred diseases and conditions. Certain adult stem cells termed "sporelike cells" are present in all tissues (Vacanti, M. P., A. Roy, J. Cortiella, L. Bonassar, and C. A. Vacanti. 2001, *J Cell Biochem* 80:455-60.). Embryonic stem cells are cultured cells obtained from the undifferentiated inner mass cells of an early stage human embryo are totipotent. Cord blood stem cells are derived from the blood of the placenta and umbilical cord after birth. Cord blood stem cells are used to treat without limitation Gunther's disease, Hunter syndrome, Hurler syndrome, Acute lymphocytic leukemia.

Allogeneic treatment is contemplated in the present invention.

Moreover, in particular, bone marrow contains two types of stem cells: hematopoietic (which can produce blood cells) and stromal (which can produce fat, cartilage and bone). Stromal stem cells have the capability to differentiate into many kinds of tissues, such as nervous tissue. Hematopoietic stem cells give rise to the three classes of blood cell that are found in the circulation: leukocytes, red blood cells (erythrocytes), and platelets (thrombocytes). Pluripotential hemopoietic stem cells or pluripotential hematopoietic stem cells (PHSCs) are stem cells found in the bone marrow. PHSC are the precursor cells which give rise to all the blood cell types of both the myeloid and lymphoid lineages. This includes monocytes and macrophages, neutrophils, basophils, eosinophils, T-cells, B-cells, NK-cells, microglia, erythrocytes (red blood cells), megakaryocytes (e.g. platelets), and dendritic cells.

As discussed herein, a proteolyzed form of the MUC1 receptor functions as a primal growth factor receptor to drive the proliferation of a number of cell types, including but not limited to immature cell types such as stem cells and progenitor cells. Table 3 lists the cell types that are known to express MUC1 and treatments for which methods of the invention would be suitable. Additionally, cell types that do not express MUC1 could be stimulated to proliferate by genetically manipulating the cells to express MUC1 or a MUC1 truncation mutant and then applying methods of the invention to stimulate the MUC1 receptor and induce or enhance cell proliferation.

Antibodies

Peptides used for antibody production may or may not be glycosylated prior to immunizing animals. The sequence of these peptides need not exactly reflect the sequence of MUC1 receptor as it exists in the general population. For example, the inventors observed that antibodies raised against the PSMGFR peptide variant var-PSMGFR (SEQ ID NO: 12), having an "-SPY-" motif have a higher affinity and greater specificity for the MUC1 protein than antibodies raised against the actual native sequence (i.e. nat-PSMGFR, SEQ ID NO: 10), having an "-SRY-" motif. One may also, in certain embodiments, introduce mutations into the PSMGFR peptide sequence to produce a more rigid peptide that may enhance antibody production. For example the R to P mutation in the var-PFMGFR sequence of SEQ ID NO: 12 may actually have provided a more rigid peptide and was thus more immunogenic. Another method for producing antibodies against regions of peptides that are not particularly immunogenic, such as the IBR or TPSIBR is to tag the specific peptide sequence with an irrelevant sequence in which the amino acids are of the D-form and thus act to stimulate the immune response of the host animal. Peptide sequences that are used to immunize animals for antibody production may also be glycosylated. The MUC1 peptide sequences that were used herein for drug screening and to generate cognate antibodies were derived from the human species of MUC1. Since there is considerable conservation across species for the PSMGFR and IBR and some portions of the UR, it is anticipated that MUC1 peptides whose sequences are derived from other species can also be used in drug screens and to generate antibodies for these same purposes.

In certain aspects, the invention provides antibodies or antigen-binding fragments thereof. In one embodiment, the invention provides an antibody or antigen-binding fragment that specifically binds to MGFR. In certain embodiments, the above-mentioned antibodies or antigen-binding fragments thereof specifically bind to PSMGFR. In certain such embodiments, the antibodies or antigen-binding fragments thereof can specifically bind to the amino acid sequence set forth in SEQ ID NO: 10 or a functional variant or fragment thereof comprising up to 15 amino acid additions or deletions at its N-terminus or comprising up to 20 amino acid substitutions; in other embodiments, it specifically binds to the amino acids set forth in SEQ ID NO: 10 or a functional variant or fragment thereof comprising up to 10 amino acid substitutions; in other embodiments, the antibodies or antigen-binding fragments thereof specifically bind to the amino acid set forth in SEQ ID NO: 10 or a functional variant or fragment thereof comprising up to 5 amino acid substitutions; and in yet another embodiments the antibodies or antigen-binding fragments thereof specifically bind to the amino acid sequence set forth in SEQ ID NO: 10. In certain embodiments, the antibody or antigen-binding fragment of the invention is a human, humanized, xenogenic or a chimeric human-non-human antibody or antigen-binding fragment thereof. In certain embodiments, the antibodies or antigen-binding fragments thereof of the invention comprise an intact antibody or an intact single-chain antibody. For antibodies or antigen-binding fragments that are monovalent, in certain embodiments, they may comprise a single-chain Fv fragment, a Fab' fragment, a Fab fragment, or a Fd fragment. For antibodies or antigen-binding fragments of the invention that are bivalent, certain embodiments comprise an antigen-binding fragment that is a F(ab')$_2$. In certain such compositions, the antibody or antigen-binding fragment thereof can be polyclonal, while in other embodiments it can be monoclonal.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

As is now well known in the art, the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. See, e.g., U.S. Pat. Nos. 4,816,567, 5,225,539, 5,585,089, 5,693,762 and 5,859,205, which are incorporated by reference herein in their entirety. Such antibodies, or fragments thereof are within the scope of the present invention.

In certain embodiments, fully human monoclonal antibodies also can be prepared by immunizing mice transgenic for large portions of human immunoglobulin heavy and light chain loci. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (HAMA) responses when administered to humans.

In certain embodiments the present invention comprises methods for producing the inventive antibodies, or antigen-binding fragments thereof, that include any one of the step(s) of producing a chimeric antibody, humanized antibody, single-chain antibody, Fab-fragment, F(ab')$_2$ fragment, bi-specific antibody, fusion antibody, labeled antibody or an analog of any one of those. Corresponding methods are known to the person skilled in the art and are described, e.g., in Harlow and Lane "Antibodies, A Laboratory Manual", CSH Press, Cold Spring Harbor, 1988. The production of chimeric antibodies is described, for example, in WO089/09622. Methods for the production of humanized antibodies are described in, e.g., EP-A1 0 239 400 and WO90/07861. A further source of antibodies to be utilized in accordance with the present invention are so-called xenogeneic antibodies. The general principle for the production of xenogeneic antibodies such as human antibodies in mice is described in, e.g., WO 91/10741, WO 94/02602, WO 96/34096 and WO 96/33735. As discussed below, the antibodies, of the invention may exist in a variety of forms (besides intact antibodies; including, for example, antigen binding fragments thereof, such as Fv, Fab and F(ab')2, as well as in single chains (i.e. as single chain antibodies); see e.g., WO088/09344.

Thus, as will be apparent to one of ordinary skill in the art, the present invention also provides, in certain embodiments, for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

Chemical Derivatives of Antibodies and Formulations

In certain embodiments, the present invention relates to compositions comprising the aforementioned antibodies or antigen-binding fragments of the invention or chemical derivatives thereof. The composition of the present invention may further comprise a pharmaceutically acceptable carrier. The term "chemical derivative" describes a molecule that contains additional chemical moieties that are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as *Remington's Pharmaceutical Sciences*.

Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical or intradermal administration. Aerosol formulations such as nasal spray formulations include purified aqueous or other solutions of the active agent with preservative agents and isotonic agents. Such formulations are preferably adjusted to a pH and isotonic state compatible with the nasal mucous membranes, e.g., for intranasal administration. Formulations for rectal or vaginal administration may be presented as a suppository with a suitable carrier.

A therapeutically effective dose refers to that amount of antibodies and/or antigen-binding fragments of the invention ameliorate the symptoms or conditions of the disease being treated. Therapeutic efficacy and toxicity of such compositions can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

The biological activity of the antibodies and/or antigen binding fragments thereof, of the invention indicates that they may have sufficient affinity to make them candidates for drug localization to cells expressing the appropriate surface structures, e.g. MGFR. Thus, targeting and binding to cells of the antibodies and/or antigen binding fragments thereof, of the invention could be useful for the delivery of therapeutically or diagnostically active agents (including targeting drugs, DNA sequences, RNA sequences, lipids, proteins and gene therapy/gene delivery. Thus, the antibody and/or antigen binding fragments thereof, of the invention can be labeled (e.g., fluorescent, radioactive, enzyme, nuclear magnetic, colloid, other signaling entity, etc.) and used to detect specific targets in vivo or in vitro including "immunochemistry" like assays in vitro. In vivo they could be used in a manner similar to nuclear medicine imaging techniques to detect tissues, cells, or other material expressing MGFR. Another method of the invention involves using antibodies that bind to the MGFR portion of the MUC1 receptor as a method for sorting and/or isolating cells that need to be expanded. Once sorted, these cells would be expanded in vitro. New genetic material, for example that codes for co-receptors and/or activating ligands, may be added to these selected cells either before or after expansion. Activating antibodies may be depleted from the cell population before introduction to the subject. Yet another method involves delivering a therapeutically active agent to a patient. The method includes administering at least one antibody or an antigen-binding fragment thereof and the therapeutically active agent to a patient. Preferably, the therapeutically active agent is selected from drugs, DNA sequences, RNA sequences, proteins, lipids, and combinations thereof.

Proteins

According to another aspect of the invention, a series of isolated proteins or peptides is provided. Inventive peptides may include, but are not limited to, those defined above as PSMGFR and PSMGFRTC, and those listed as SEQ ID NOS: 2-19. Additionally, the invention encompasses any protein, or peptide, not specifically mentioned above that is encoded by any of the isolated nucleic acid molecules of the invention discussed below. The invention also encompasses unique fragments of the above-mentioned proteins or peptides, as well as antibodies made against them, including monoclonal or polyclonal antibodies.

Proteins can be isolated from biological samples including tissue or cell homogenates, and can also be expressed recombinantly in a variety of prokaryotic and eukaryotic expression systems by constructing an expression vector appropriate to the expression system, introducing the expression vector into the expression system, and isolating the recombinantly expressed protein. Short polypeptides, including antigenic peptides (such as are presented by MHC molecules on the surface of a cell for immune recognition) also can be synthesized chemically using well-established methods of peptide synthesis.

The invention also encompasses unique fragments of the inventive proteins or peptides, which in one aspect, are used to generate antibodies. A fragment of any one of the inventive proteins or peptides, for example, generally has the features and characteristics of fragments including unique fragments as discussed herein in connection with nucleic acid molecules. As will be recognized by those skilled in the art, the size of a fragment which is unique will depend upon factors such as whether the fragment constitutes a portion of a conserved protein domain. Thus, some regions of the inventive proteins or peptides will require longer segments to be unique while others will require only short segments, typically between 5 and 12 amino acids (e.g. 5, 6, 7, 8, 9, 10, 11, and 12 amino acids long).

Unique fragments of a protein preferably are those fragments which retain a distinct functional capability of the protein. Functional capabilities which can be retained in a fragment of a protein include interaction with antibodies, interaction with other proteins or fragments thereof, selective binding of nucleic acid molecules, and enzymatic activity. One important activity is the ability to act as a signature for identifying the polypeptide.

Those skilled in the art are well versed in methods for selecting unique amino acid sequences, typically on the basis of the ability of the fragment to selectively distinguish the sequence of interest from non-family members. A comparison of the sequence of the fragment to those on known data bases typically is all that is necessary.

The invention embraces variants of the inventive proteins or peptides described herein. As used herein, a "variant" of a protein is a protein which contains one or more modifications to the primary amino acid sequence of such protein. Modifications which create a protein variant can be made to such protein 1) to produce, increase, reduce, or eliminate-an activity of the protein; 2) to enhance a property of the protein, such as protein stability in an expression system or the stability of protein-protein binding; 3) to provide a novel activity or property to a protein, such as addition of an antigenic epitope or addition of a detectable moiety; and/or 4) to provide equivalent or better binding to a ligand molecule. Modifications to a protein can be made via modifications to the nucleic acid molecule which encodes the protein, and can include deletions, point mutations, truncations, amino acid substitutions and additions of amino acids or non-amino acid moieties. Alternatively, modifications can be made directly to the protein, such as by cleavage, substitution of one or more amino acids during chemical synthesis, addition of a linker molecule, addition of a detectable moiety, such as biotin, addition of a fatty acid, etc. Modifications also embrace fusion proteins comprising all or part of an amino acid sequence of the invention. One of skill in the art will be familiar with methods for predicting the effect on protein conformation of a change in amino acid sequence, and can thus "design" a variant polypeptide according to known methods. One example of such a method is described by Dahiyat and Mayo in Science 278:82-87, 1997, whereby proteins can be designed de novo. The method can be applied to a known protein to vary only a portion of the protein sequence. By applying the computational methods of Dahiyat and Mayo, specific variants of a DOS protein can be proposed and tested to determine whether the variant retains a desired conformation.

The skilled artisan will also realize that certain amino acid substitutions, such as for example conservative amino acid substitutions, may be made in the inventive proteins or peptides to provide "functional variants" of the foregoing proteins or peptides, i.e, variants which possess functional capabilities of the corresponding inventive proteins or peptides. As used herein, a "conservative amino acid substitution" refers to an amino acid substitution which does not alter the relative charge or size characteristics of the protein in which the amino acid substitution is made. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Functional variants having up to 1, 2, 3, 4, 5, 6, 7, 8, 9, 10, 11, 12, 13, 14, 15, 16, 17, 18, 19, 20, or more amino acid substitutions can be made. Similarly, the above or other functional variants can be prepared having, or also having, up to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more amino acid additions or deletions at their C- and/or N-terminus. Variants of the proteins or peptides prepared by the foregoing methods can be sequenced, if desired, to determine the amino acid sequence and thus deduce the nucleotide sequence which encodes such variants.

Nucleic Acid

The present invention in another aspect provides nucleic acid sequences encoding a variety of truncated MUC1 receptor proteins, or functional variants or fragments thereof, and other nucleic acid sequences that hybridize to the above nucleic acid sequences under high stringency conditions. The sequence of certain of the nucleic acid molecules of the present invention are presented in Table 2 below as SEQ ID NOS: 21-25, and the predicted amino acid sequences of these genes' protein products, each comprising an isoform of a truncated MUC1 receptor protein, are presented in Table 1. The invention thus involves in one aspect peptide sequences representing truncated isoforms of the MUC1 receptor, genes encoding those peptide sequences and functional modifications and variants of the foregoing, useful fragments of the foregoing, as well as therapeutic products and methods relating thereto. The peptides referred to herein as truncated MUC1 receptor proteins include fragments of the full length MUC1 receptor but do not include the full length MUC1 receptor protein (i.e. SEQ ID NO: 1). Likewise, nucleic acid molecules that encode the various truncated isoforms of the MUC1 receptor described herein can include fragments of the MUC1 gene coding region, but do not include the full length MUC1 coding region.

According to one embodiment of the invention, an isolated nucleic acid molecule is provided. The isolated nucleic acid molecule is selected from the group consisting of:

(a) nucleic acid molecules which encode the MUC1 truncated receptor isoform peptides listed as SEQ ID NOS: 5, 6, 7, 8, and 9 in Table 1, or functional variants or fragments thereof, including, for example, the nucleotide sequences: SEQ ID NOS: 21, 22, 23, 24, and 25, respectively, and (b) nucleic acid molecules which hybridize under highly stringent conditions to the nucleic acid molecules of (a), (c) deletions, additions and substitutions of the nucleic acid molecules of (a) or (b), (d) nucleic acid molecules that differ from the nucleic acid molecules of (a), (b) or (c) in codon sequence due to the degeneracy of the genetic code, and (e) complements of (a), (b), (c), or (d).

Certain isolated nucleic acids of the invention are nucleic acid molecules which encode a truncated isoform of the MUC1 receptor, or a functional fragment or variant thereof, or a functional equivalent thereof (e.g., a nucleic acid sequence encoding the same protein as encoded by one of the nucleic acid sequences, e.g. SEQ ID NO: 21, listed in Table 2, provided that the functional fragment or equivalent encodes a protein which exhibits the functional activity of a truncated isoform of the MUC1 receptor encoded by such a listed sequence. As used herein, the functional activity of the truncated isoforms of the MUC1 receptor refers to the ability of the truncated isoforms of the MUC1 receptor peptide sequence to specifically interact with ligands for MGFR and to modulate cell growth or cell proliferation in response to such interaction. In certain embodiments, the isolated nucleic acid molecule is SEQ ID NO: 21.

The invention provides nucleic acid molecules which hybridize under high stringency conditions to a nucleic acid molecule consisting of the nucleotide sequences set forth in SEQ ID NOS: 21-25. Such nucleic acids may be DNA, RNA, composed of mixed deoxyribonucleotides and ribonucleotides, or may also incorporate synthetic non-natural nucleotides. Various methods for determining the expression of a nucleic acid and/or a polypeptide in normal and tumor cells are known to those of skill in the art The term "highly stringent conditions" or "high stringency conditions" as used herein refers to parameters with which those skilled in the art are familiar. Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, stringent conditions, as used herein, refers, for example, to hybridization at 65° C. in hybridization buffer (3.5×SSC, 0.02% Ficoll, 0.02% polyvinyl pyrrolidone, 0.02% Bovine Serum Albumin, 2.5 mM NaH2PO4 (pH 7), 0.5% SDS, 2 mM EDTA). SSC is 0.15M sodium chloride/0.15M sodium citrate, pH 7; SDS is sodium dodecyl sulphate; and EDTA is ethylenediaminetetracetic acid. After hybridization, the membrane upon which the DNA is transferred is washed at 2×SSC at room temperature and then at 0.1×SSC/0.1×SDS at temperatures up to 68° C.

In general, homologs and alleles of a specific SEQ ID NO enumerated herein (see Table 2) typically will share at least 40% nucleotide identity and/or at least 50% amino acid identity to such a nucleotide sequence or amino acid sequence, respectively, in some instances will share at least 50% nucleotide identity and/or at least 65% amino acid identity and in still other instances will share at least 60% nucleotide identity and/or at least 75% amino acid identity. Preferred homologs and alleles share nucleotide and amino acid identities with SEQ ID NO: 21 and SEQ ID NO: 5, respectively; or SEQ ID NO: 22 and SEQ ID NO: 6, respectively; or SEQ ID NO: 23 and SEQ ID NO: 7, respectively; or SEQ ID NO: 24 and SEQ ID NO: 8, respectively; or SEQ ID NO: 25 and SEQ ID NO: 9, respectively; and encode polypeptides of greater than 80%, more preferably greater than 90%, still more preferably greater than 95% and most preferably greater than 99% identity. The percent identity can be calculated using various, publicly available software tools developed by NCBI (Bethesda, Md.) that can be obtained through the internet (ftp:/ncbi.nlm.nih.gov/pub/). Exemplary tools include the BLAST system available at http://www.ncbi.nlm.nih.gov, which uses algorithms developed by Altschul et al. (*Nucleic Acids Res.* 25:3389-3402, 1997). Pairwise and ClustalW alignments (BLOSUM30 matrix setting) as well as Kyte-Doolittle hydropathic analysis can be obtained using the MacVector sequence analysis software (Oxford Molecular Group). Watson-Crick complements of the foregoing nucleic acid molecules also are embraced by the invention.

The invention also provides isolated unique fragments of SEQ ID NOS: 21-25 and/or complements of SEQ ID NOS: 21-25. A unique fragment is one that is a 'signature' for the larger nucleic acid. It, for example, is long enough to assure that its precise sequence is not found in molecules outside of the inventive nucleic acid molecules defined above. Those of ordinary skill in the art may apply no more than routine procedures to determine if a fragment is unique within the human or mouse genome.

As will be recognized by those skilled in the art, the size of the above-mentioned unique fragment will depend upon its conservancy in the genetic code. Thus, some regions of SEQ ID NOS: 21-25 and their complements will require longer segments to be unique while others will require only short segments, typically between 12 and 32 nucleotides or more in length (e.g. 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115 or more), up to the entire length of the disclosed sequence. Many segments of the polynucleotide coding region or complements thereof that are 18 or more nucleotides in length will be unique. Those skilled in the art are well versed in methods for selecting such sequences, typically on the basis of the ability of the unique fragment to selectively distinguish the sequence of interest from other, unrelated nucleic acid molecules. A comparison of the sequence of the fragment to those on known data bases typically is all that is necessary, although in vitro confirmatory hybridization and sequencing analysis may be performed.

As used herein, a "vector" may be any of a number of nucleic acid molecules into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase.

An "expression vector" is one into which a desired DNA sequence may be inserted by restriction and ligation such that it is operably joined to regulatory sequences and may be expressed as an RNA transcript. Vectors may further contain one or more marker sequences suitable for use in the identification of cells that have or have not been transformed or transfected with the vector. Markers include, for example, genes encoding proteins that increase or decrease either resistance or sensitivity to antibiotics or other compounds, genes that encode enzymes whose activities are detectable by standard assays known in the art (e.g., β-galactosidase or alkaline phosphatase), and genes that visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide. The precise nature of the regulatory sequences needed for gene expression may vary between species or cell types and are well-known to those of skill in the art.

Gene Therapy

In a specific embodiment, nucleic acids comprising sequences encoding MUC1, a fragment of MUC1 that is displayed on the cell surface, or the MGFR portion of MUC1 polypeptide are administered to treat, inhibit or prevent a disease or disorder in which immature cell therapy will benefit the patient, by way of gene therapy. Gene therapy refers to therapy performed by the administration to a subject of an expressed or expressible nucleic acid. In this embodiment of the invention, the nucleic acids produce their encoded protein that mediates a therapeutic effect by stimulating the proliferation of immature cells expressing MUC1.

Further, in an alternative embodiment, gene G-CSF receptor may be co-expressed for therapeutic purposes to stimulate proliferation of immature cells.

Any of the methods for gene therapy available in the art can be used according to the present invention. Exemplary methods are described below.

For general reviews of the methods of gene therapy, see Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 11(5):155-215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, nucleic acid sequences may encode a MUC1, a fragment of MUC1 that is displayed on the cell surface, or the MGFR portion of MUC1 polypeptide, in which the nucleic acid sequences are part of expression vectors that express the polypeptides in a suitable host. In particular, such nucleic acid sequences have promoters operably linked to the polypeptide coding region, said promoter being inducible or constitutive, and, optionally, tissue-specific. In another particular embodiment, nucleic acid molecules are used in which the polypeptide coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932-8935 (1989); Zijlstra et al., Nature 342:435-438 (1989).

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors, or by direct injection of naked DNA, or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors) and so on. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor. Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijlstra et al., Nature 342:435-438 (1989)).

In a specific embodiment, viral vectors that contain nucleic acid sequences encoding the polypeptide are used. The nucleic acid sequences encoding the polypeptide to be used in gene therapy are cloned into one or more vectors, which facilitates delivery of the gene into a patient. Retroviral vectors, adenoviral vectors and adeno-associated viruses are examples of viral vectors that may be used. Retroviral vectors contain the components necessary for the correct packaging of the viral genome and integration into the host cell DNA.

Adenoviruses are especially attractive vehicles for delivering genes to respiratory epithelia because they naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. In addition, adeno-associated virus (AAV) has also been proposed for use in gene therapy.

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion and so on. Numerous techniques are known in the art for the introduction of foreign genes into cells and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T-lymphocytes, B-lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, and so on.

The cell used for gene therapy may be autologous or allogeneic. In a preferred embodiment, the cell used for gene therapy is autologous to the patient.

In an embodiment in which recombinant cells are used in gene therapy, nucleic acid sequences encoding the polypeptide are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention.

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

In some embodiments, a virus vector for delivering a nucleic acid molecule encoding a peptide sequence of the invention is selected from the group consisting of adenoviruses, adeno-associated viruses, poxviruses including vaccinia viruses and attenuated poxviruses, Semliki Forest virus, Venzuelan equine encephalitis virus, retroviruses, Sindbis virus, and Ty virus-like particle. Examples of viruses and virus-like particles which have been used to deliver exogenous nucleic acids include: replication-defective adenoviruses (e.g., Xiang et al., *Virology* 219:220-227, 1996; Eloit et al., *J. Virol.* 7:5375-5381, 1997; Chengalvala et al., *Vaccine* 15:335-339, 1997), a modified retrovirus (Townsend et al., *J. Virol.* 71:3365-3374, 1997), a nonreplicating retrovirus (Irwin et al., *J. Virol.* 68:5036-5044, 1994), a replication defective Semliki Forest virus (Zhao et al., *Proc. Natl. Acad. Sci. USA* 92:3009-3013, 1995), canarypox virus and highly attenuated vaccinia virus derivative (Paoletti, *Proc. Natl. Acad. Sci. USA* 93:11349-11353, 1996), non-replicative vaccinia virus (Moss, *Proc. Natl. Acad. Sci. USA* 93:11341-11348, 1996), replicative vaccinia virus (Moss, *Dev. Biol. Stand.* 82:55-63, 1994), Venzuelan equine encephalitis virus (Davis et al., *J. Virol.* 70:3781-3787, 1996), Sindbis virus (Pugachev et al., *Virology* 212:587-594, 1995), and Ty virus-like particle (Allsopp et al., *Eur. J. Immunol* 26:1951-1959, 1996). In certain embodiments, the virus vector is an adenovirus.

Another virus, which can potentially be used for certain applications, is the adeno-associated virus, a double-stranded DNA virus. The adeno-associated virus is capable of infecting a wide range of cell types and species and can be engineered to be replication-deficient. It further has advantages, such as heat and lipid solvent stability, high transduction frequencies in cells of diverse lineages, including hematopoietic cells, and lack of superinfection inhibition thus allowing multiple series of transductions. The adeno-associated virus can integrate into human cellular DNA in a site-specific manner, thereby minimizing the possibility of insertional mutagenesis and variability of inserted gene expression. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion Other viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Adenoviruses and retroviruses have been approved for human gene therapy trials. In general, the retroviruses are replication-deficient (i.e., capable of directing synthesis of the desired proteins, but incapable of manufacturing an infectious particle). Such genetically altered retroviral expression vectors can have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., *Gene Transfer and Expression, A Laboratory Manual*, W.H. Freeman Co., New York (1990) and Murry, E. J. Ed. "Methods in Molecular Biology," vol. 7, Humana Press, Inc., Cliffion, N.J. (1991)

Various techniques may be employed for introducing nucleic acid molecules of the invention into cells, depending on whether the nucleic acid molecules are introduced in vitro or in vivo in a host. Such techniques include transfection of nucleic acid molecule-calcium phosphate precipitates, transfection of nucleic acid molecules associated with DEAE, transfection or infection with the foregoing viruses including the nucleic acid molecule of interest, liposome-mediated transfection, and the like.

For certain uses, it is preferred to target the nucleic acid molecule to particular cells. In such instances, a vehicle used for delivering a nucleic acid molecule of the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid molecule delivery vehicle. Especially preferred are monoclonal antibodies. Where liposomes are employed to deliver the nucleic acid molecules of the invention, proteins that bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acid molecules into cells, as is known by those skilled in the art. Such systems even permit oral delivery of nucleic acid molecules.

In addition to delivery through the use of vectors, nucleic acids of the invention may be delivered to cells without vectors, e.g. as "naked" nucleic acid delivery using methods known to those of skill in the art.

Transgenic Animal

According to another aspect of the invention, a transgenic non-human animal comprising an expression vector of the invention is provided. As used herein, "transgenic non-human animals" includes non-human animals having one or more exogenous nucleic acid molecules incorporated in germ line cells and/or somatic cells. Thus the transgenic animals include animals having episomal or chromosomally incorporated expression vectors, etc. In general, such expression vectors can use a variety of promoters which confer the desired gene expression pattern (e.g., temporal or spatial). Conditional promoters also can be operably linked to nucleic acid molecules of the invention to increase or decrease expression of the encoded polypeptide molecule in a regulated or conditional manner. Trans-acting negative or positive regulators of polypeptide activity or expression also can be operably linked to a conditional promoter as described above.

Administration and Dosage

When used therapeutically, the agents of the invention are administered in therapeutically effective amounts. In general, a therapeutically effective amount means that amount necessary to delay the onset of, inhibit the progression of, or halt altogether the particular condition being treated. Generally, a therapeutically effective amount will vary with the subject's age, condition, and sex, as well as the nature and extent of the disease in the subject, all of which can be determined by one of ordinary skill in the art. The dosage may be adjusted by the individual physician or veterinarian, particularly in the event of any complication. A therapeutically effective amount typically varies from 0.01 mg/kg to about 1000 mg/kg. It is expected that dose ranging from 1-500 mg/kg, and preferably doses ranging from 1-50 mg/kg will be suitable. In other embodiments, the agents will be administered in doses ranging from 1 µg/kg/day to 10 mg/kg/day, with even more preferred doses ranging from 1-200 µg/kg/day, 1-100 µg/kg/day, 1-50 µg/kg/day or from 1-25 µg/kg/day. In other embodiments, dosages may range from about 0.1 mg/kg to about 200 mg/kg, and most preferably from about 0.2 mg/kg to about 20 mg/kg. These dosages can be applied in one or more dose administrations daily, for one or more days.

The agent of the invention should be administered for a length of time sufficient to provide either or both therapeutic and prophylactic benefit to the subject. Generally, the agent is administered for at least one day. In some instances, the agent may be administered for the remainder of the subject's life. The rate at which the agent is administered may vary depending upon the needs of the subject and the mode of administration. For example, it may be necessary in some instances to administer higher and more frequent doses of the agent to a subject for example during or immediately following a event associated with tumor or cancer, provided still that such doses achieve the medically desirable result. On the other hand, it may be desirable to administer lower doses in order to maintain the medically desirable result once it is achieved. In still other embodiments, the same dose of agent may be administered throughout the treatment period which as described herein may extend throughout the lifetime of the subject. The frequency of administration may vary depending upon the characteristics of the subject. The agent may be administered daily, every 2 days, every 3 days, every 4 days, every 5 days, every week, every 10 days, every 2 weeks, every month, or more, or any time there between as if such time was explicitly recited herein.

In one embodiment, daily doses of active agents will be from about 0.01 milligrams/kg per day to 1000 milligrams/kg per day. It is expected that oral doses in the range of 50 to 500 milligrams/kg, in one or several administrations per day, will yield the desired results. Dosage may be adjusted appropriately to achieve desired levels, local or systemic, depending upon the mode of administration. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of agents.

Preferably, such agents are used in a dose, formulation and administration schedule which favor the activity of the agent and do not impact significantly, if at all, on normal cellular functions.

In one embodiment, the degree of activity of the agent is at least 10%. In other embodiments, the degree of activity of the drug is as least 20%, at least 30%, at least 40%, at least 50%, at least 60%, at least 70%, at least 80%, at least 90%, or at least 95%.

When administered to subjects for therapeutic purposes, the formulations of the invention are applied in pharmaceutically acceptable amounts and in pharmaceutically acceptable compositions. Such a pharmaceutical composition may include the agents of the invention in combination with any standard physiologically and/or pharmaceutically acceptable carriers which are known in the art. The compositions should be sterile and contain a therapeutically effective amount of the agent in a unit of weight or volume suitable for administration to a patient. The term "pharmaceutically-acceptable carrier" as used herein means one or more compatible solid or liquid filler, diluents or encapsulating substances which are suitable for administration into a human or other animal. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy. Pharmaceutically acceptable further means a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

Such preparations may routinely contain salts, buffering agents, preservatives, compatible carriers, and optionally other therapeutic ingredients. When used in medicine the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulphuric, nitric, phosphoric, maleic, acetic, salicylic, p-toluene sulfonic, tartaric, citric, methane sulfonic, formic, malonic, succinic, naphthalene-2-sulfonic, and benzene sulfonic. Also, pharmaceutically acceptable salts can be prepared as alkaline metal or alkaline earth salts, such as sodium, potassium or calcium salts of the carboxylic acid group Suitable buffering agents include: acetic acid and a salt (1-2% W/V); citric acid and a salt (1-3% W/V); boric acid and a salt (0.5-2.5% WIN); and phosphoric acid and a salt (0.8-2% W/V)

Suitable preservatives include benzalkonium chloride (0.003-0.03% W/V); chlorobutanol (0.3-0.9% W/V); parabens (0.01-0.25% W/V) and thimerosal (0.004-0.02% W/V)

A variety of administration routes are available. The particular mode selected will depend, of course, upon the particular combination of drugs selected, the severity of the disease condition being treated, the condition of the patient, and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, topical, nasal, other mucosal forms, direct injection, transdermal, sublingual or other routes. "Parenteral" routes include subcutaneous, intravenous, intramuscular, or infusion. Direct injection may be preferred for local delivery to the site of the cancer. Oral administration may be preferred for prophylactic treatment e.g., in a subject at risk of developing a cancer, because of the convenience to the patient as well as the dosing schedule.

Chemical/physical vectors may be used to deliver the agents of the invention to a target (e.g. cell) and facilitate uptake thereby. As used herein, a "chemical/physical vector" refers to a natural or synthetic molecule, other than those derived from bacteriological or viral sources, capable of delivering the agent of the invention to a target (e.g. cell).

A preferred chemical/physical vector of the invention is a colloidal dispersion system. Colloidal dispersion systems include lipid-based systems including oil-in-water emulsions, micelles, mixed micelles, and liposomes. A preferred colloidal system of the invention is a liposome. Liposomes are artificial membrane vessels which are useful as a delivery vector in vivo or in vitro. It has been shown that large unilamellar vessels (LUV), which range in size from 0.2-4.0 µm can encapsulate large macromolecules. RNA, DNA, and intact virions can be encapsulated within the aqueous interior and be delivered to cells in a biologically active form (Fraley, et al., Trends Biochem. Sci., v. 6, p. 77 (1981)). In order for a liposome to be an efficient gene transfer vector, one or more of the following characteristics should be present: (1) encapsulation of the gene of interest at high efficiency with retention of biological activity; (2) preferential and substantial binding to a target cell in comparison to non-target cells; (3) delivery of the aqueous contents of the vesicle to the target cell cytoplasm at high efficiency; and (4) accurate and effective expression of genetic information.

Liposomes may be targeted to a particular (e.g. tissue), such as (e.g. the vascular cell wall), by coupling the liposome to a specific ligand such as a monoclonal antibody, sugar, glycolipid, or protein.

Liposomes are commercially available from Gibco BRL, for example, as LIPOFECTIN™ and LIPOFECTACE™., which are formed of cationic lipids such as N-[1-(2,3 dioleyloxy)-propyl]-N, N, N-trimethylammonium chloride (DOTMA) and dimethyl dioctadecylammonium bromide (DDAB). Methods for making liposomes are well known in the art and have been described in many publications. Liposomes also have been reviewed by Gregoriadis, G. in Trends in Biotechnology, V. 3, p. 235-241 (1985).

In one particular embodiment, the preferred vehicle is a biocompatible micro particle or implant that is suitable for implantation into the mammalian recipient. Exemplary bioerodible implants that are useful in accordance with this method are described in PCT International application no. PCT/US/03307 (Publication No. WO 95/24929, entitled "Polymeric Gene Delivery System", claiming priority to U.S. patent application Ser. No. 213,668, filed Mar. 15, 1994). PCT/US/0307 describes a biocompatible, preferably biodegradable polymeric matrix for containing an exogenous gene under the control of an appropriate promoter. The polymeric matrix is used to achieve sustained release of the exogenous gene in the patient. In accordance with the instant invention, the agent of the invention is encapsulated or dispersed within the biocompatible, preferably biodegradable polymeric matrix disclosed in PCT/US/03307. The polymeric matrix preferably is in the form of a micro particle such as a micro sphere (wherein the agent is dispersed throughout a solid polymeric matrix) or a microcapsule (wherein the agent is stored in the core of a polymeric shell). Other forms of the polymeric matrix for containing the agents of the invention include films, coatings, gels, implants, and stents. The size and composition of the polymeric matrix device is selected to result in favorable release kinetics in the tissue into which the matrix device is implanted. The size of the polymeric matrix devise further is selected according to the method of delivery which is to be used, typically injection into a tissue or administration of a suspension by aerosol into the nasal and/or pulmonary areas. The polymeric matrix composition can be selected to have both favorable degradation rates and also to be formed of a material which is bioadhesive, to further increase the effectiveness of transfer when the devise is administered to a vascular surface. The matrix composition also can be selected not to degrade, but rather, to release by diffusion over an extended period of time.

Both non-biodegradable and biodegradable polymeric matrices can be used to deliver agents of the invention of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

In general, the agents of the invention are delivered using the bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in Macromolecules, 1993, 26, 581-587, the teachings of which are incorporated herein by reference, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate). Thus, the invention provides a composition of the above-described agents for use as a medicament, methods for preparing the medicament and methods for the sustained release of the medicament in vivo.

The compositions may conveniently be presented in unit dosage form and may be prepared by any of the methods well known in the art of pharmacy. All methods include the step of bringing the therapeutic agents into association with a carrier which constitutes one or more accessory ingredients. In general, the compositions are prepared by uniformly and intimately bringing the therapeutic agent into association with a liquid carrier, a finely divided solid carrier, or both, and then, if necessary, shaping the product Compositions suitable for parenteral administration conveniently comprise a sterile aqueous preparation of the therapeutic agent, which is preferably isotonic with the blood of the recipient. This aqueous preparation may be formulated according to known methods using those suitable dispersing or wetting agents and suspending agents. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono or di-glycerides. In addition, fatty acids such as oleic acid find use in the preparation of injectables. Carrier formulations suitable for oral, subcutaneous, intravenous, intramuscular, etc. can be found in Remington's Pharmaceutical Sciences, Mack Publishing Company, Easton, Pa.

Compositions suitable for oral administration may be presented as discrete units such as capsules, cachets, tablets, or lozenges, each containing a predetermined amount of the therapeutic agent. Other compositions include suspensions in aqueous liquors or non-aqueous liquids such as a syrup, an elixir, or an emulsion Other delivery systems can include time-release, delayed release or sustained release delivery systems. Such systems can avoid repeated administrations of the therapeutic agent of the invention, increasing convenience to the subject and the physician. Many types of release delivery systems are available and known to those of ordinary skill in the art. They include polymer based systems such as polylactic and polyglycolic acid, poly(lactide-glycolide), copolyoxalates, polyanhydrides, polyesteramides, polyorthoesters, polyhydroxybutyric acid, and polycaprolactone. Microcapsules of the foregoing polymers containing drugs are described in, for example, U.S. Pat. No. 5,075,109. Nonpolymer systems that are lipids including sterols such as cholesterol, cholesterol esters and fatty acids or neutral fats such as mono-, di- and tri-glycerides; liposomes; phospholipids; hydrogel release systems; silastic systems; peptide based systems; wax coatings, compressed tablets using conventional binders and excipients, partially fused implants and the like. Specific examples include, but are not limited to: (a) erosional systems in which the polysaccharide is contained in a form within a matrix, found in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation Use of a long-term sustained release implant may be particularly suitable for treatment of established disease conditions as well as subjects at risk of developing the disease. "Long-term" release, as used herein, means that the implant is constructed and arranged to deliver therapeutic levels of the active ingredient for at least 7 days, and preferably 30-60 days. The implant may be positioned at a site of injury or the location in which tissue or cellular regeneration is desired. Long-term sustained release implants are well known to those of ordinary skill in the art and include some of the release systems described above The therapeutic agent may be administered in alone or in combination with other agents including proteins, receptors, co-receptors and/or genetic material designed to introduce into, upregulate or down regulate these genes in the area or in the cells. If the therapeutic agent is administered in combination the other agents may be administered by the same method, e.g. intravenous, oral, etc. or may be administered separately by different modes, e.g. therapeutic agent administered orally, administered intravenously, etc. In one embodiment of the invention the therapeutic agent and other agents are co-administered intravenously. In another embodiment the therapeutic agent and other agents are administered separately Other agents that can be co-administered with the compounds of the invention include, but are not limited to Acivicin; Aclarubicin; Acodazole Hydrochloride; Acronine; Adriamycin; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxol; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride. Additional antineoplastic agents include those disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc. (Health Professions Division).

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLES

Example 1

Antibody Production

Antibodies that bind to the MGFR portion of the MUC1 receptor, referred to herein as anti-PSMGFR are described in detail in PCT Application No. PCT/US2004/027954 (WO 2005/019269), in particular in Example 8 of the PCT Application. Antibody production is also described in PCT Application No. PCT/US2005/032821, in particular in Example 2 of the PCT Application. Inventive antibodies were raised against the PSMGFR portion of the MUC1 receptor, in particular nat-PSMGFR or var-PSMGFR shown in Table 1 using standard methods of antibody production. Rabbit polyclonal antibodies were produced and purified by column chromatography in which the immunizing peptide was attached to the chromatography column beads. The antibodies, anti-nat-PSMGFR and anti-var-PSMGFR, were shown to specifically and sensitively bind to the MGFR portion of the MUC1 receptor.

Example 2

Preparation of Tissue Specimens

Tissue specimens pictured in FIGS. 7-14 were prepared using methods previously described in PCT Application No. PCT/US2005/032821, in particular in Example 3 of the PCT Application. Formalin fixed, paraffin embedded tissue specimens were tested for reactivity to two antibodies that recognize different epitopes on the MUC1 receptor: 1) a rabbit polyclonal antibody, anti-PSMGFR, that binds to the PSMGFR portion of the MUC1 receptor that remains attached to the cell surface after receptor shedding; and 2) a commercially available mouse monoclonal, VU4H5 (Santa Cruz, Calif.) that binds to a sequence in the tandem repeat section of the receptor. One section from each block was stained with hemotoxin and eosin (H&E) to aid in assessing tumor grade.

Example 3

Induced Proliferation of MUC1-Presenting Cells

Methods used in FIGS. 2-4 are described in detail in PCT Application No. PCT/US2004/027954 (WO 2005/019269), in particular in Example 1 of the PCT Application. MUC1-positive cells were exposed to an inventive bivalent antibody grown against the MGFR region of the MUC1 receptor. Normalized cell growth was plotted as a function of antibody concentration. Bivalent antibodies were raised against either var-PSMGFR or nat-PSMGFR sequences shown in Table 1 (i.e., a single antibody having the ability to bind simultaneously to two MGFRs was produced). MUC1-positive breast tumor cells (T47Ds and 1504s), and a nat-PSMGFR transfected MUC1-negative cell line HEK293 were exposed to the antibody, and cell proliferation was studied as a function of concentration of the antibody. A growth/response curve typical of a growth factor/receptor—antibody response was observed. Specifically, at a concentration low enough that only a small portion of the cells were exposed to the antibody, cell proliferation was low. At a concentration of antibody high enough that one antibody could bind adjacent MGFRs, cell proliferation was maximized. At a high excess of antibody, each antibody bound only a single MGFR, rather than dimerizing adjacent MGFRs, and proliferation was reduced.

All of the references cited herein are incorporated by reference in their entirety.

Those skilled in the art will recognize, or be able to ascertain using no more than routine experimentation, many equivalents to the specific embodiments of the invention specifically described herein. Such equivalents are intended to be encompassed in the scope of the claims.

TABLE 1

Peptide sequences (listed from N-terminus to C-terminus):

Full-length MUC1 Receptor (Mucin 1 precursor, Genbank Accession number: P15941)
(SEQ ID NO: 1)
```
MTPGTQSPFF LLLLLTVLTV VTGSGHASST PGGEKETSAT
QRSSVPSSTE KNAVSMTSSV

LSSHSPGSGS STTQGQDVTL APATEPASGS AATWGQDVTS
VPVTRPALGS TTPPAHDVTS

APDNKPAPGS TAPPAHGVTS APDTRPAPGS TAPPAHGVTS
APDTRPAPGS TAPPAHGVTS

APDTRPAPGS TAPPAHGVTS APDTRPAPGS TAPPAHGVTS
APDTRPAPGS TAPPAHGVTS

APDTRPAPGS TAPPAHGVTS APDTRPAPGS TAPPAHGVTS
APDTRPAPGS TAPPAHGVTS

APDTRPAPGS TAPPAHGVTS APDTRPAPGS TAPPAHGVTS
APDTRPAPGS TAPPAHGVTS

APDTRPAPGS TAPPAHGVTS APDTRPAPGS TAPPAHGVTS
APDTRPAPGS TAPPAHGVTS

APDTRPAPGS TAPPAHGVTS APDTRPAPGS TAPPAHGVTS
APDTRPAPGS TAPPAHGVTS

APDTRPAPGS TAPPAHGVTS APDTRPAPGS TAPPAHGVTS
APDTRPAPGS TAPPAHGVTS

APDTRPAPGS TAPPAHGVTS APDTRPAPGS TAPPAHGVTS
APDTRPAPGS TAPPAHGVTS

APDTRPAPGS TAPPAHGVTS APDTRPAPGS TAPPAHGVTS
APDTRPAPGS TAPPAHGVTS

APDTRPAPGS TAPPAHGVTS APDTRPAPGS TAPPAHGVTS
APDTRPAPGS TAPPAHGVTS

APDTRPAPGS TAPPAHGVTS APDTRPAPGS TAPPAHGVTS
APDTRPAPGS TAPPAHGVTS

APDTRPAPGS TAPPAHGVTS APDTRPAPGS TAPPAHGVTS
APDNRPALGS TAPPVHNVTS
```

TABLE 1-continued

```
ASGSASGSAS TLVHNGTSAR ATTTPASKST PFSIPSHHSD
TPTTLASHST KTDASSTHHS

SVPPLTSSNH STSPQLSTGV SFFFLSFHIS

NLQFNSSLED PSTDYYQELQ RDISEMFLQI YKQGGFLGLS
NIKFRPGSVV VQLTLAFREG

TINVHDVETQ FNQYKTEAAS RYNLTISDVS VSDVPFPFSA
QSGAGVPGWG IALLVLVCVL

VALAIVYLIA LAVCQCRRKN YGQLDIFPAR DTYHPMSEYP
TYHTHGRYVP PSSTDRSPYE

KVSAGNGGSS LSYTNPAVAA ASANL
```

N-terminal MUC-1 signaling sequence for directing MUC1 receptor and truncated isoforms to cell membrane surface. Up to 3 amino acid residues may be absent at C-terminal end as indicated by variants in SEQ ID NOS: 2, 3 and 4.
(SEQ ID NO: 2)
```
MTPGTQSPFFLLLLLTVLT
```

(SEQ ID NO: 3)
```
MTPGTQSPFFLLLLLTVLT VVTA
```

(SEQ ID NO: 4)
```
MTPGTQSPFFLLLLLTVLT VVTG
```

A truncated MUC1 receptor isoform having nat-PSMGFR at its N-terminus and including the transmembrane and cytoplasmic sequences of a full-length MUC1 receptor ("nat-PSMGFRTC isoform"- An example of "PSMGFRTC"- shown excluding optional N-terminus signal sequence, which may be cleaved after translation and prior to expression of the receptor on the cell surface):
(SEQ ID NO: 5)
```
G TINVHDVETQ FNQYKTEAAS RYNLTISDVS VSDVPFPFSA
QSGAGVPGWG IALLVLVCVL

VALAIVYLIA LAVCQCRRKN YGQLDIFPAR DTYHPMSEYP
TYHTHGRYVP PSSTDRSPYE

KVSAGNGGSS LSYTNPAVAA ASANL
```

A truncated MUC1 receptor isoform having nat-PSMGFR and PSIBR at its N-terminus and including the transmembrane and cytoplasmic sequences of a full-length MUC1 receptor ("CM isoform"- shown excluding optional N-terminus signal sequence, which may be cleaved after translation and prior to expression of the receptor on the cell surface):
(SEQ ID NO: 6)
```
GFLGLS NIKFRPGSVV VQLTLAFREG TINVHDVETQ FNQYKTEAAS
RYNLTISDVS

VSDVPFPFSA QSGAGVPGWG IALLVLVCVL VALAIVYLIA
LAVCQCRRKN YGQLDIFPAR

DTYHPMSEYP TYHTHGRYVP PSSTDRSPYE KVSAGNGGSS
LSYTNPAVAA ASANL
```

A truncated MUC1 receptor isoform having nat-PSMGFR + PSIBR + Unique Region at its N-terminus and including the transmembrane and cytoplasmic sequences of a full-length MUC1 receptor ("UR isoform"- shown excluding optional N-terminus signal sequences):
(SEQ ID NO: 7)
```
ATTTPASKST PFSIPSHHSD TPTTLASHST KTDASSTHHS
TVPPLTSSNH

STSPQLSTGV SFFFLSFHIS NLQFNSSLED PSTDYYQELQ
RDISEMFLQI
```

TABLE 1-continued

```
YKQGGFLGLS NIKFRPGSVV VQLTLAFREG TINVHDVETQ
FNQYKTEAAS

RYNLTISDVS VSDVPFPFSA QSGAGVPGWG IALLVLVCVL
VALAIVYLIA

LAVCQCRRKN YGQLDIFPAR DTYHPMSEYP TYHTHGRYVP
PSSTDRSPYE KVSAGNGGSS

LSYTNPAVAA ASANL

A truncated MUC1 receptor isoform including the
transmembrane and cytoplasmic sequences of a full-
length MUC1 receptor ("Y isoform"- shown excluding
optional N-terminus signal sequence, which may be
cleaved after translation and prior to expression
of the receptor on the cell surface):
                                        (SEQ ID NO: 8)
GSGHASSTPG GEKETSATQR SSVPSSTEKN AFNSSLEDPS
TDYYQELQRD ISEMFLQIYK

QGGFLGLSNI KFRPGSVVVQ LTLAFREGTI NVHDMETQFN
QYKTEAASRY NLTISDVSVS

DVPFPFSAQS GAGVPGWGIA LLVLVCVLVA LAIVYLIALA
VCQCRRKNYG QLDIFPARDT

YHPMSEYPTY HTHGRYVPPS STDRSPYEKV SAGNGGSSLS
YTNPAVAATS ANL

A truncated MUC1 receptor isoform having nat-
PSMGFR + PSIBR + Unique Region + Repeats at its
N-terminus and including the transmembrane and
cytoplasmic sequences of a full-length MUC1 re-
ceptor ("Rep isoform"- shown excluding optional
N-terminus signal sequence, which may be cleaved
after translation and prior to expression of the
receptor on the cell surface):
                                        (SEQ ID NO: 9)
LDPRVRTSAP DTRPAPGSTA PQAHGVTSAP DTRPAPGSTA
PPAHGVTSAP DTRPAPGSTA

PPAHGVTSAP DTRPAPGSTA PPAHGVTSAP DTRPAPGSTA
PPAHGVTSAP DTRPAPGSTA

PPAHGVTSAP DTRPAPGSTA PPAHGVTSAP DTRPAPGSTA
PPAHGVTSAP DTRPAPGSTA

PPAHGVTSAP DTRPAPGSTA PPAHGVTSAP DTRPAPGSTA
PPAHGVTSAP DTRPAPGSTA

PPAHGVTSAP DTRPAPGSTA PPAHGVTSAP DTRPAPGSTA
PPAHGVTSAP DTRPAPGSTA

PPAHGVTSAP DTRPAPGSTA PPAHGVTSAP DTRPAPGSTA
PPAHGVTSAP DTRPAPGSTA

PPAHGVTSAP DTRPAPGSTA PPAHGVTSAP DTRPAPGSTA
PPAHGVTSAP DTRPAPGSTA

PPAHGVTSAP DTRPAPGSTA PPAHGVTSAP DTRPAPGSTA
PPAHGVTSAP DTRPAPGSTA

PPAHGVTSAP DTRPAPGSTA PPAHGVTSAP DTRPAPGSTA
PPAHGVTSAP DTRPAPGSTA
```

TABLE 1-continued

```
PPAHGVTSAP DNRPALGSTA PPVHNVTSAS GSASGSASTL
VHNGTSARAT TTPASKSTPF

SIPSHHSDTP TTLASHSTKT DASSTHHSSV PPLTSSNHST
SPQLSTGVSF FFLSFHISNL

QFNSSLEDPS TDYYQELQRD ISEMFLQIYK QGGFLGLSNI
KFRPGSVVVQ LTLAFREGTI

NVHDVETQFN QYKTEAASRY NLTISDVSVS DVPFPFSAQS
GAGVPGWGIA LLVLVCVLVA

LAIVYLIALA VCQCRRKNYG QLDIFPARDT YHPMSEYPTY
HTHGRYVPPS STDRSPYEKV

SAGNGGSSLS YTNPAVAAAS ANL
```

Native Primary Sequence of the MUC1 Growth Factor Receptor (nat-PSMGFR—an example of "PSMGFR"): GTINVHDVETQFNQYKTEAASRYNLTIS-DVSVSDVPFPFSAQSGA (SEQ ID NO: 10)

Native Primary Sequence of the MUC1 Growth Factor Receptor (nat-PSMGFR—An example of "PSMGFR"), having a single amino acid deletion at the N-terminus of SEQ ID NO: 10): TINVHDVETQFNQYKTEAASRYNLTISD-VSVSDVPFPFSAQSGA (SEQ ID NO: 11)

"SPY" functional variant of the native Primary Sequence of the MUC1 Growth Factor Receptor having enhanced stability (var-PSMGFR—An example of "PSMGFR"): GTINVHD-VETQFNQYKTEAASPYNLTISDVSVSD-VPFPFSAQSGA (SEQ ID NO: 12)

"SPY" functional variant of the native Primary Sequence of the MUC1 Growth Factor Receptor having enhanced stability (var-PSMGFR—An example of "PSMGFR"), having a single amino acid deletion at the C-terminus of SEQ ID NO: 12): TINVHDVETQFNQYKTEAASPYNLTISD-VSVSDVPFPFSAQSGA (SEQ ID NO: 13)

Truncated PSMGFR receptor (TR) (having "SPY" sequence of var-PSMGFR): GTINVHDVETQFNQYKTEAASPYN-LTISDVSVS (SEQ ID NO: 14)

Extended Sequence of MUC1 Growth Factor Receptor (ES-MGFR) (having "SPY" sequence of var-PSMGFR): VQLT-LAFREGTINVHDVETQFNQYK-TEAASPYNLTISDVSVSDVPFPF (SEQ ID NO: 15)

Tumor-Specific Extended Sequence of MUC1 Growth Factor Receptor (TSESMGFR) (having "SPY" sequence of var-PSMGFR): SVVVQLTLAFREGTINVHDVETQFNQYK-TEAASPYNLTISDVSVS DVPFPFSAQSGA (SEQ ID NO: 16)

Primary Sequence of the Interchain Binding Region) (PSIBR): GFLGLSNIKFRPGSVVVQLTLAFRE (SEQ ID NO: 17)

Truncated Interchain Binding Region) (TPSIBR): SVVVQLTLAFREG (SEQ ID NO: 18)

Repeat Motif 2 (RM2): PDTRPAPGSTAPPAHGVTSAP-DTRPAPGSTAPPAHGVTSA (SEQ ID NO: 19)

TABLE 2

Nucleic acid sequences encoding for truncated isoforms of MUC1 receptor (listed from 5'-terminus to 3'-terminus):

An example of a nucleic acid molecule encoding the full-length MUC1 receptor of SEQ ID NO: 1:
acaggttctggtcatgcaagctctaccccaggtggagaaaaggagacttcggctacccagagaagtt (SEQ ID NO: 20)

cagtgcccagctctactgagaagaatgctgtgagtatgaccagcagcgtactctccagccacagccc cggttcaggctcctccaccactcagggacaggatgtcactctggccccggccacggaaccagcttca TABLE 2-continued

```
ggttcagctgccacctggggacaggatgtcacctcggtcccagtcaccaggccagccctgggctcca ccaccccgccagcccacgatgtcacctcagccccggacaacaagccagccccgggctccaccgcccc cccagcccacggtgtcacctcggccccggacaccaggccggccccgggctccaccgccccccagcc cacggtgtcacctcggccccggacaccaggccggccccgggctccaccgccccccagcccacggtg tcacctcggccccggacaccaggccggccccgggctccaccgccccccagcccacggtgtcacctc ggccccggacaccaggccggccccgggctccaccgccccccagcccacggtgtcacctcggccccg gacaccaggccggccccgggctccaccgccccccagcccacggtgtcacctcggccccggacacca ggccggccccgggctccaccgccccccagcccacggtgtcacctcggccccggacaccaggccggc cccgggctccaccgccccccagcccacggtgtcacctcggccccggacaccaggccggccccgggc tccaccgccccccagcccacggtgtcacctcggccccggacaccaggccggccccgggctccaccg ccccccagcccacggtgtcacctcggccccggacaccaggccggccccgggctccaccgccccccc agcccacggtgtcacctcggccccggacaccaggccggccccgggctccaccgccccccagcccac ggtgtcacctcggccccggacaccaggccggccccgggctccaccgccccccagcccacggtgtca cctcggccccggacaccaggccggccccgggctccaccgccccccagcccacggtgtcacctcggc cccggacaccaggccggccccgggctccaccgccccccagcccacggtgtcacctcggccccggac accaggccggccccgggctccaccgccccccagcccacggtgtcacctcggccccggacaccaggc cggccccgggctccaccgccccccagcccacggtgtcacctcggccccggacaccaggccggcccc gggctccaccgccccccagcccacggtgtcacctcggccccggacaccaggccggccccgggctcc accgccccccagcccacggtgtcacctcggccccggacaccaggccggccccgggctccaccgccc cccagcccacggtgtcacctcggccccggacaccaggccggccccgggctccaccgccccccagc ccacggtgtcacctcggccccggacaccaggccggccccgggctccaccgccccccagcccacggt gtcacctcggccccggacaccaggccggccccgggctccaccgccccccagcccacggtgtcacct cggccccggacaccaggccggccccgggctccaccgccccccagcccacggtgtcacctcggcccc ggacaccaggccggccccgggctccaccgccccccagcccacggtgtcacctcggccccggacacc aggccggccccgggctccaccgccccccagcccacggtgtcacctcggccccggacaccaggccgg ccccgggctccaccgccccccagcccacggtgtcacctcggccccggacaccaggccggccccggg ctccaccgccccccagcccacggtgtcacctcggccccggacaccaggccggccccgggctccacc gccccccagcccacggtgtcacctcggccccggacaccaggccggccccgggctccaccgccccc cagcccacggtgtcacctcggccccggacaccaggccggccccgggctccaccgccccccagccca cggtgtcacctcggccccggacaccaggccggccccgggctccaccgccccccagcccacggtgtc acctcggccccggacaccaggccggccccgggctccaccgccccccagcccacggtgtcacctcgg ccccggacaccaggccggccccgggctccaccgccccccagcccacggtgtcacctcggccccgga caccaggccggccccgggctccaccgccccccagcccacggtgtcacctcggccccggacaccagg ccggccccgggctccaccgccccccagcccacggtgtcacctcggccccggacaccaggccggccc cgggctccaccgccccccagcccacggtgtcacctcggccccggacaccaggccggccccgggctc caccgccccccagcccacggtgtcacctcggccccggacaccaggccggccccgggctccaccgcc ccccagcccacggtgtcacctcggccccggacaccaggccggccccgggctccaccgccccccag cccacggtgtcacctcggccccggacaccaggccggccccgggctccaccgccccccagcccatgg tgtcacctcggccccggacaacaggcccgccttgggctccaccgcccctccagtccacaatgtcacc tcggcctcaggctctgcatcaggctcagcttctactctggtgcacaacggcacctctgccagggcta
```

TABLE 2-continued ccacaacccagccagcaagagcactccattctcaattcccagccaccactctgatactcctaccac ccttgccagccatagcaccaagactgatgccagtagcactcaccatagctcggtacctcctctcacc tcctccaatcacagcacttctccccagttgtctactggggtctctttcttttcctgtcttttcaca tttcaaacctccagtttaattcctctctggaagatcccagcaccgactactaccaagagctgcagag agacatttctgaaatgtttttgcagatttataaacaaggggttttctgggcctctccaatattaag ttcaggccaggatctgtggtggtacaattgactctggccttccgagaaggtaccatcaatgtccacg acgtggagacacagttcaatcagtataaaacggaagcagcctctcgatataacctgacgatctcaga cgtcagcgtgagtgatgtgccatttcctttctctgcccagtctggggctggggtgccaggctgggc atcgcgctgctggtgctggtctgtgttctggttgcgctggccattgtctatctcattgccttggctg tctgtcagtgccgccgaaagaactacgggcagctggacatctttccagcccgggatacctaccatcc tatgagcgagtaccccacctaccacacccatgggcgctatgtgcccccctagcagtaccgatcgtagc ccctatgagaaggtttctgcaggtaacggtggcagcagcctctcttacacaaacccagcagtggcag ccgcttctgccaacttgtagggcacgtcgccgctgagctgagtggccagccagtgccattccactcc actcaggttcttcaggccagagcccctgcaccctgtttgggctggtgagctgggagttcaggtgggc tgctcacagcctccttcagaggccccaccaatttctcggacacttctcagtgtgtggaagctcatgt gggcccctgaggctcatgcctgggaagtgttgtggggctcccaggaggactggcccagagagccct gagatagcggggatcctgaactggactgaataaaacgtggtctcccactg An example of a nucleic acid molecule encoding the nat-PSMGFRTC of SEQ ID NO: 5:
Acgggcacggccggtaccatcaatgtccacgacgtggagacacagttcaatcagtataaaacggaag (SEQ ID NO: 21)

cagcctctcgatataacctgacgatctcagacgtcagcgtgagtgatgtgccatttcctttctctgc ccagtctggggctggggtgccaggctggggcatcgcgctgctggtgctggtctgtgttctggttgcg ctggccattgtctatctcattgccttggctgtctgtcagtgccgccgaaagaactacgggcagctgg acatctttccagcccgggatacctaccatcctatgagcgagtaccccacctaccacacccatgggcg ctatgtgccccctagcagtaccgatcgtagcccctatgagaaggtttctgcaggtaacggtggcagc agcctctcttacacaaacccagcagtggcagccgcttctgccaacttgtagggcacgtcgccgctga gctgagtggccagccagtgccattccactccactcaggttcttcaggccagagcccctgcaccctgt ttgggctggtgagctgggagttcaggtgggctgctcacagcctccttcagaggccccaccaatttct cggacacttctcagtgtgtggaagctcatgtgggcccctgaggctcatgcctgggaagtgttgtggg ggctcccaggaggactggcccagagagccctgagatagcggggatcctgaactggactgaataaaac gtggtctcccactg An example of a nucleic acid molecule encoding the CM isoform of SEQ ID NO: 6:
Acggccggttttctgggcctctccaatattaagttcaggccaggatctgtggtggtacaattgactc (SEQ ID NO: 22)

tggccttccgagaaggtaccatcaatgtccacgacgtggagacacagttcaatcagtataaaacgga agcagcctctcgatataacctgacgatctcagacgtcagcgtgagtgatgtgccatttcctttctct gcccagtctggggctggggtgccaggctggggcatcgcgctgctggtgctggtctgtgttctggttg cgctggccattgtctatctcattgccttggctgtctgtcagtgccgccgaaagaactacgggcagct ggacatctttccagcccgggatacctaccatcctatgagcgagtaccccacctaccacacccatggg cgctatgtgccccctagcagtaccgatcgtagcccctatgagaaggtttctgcaggtaacggtggca gcagcctctcttacacaaacccagcagtggcagccgcttctgccaacttgtagggcacgtcgccgct gagctgagtggccagccagtgccattccactccactcaggttcttcaggccagagcccctgcaccct gtttgggctggtgagctgggagttcaggtgggctgctcacagcctccttcagaggccccaccaattt

TABLE 2-continued ctcggacacttctcagtgtgtggaagctcatgtgggccctgaggctcatgcctgggaagtgttgtg ggggctcccaggaggactggcccagagagccctgagatagcggggatcctgaactggactgaataaa acgtggtctcccactg An example of a nucleic acid molecule encoding the UR isoform of SEQ ID NO: 7:
Acggccgctaccacaaccccagccagcaagagcactccattctcaattcccagccaccactctgata (SEQ ID NO: 23)

ctcctaccacccttgccagccatagcaccaagactgatgccagtagcactcaccatagctcggtacc tcctctcacctcctccaatcacagcacttctccccagttgtctactggggtctcttctttttcctg tcttttcacatttcaaacctccagtttaattcctctctggaagatcccagcaccgactactaccaag agctgcagagagacatttctgaaatgttttgcagatttataaacaaggggttttctgggcctctc caatattaagttcaggccaggatctgtggtggtacaattgactctggccttccgagaaggtaccatc aatgtccacgacgtggagacacagttcaatcagtataaaacggaagcagcctctcgatataacctga cgatctcagacgtcagcgtgagtgatgtgccatttcctttctctgcccagtctgggctggggtgcc aggctggggcatcgcgctgctggtgctggtctgtgttctggttgcgctggccattgtctatctcatt gccttggctgtctgtcagtgccgccgaaagaactacgggcagctggacatctttccagcccgggata cctaccatcctatgagcgagtaccccacctaccacacccatgggcgctatgtgcccctagcagtac cgatcgtagcccctatgagaaggtttctgcaggtaacggtggcagcagcctctcttacacaaaccca gcagtggcagccgcttctgccaacttgtagggcacgtcgccgctgagctgagtggccagccagtgcc attccactccactcaggttcttcaggccagagccctgcaccctgtttgggctggtgagctgggagt tcaggtgggctgctcacagcctccttcagaggccccaccaatttctcggacacttctcagtgtgtgg aagctcatgtgggccctgaggctcatgcctgggaagtgttgtgggggctcccaggaggactggccc agagagccctgagatagcggggatcctgaactggactgaataaaacgtggtctcccactg An example of a nucleic acid molecule encoding the Y isoform of SEQ ID NO: 8:
Acaggttctggtcatgcaagctctaccccaggtggagaaaaggagacttcggctacccagagaagtt (SEQ ID NO: 24)

cagtgcccagctctactgagaagaatgcttttaattcctctctggaagatcccagcaccgactacta ccaagagctgcagagagacatttctgaaatgttttgcagatttataaacaaggggttttctgggc ctctccaatattaagttcaggccaggatctgtggtggtacaattgactctggccttccgagaaggta ccatcaatgtccacgacgtggagacacagttcaatcagtataaaacggaagcagcctctcgatataa cctgacgatctcagacgtcagcgtgagtgatgtgccatttcctttctctgcccagtctggggctggg gtgccaggctggggcatcgcgctgctggtgctggtctgtgttctggttgcgctggccattgtctatc tcattgccttggctgtctgtcagtgccgccgaaagaactacgggcagctggacatctttccagcccg ggatacctaccatcctatgagcgagtaccccacctaccacacccatgggcgctatgtgcccctagc agtaccgatcgtagcccctatgagaaggtttctgcaggtaatggtggcagcagcctctcttacacaa acccagcagtggcagccacttctgccaacttgtaggggcacgtcgcc An example of a nucleic acid molecule encoding the Rep isoform of SEQ ID NO: 9:
ctcgacccacgcgtccgctcgacccacgcgtccgcacctcggccccggacaccaggccggccccggg (SEQ ID NO: 25)

ctccaccgcccccccagcccacggtgtcacctcggccccggacaccaggccggccccgggctccacc gcccccccagcccacggtgtcacctcggccccggacaccaggccggccccgggctccaccgccccc cagcccacggtgtcacctcggccccggacaccaggccggccccgggctccaccgccccccagccca cggtgtcacctcggccccggacaccaggccggccccgggctccaccgccccccagcccacggtgtc acctcggccccggacaccaggccggccccgggctccaccgccccccagcccacggtgtcacctcgg ccccggacaccaggccggccccgggctccaccgccccccagcccacggtgtcacctcggccccgga TABLE 2-continued

```
caccaggccggccccgggctccaccgcccccccagcccacggtgtcacctcggccccggacaccagg
ccggccccgggctccaccgcccccccagcccacggtgtcacctcggccccggacaccaggccggcc
cgggctccaccgcccccccagcccacggtgtcacctcggccccggacaccaggccggccccgggctc
caccgcccccccagcccacggtgtcacctcggccccggacaccaggccggccccgggctccaccgcc
ccccagcccacggtgtcacctcggccccggacaccaggccggccccgggctccaccgcccccccag
cccacggtgtcacctcggccccggacaccaggccggccccgggctccaccgcccccccagcccacgg
tgtcacctcggccccggacaccaggccggccccgggctccaccgcccccccagcccacggtgtcacc
tcggccccggacaccaggccggccccgggctccaccgcccccccagcccacggtgtcacctcggccc
cggacaccaggccggccccgggctccaccgcccccccagcccacggtgtcacctcggccccggacac
caggccggccccgggctccaccgcccccccagcccacggtgtcacctcggccccggacaccaggccg
gccccgggctccaccgcccccccagcccacggtgtcacctcggccccggacaccaggccggcccgg
gctccaccgcccccccagcccatggtgtcacctcggccccggacaacaggcccgccttgggctccac
cgcccctccagtccacaatgtcacctcggcctcaggctctgcatcaggctcagcttctactctggtg
cacaacggcacctctgccagggctaccacaaccccagccagcaagagcactccattctcaattccca
gccaccactctgatactcctaccacccttgccagccatagcaccaagactgatgccagtagcactca
ccatagctcggtacctcctctcacctcctccaatcacagcacttctccccagttgtctactggggtc
tctttcttttcctgtcttttcacatttcaaacctccagtttaattcctctctggaagatcccagca
ccgactactaccaagagctgcagagagacatttctgaaatgtttttgcagatttataaacaaggggg
ttttctgggcctctccaatattaagttcaggccaggatctgtggtggtacaattgactctggccttc
cgagaaggtaccatcaatgtccacgacgtggagacacagttcaatcagtataaaacggaagcagcct
ctcgatataacctgacgatctcagacgtcagcgtgagtgatgtgccatttcctttctctgcccagtc
tggggctggggtgccaggctggggcatcgcgctgctggtgctggtctgtgttctggttgcgctggcc
attgtctatctcattgccttggctgtctgtcagtgccgccgaaagaactacgggcagctggacatct
ttccagcccgggatacctaccatcctatgagcgagtaccccacctaccacacccatgggcgctatgt
gcccctagcagtaccgatcgtagcccctatgagaaggtttctgcaggtaacggtggcagcagcctc
tcttacacaaacccagcagtggcagccgcttctgccaacttgtagggcacgtcgccgctgagctgag
tggccagccagtgccattccactccactcaggttcttcaggccagagccctgcaccctgtttgggc
tggtgagctgggagttcaggtgggctgctcacagcctccttcagaggccccaccaatttctcggaca
cttctcagtgtgtggaagctcatgtgggcccctgaggctcatgcctgggaagtgttgtggggctcc
caggaggactggcccagagagccctgagatagcggggatcctgaactggactgaataaaacgtggtc
tcccactg
```

TABLE 3

| Cell Type | Reference | Indication |
|---|---|---|
| Immature Erythrocytes | Regulated expression of MUC1 epithelial antigen in erythropoiesis. Rughetti A, Biffoni M, Pierelli L, Rahimi H, Bonanno G, Barachini S, Pellicciotta I, Napoletano C, Pescarmona E, Del Nero A, Pignoloni P, Frati L and Nuti M. (2003) Br. J. Haematol, 120(2): 344-352 | Treatment of Blood diseases, anemia |

TABLE 3-continued

| Cell Type | Reference | Indication |
| --- | --- | --- |
| Dendritic Cells | Mucin-1 is expressed on dendritic cells, both in vitro and in vivo. Cloosen S, Thio M, Vanclee A, van Leeuwen EB, Senden-Gijsbers BL, Oving EB, Germeraad WT, Bos GM. (2004) Int. Immunol. 11, 1561-71 | Treatment of Immune diseases, especially immune-deficiency diseases |
| Epithelial Progenitor Cells | Epithelial progenitors in the normal human mammary gland. Stingl J, Raouf A, Emerman JT, Eaves CJ. J Mammary Gland Biol Neoplasia. (2005) Jan; 10(1): 49-59. | Tissue regeneration Tissue augmentation |
| Monoblasts and Monocytes | Epithelial membrane antigen (EMA) or MUC1 expression in monocytes and monoblasts. Leong CF, Raudhawati O, Cheong SK, Sivagengi K and Noor Hamdiah H. 2003 Pathology, 35, 422-427 | Treatment of patients following chemotherapy and/or radiation therapy Other conditions in which it is desirable to augment macrophage lineage |
| Endometrial Cells | Human endometrial mucin MUC1 is up-regulated by progesterone and down-regulated in vitro by the human blastocyst. Meseguer M, Aplin JD, Caballero-Campo P, O'Connor JE, Martin JC, Remohi J, Pellicer A, Simon C. (2001) Biol. Reprod. 64(2) 590-601 | For the treatment of endometriosis, and other fertility related conditions |
| Pneumocyte | MUC1 is a novel marker for the type II pneumocyte lineage during lung carcinogenesis. JA Jarrard, RI Linnoila, H Lee, SM Steinberg, H Witschi and E Szabo. (1998) Cancer Research, 58, (23) 5582-5589 | For the treatment of respiratory diseases |
| Neutrophils and Precursors | G-CSF induces elevation of circulating CA 15-3 in breast carcinoma patients treated in an adjuvant setting. Briasoulis E, Andreopoulou E, Tolis CF, Bairaktari E, Katsaraki A, Dimopoulos MA, Fountzilas G, Seferiadis C ans Pavlidis N. (2001) Cancer, 91, 909-917 | For the treatment of blood diseases, and Neutropenia For the treatment of patients receiving ablative radiation, to replace bone marrow transplantation |
| Mast Cells | Applicant | For the treatment of immuno-compromised patients |

What is claimed is:

1. A method for stimulating or enhancing proliferation of a population of non-tumorous cells by contacting the cells with a substance that activates mucin 1 (MUC1) receptor on the cells, comprising contacting the cells with an effective amount of NM23 protein or a bivalent antibody that binds to and multimerizes the MUC1 Growth Factor Receptor (MGFR) portion of mucin 1 (MUC1), wherein said substance is NM23 protein or a bivalent antibody.

2. The method according to claim 1, wherein the cells are immature cells.

3. The method according to claim 2, wherein the cells are chosen from a group consisting of stem cells, progenitor cells, endometrial cells, neutrophil pre-cursors and neutrophils.

4. The method according to claim 1, wherein the mucin 1 (MUC1) receptor is a cell surface-attached cleavage product.

5. The method according to claim 4, wherein the mucin 1 (MUC1) cleavage product is MUC1 Growth Factor Receptor (MGFR).

6. The method according to claim 5, wherein the MUC1 Growth Factor Receptor (MGFR) consists essentially of the Primary Sequence of the MUC1 Growth Factor Receptor (PSMGFR).

7. The method according to claim 1, wherein the antibody is monoclonal antibody.

8. The method according to claim 1, wherein the NM23 protein or bivalent antibody dimerizes the MUC1 Growth Factor Receptor (MGFR) portion of the mucin 1 (MUC1) receptor.

9. The method according to claim 3, wherein the stem cell is umbilical cord blood cells, liver stem cells, pancreatic stem cells, neuronal stem cells, bone marrow stem cells, peripheral blood stem cells, or mesenchymal stromal cells.

10. A method for treating a patient displaying symptoms of a low white blood count comprising administering to the patient an effective amount of an agent for activating mucin 1 (MUC1) receptor on cells, wherein the agent is NM23 protein or a bivalent antibody that binds to and multimerizes the MUC1 Growth Factor Receptor (MGFR) portion of mucin 1 (MUC1).

11. The method according to claim 10, wherein mucin 1 (MUC1) is further activated by increasing the production of MUC1 or post-translationally modified MUC1 by adding Granulocyte-Colony Stimulating Factor (G-CSF).

12. The method according to claim 10, wherein the cells are immature cells.

13. The method according to claim 12, wherein the cells are chosen from a group consisting of stem cells, progenitor cells, endometrial cells, neutrophil pre-cursors and neutrophils.

14. The method according to claim 10, wherein the mucin 1 (MUC1) receptor is a cell surface-attached cleavage product.

15. The method according to claim 14, wherein the mucin 1 (MUC1) cleavage product is MUC1 Growth Factor Receptor (MGFR).

16. The method according to claim 15, wherein the MUC1 Growth Factor Receptor (MGFR) consists essentially of the Primary Sequence of the MUC1 Growth Factor Receptor (PSMGFR).

17. The method according to claim 10, wherein the antibody is monoclonal antibody.

18. The method according to claim 10, wherein mucin 1 (MUC1) is activated by dimerizing the MUC1 Growth Factor Receptor (MGFR) portion of the mucin 1 (MUC1) receptor.

19. The method according to claim 13, wherein the stem cell is umbilical cord blood cells, liver stem cells, pancreatic stem cells, neuronal stem cells, bone marrow stem cells, peripheral blood stem cells, or mesenchymal stromal cells.

20. A method for treating a patient, who displays symptoms indicating that a medicinal benefit would be achieved by causing immature cells to proliferate, comprising administering to the patient an effective amount of an agent for activating mucin 1 (MUC1) receptor on cells, wherein the agent is NM23 protein or a bivalent antibody that binds to and multimerizes the MUC1 Growth Factor Receptor (MGFR) portion of mucin 1 (MUC1).

21. The method according to claim 20, wherein mucin 1 (MUC1) is activated by dimerizing the MUC1 Growth Factor Receptor (MGFR) portion of the mucin 1 (MUC1) receptor.

22. The method according to claim 20, wherein the patient is being treated with chemotherapy agents for the treatment of mucin 1 (MUC1)-negative cancers.

23. The method according to claim 20, wherein the cells are immature cells.

24. The method according to claim 23, wherein the cells are chosen from a group consisting of stem cells, progenitor cells, endometrial cells, neutrophil pre-cursors and neutrophils.

25. The method according to claim 20, wherein the mucin 1 (MUC1) receptor is a cell surface-attached cleavage product.

26. The method according to claim 25, wherein the mucin 1 (MUC1) cleavage product is MUC1 Growth Factor Receptor (MGFR).

27. The method according to claim 26, wherein the MUC1 Growth Factor Receptor (MGFR) consists essentially of the Primary Sequence of the MUC1 Growth Factor Receptor (PSMGFR).

28. The method according to claim 20, wherein the antibody is monoclonal antibody.

29. The method according to claim 24, wherein the stem cell is umbilical cord blood cells, liver stem cells, pancreatic stem cells, neuronal stem cells, bone marrow stem cells, peripheral blood stem cells, or mesenchymal stromal cells.

30. The method according to claim 20, wherein the NM23 protein or bivalent antibody dimerizes the MUC1 Growth Factor Receptor (MGFR) portion of the mucin 1 (MUC1) receptor.

31. A method for stimulating or enhancing proliferation of a population of non-tumorous cells in vitro by contacting the cells with a substance that activates mucin 1 (MUC1) receptor on the cells, comprising contacting the cells with NM23 protein or a bivalent antibody that binds to and multimerizes the MUC1 Growth Factor Receptor (MGFR) portion of mucin 1 (MUC1), wherein said substance is NM23 protein or a bivalent antibody.

32. The method according to claim 31, wherein the cells are immature cells.

33. The method according to claim 32, wherein the cells are chosen from a group consisting of stem cells, progenitor cells, endometrial cells, neutrophil pre-cursors and neutrophils.

34. The method according to claim 31, wherein the mucin 1 (MUC1) receptor is a cell surface-attached cleavage product.

35. The method according to claim 34, wherein the mucin 1 (MUC1) cleavage product is MUC1 Growth Factor Receptor (MGFR).

36. The method according to claim 35, wherein the MUC1 Growth Factor Receptor (MGFR) consists essentially of the Primary Sequence of the MUC1 Growth Factor Receptor (PSMGFR).

37. The method according to claim 31, wherein the antibody is monoclonal antibody.

38. The method according to claim 31, wherein the NM23 protein or bivalent antibody dimerizes the MUC1 Growth Factor Receptor (MGFR) portion of the mucin 1 (MUC1) receptor.

39. The method according to claim 31, wherein mucin 1 (MUC1) is further activated by increasing the production of MUC1 or post-translationally modified MUC1, comprising the steps of transfecting the cells with an expression vector comprising a polynucleotide encoding MUC1 receptor or the MGFR portion thereof; and allowing the cells to express the MUC1 receptor or the MGFR portion thereof.

40. The method according to claim 33, wherein the stem cell is umbilical cord blood cells, liver stem cells, pancreatic stem cells, neuronal stem cells, bone marrow stem cells, peripheral blood stem cells, or mesenchymal stromal cells.

* * * * *